United States Patent [19]

Terao et al.

[11] Patent Number: 5,180,742
[45] Date of Patent: Jan. 19, 1993

[54] QUINONE DERIVATIVES, THEIR PRODUCTION AND USE

[75] Inventors: Shinji Terao, Toyonaka; Yoshitaka Maki, Kyoto, both of Japan

[73] Assignee: Takeda Chemical Industries, Ltd., Osaka, Japan

[21] Appl. No.: 1,893

[22] Filed: Jan. 9, 1987

Related U.S. Application Data

[63] Continuation-in-part of Ser. No. 823,298, Jan. 28, 1986, abandoned, which is a continuation-in-part of Ser. No. 760,504, Jul. 30, 1985, abandoned.

[30] Foreign Application Priority Data

Aug. 1, 1984 [JP] Japan .................................. 00393
Jan. 8, 1985 [JP] Japan .................................. 00003

[51] Int. Cl.$^5$ ............................................. A01N 37/00
[52] U.S. Cl. ............................. 514/558; 514/690; 514/718; 514/734; 568/734; 568/737; 568/744; 568/735; 564/170; 564/172; 552/307; 552/309; 552/310; 554/129; 554/132; 554/154
[58] Field of Search ............... 260/396 R, 413; 514/558, 690, 718, 734; 568/734, 737, 744, 745; 564/170, 172; 552/307, 309, 310; 554/129, 132, 154

[56] References Cited

U.S. PATENT DOCUMENTS

| 4,139,545 | 2/1979 | Morimoto et al. | 260/396 R |
| 4,271,083 | 6/1981 | Morimoto et al. | 260/396 R |
| 4,358,461 | 11/1982 | Maki et al. | 424/331 |
| 4,393,075 | 7/1983 | Terao et al. | 424/304 |
| 4,489,096 | 12/1984 | Terao et al. | 424/317 |
| 4,495,104 | 1/1985 | Imada et al. | 260/396 S |
| 4,559,177 | 12/1985 | Okutani et al. | 260/396 R |

FOREIGN PATENT DOCUMENTS

0021841 1/1981 European Pat. Off.
31727 7/1981 European Pat. Off.

OTHER PUBLICATIONS

Citterio, A., Chemical Abstracts, 94:15335c, 1980.
Jurd, L., Chemical Abstracts, 88:135864x, 1978.
Citterio, A., Chemical Abstracts, 90:38265m, 1978.
Jurd, L., Chemical Abstracts, 93:114350g, 1980.
Jurd, L., Chemical Abstracts 92:76262g, 1979.
Armour et al., *Clinical and Experimental Pharmacology & Physiology*, 8, pp. 654-655 (1981).
Yoshimoto et al., *Biochemical and Biophysical Research Communication* 116, 612-618 (1983).
Kuhn et al., *European Journal of Biochemistry* 139, 557-583 (1984).
Watanabe et al., Chem. Pharm. Bull., 26 (3), 774-783 (1978).
Citterio, Tetrahedron Letters, No. 30, pp. 2701-2704 (1978).

*Primary Examiner*—Jose G. Dees
*Assistant Examiner*—Joseph Conrad, III
*Attorney, Agent, or Firm*—Wenderoth, Lind & Ponack

[57] ABSTRACT

Quinone derivatives of the general formula: , 10 (wherein $R^1$ and $R^2$ are the same or different, and independently are a hydrogen atom or a methyl or methoxy group, or $R^1$ and $R^2$ combine with each other to represent —CH=CH—CH=CH—$R^3$ is a hydrogen atom or a methyl group; $R^4$ is an aliphatic, aromatic or heterocyclic group which may be substituted; $R^5$ is a methyl or methoxy group, a hydroxymethyl group which may be substituted or a carboxyl group which may be esterified or amidated; Z is a group represented by —C≡C—, —CH=CH—, , 11 n is an integer of 0 to 10; m is an integer of 0 to 3; k is an integer of 0 to 5, provided, however, that in the case of m being 2 or 3, Z and k can vary arbitrarily within the bracketed repeating units) are novel compounds, possess metabolism ameliorating action for polyunsaturated fatty acids, particularly production inhibitory activity of lipid peroxides (antioxidant activity), thromboxane $A_2$ receptor antagonism, or production inhibitory activity of 5-lipoxygenase metabolites in mammals, and of use as drugs, such as antiasthmatic, antiallergic agent and cerebral-circulatory metabolism ameliorating agent.

11 Claims, No Drawings

QUINONE DERIVATIVES, THEIR PRODUCTION AND USE

This application is a continuation-in-part of application Ser. No. 823,298, filed Jan. 28, 1986, now abandoned which in turn is a continuation-in-part of application Ser. No. 760,504, filed Jul. 30, 1985, now abandoned.

This invention relates to novel quinone derivatives which possess therapeutic and prophylactic actions against bronchial asthma, immediate-type allergy, various types of inflammations, arterioscelrosis, endotoxin shock associated with bacterial infection, etc., to a process for producing the same and to pharmaceutical compositions containing the same, and can be utilized in the field of medicine.

Heretofore, it has been regarded as difficult to perform effectively the treatment or prevention of bronchial asthma. In recent years, SRS-A (slow-reacting substance of naphylaxis) which has long been known as one of the important chemical mediators for immediate-type hypersensitivity and asthma was shown to be composed of the 5-liopoxygenase metabolites of arachidonic acid, namely leukotrienes, which have been attracting attention. The leukotrienes are a potent chemical mediator for the allergic or inflammatory reaction, and is considered to cause mainly constriction of peripheral airways in the lung, being related with respiration distress accompanied by bronchial asthma. Also, the leukotrienes possess the capabilities to enhance the capillary permeability and to strongly produce chemotactic activity of leukocytes, and are intimately associated with edema and cellular infiltration, which are typical symptoms of inflammation. They, furthermore, with their potent vasoconstriction action, are considered to contribute eventually to the incidence of coronary insufficiency and angina pectoris. According as the pathophysiologic significance of the leukotrienes has become clarified as is described above, the importance of the 5-lipoxygenase, a key enzyme for the biosynthesis of the leukotrienes, has come to be recognized.

As the compound exhibiting 5-lipoxygenase inhibitory activity, there have already been known flavone compounds, quinone compounds [the U.S. Pat. No. 4,271,083, EPC Laid-Open No. 21841 and U.S. Pat. No. 4,358,461], catechol compounds [Clin. Exp. Pharmacol. Physiol., 8, 654–655 (1981)], phenol, flavone compounds [Biochem. Biophys. Res. Commun., 116, 612–618 (1983)], acetylene compounds [Eur. J. Biochem., 139, 577–583(1984)], etc., but all of them are far from adequately satisfactory in terms of drug metabolism and bioavailability dynamics.

This invention provides novel quinone compounds which less undergo inactivation due to the metabolic system and exhibit more long-acting efficacy than the known compounds shown to possess 5-lipoxygenase inhibitory activity.

This invention is concerned with:

1. A quinone derivative of the general formula:

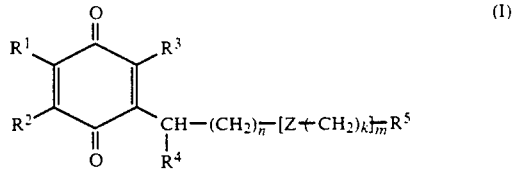

[wherein $R^1$ and $R^2$ are the same or different, and independently are a hydrogen atom or a methyl or methoxy group, or $R^1$ and $R^2$ combine with each other to represent —CH=CH—CH=CH—; $R^3$ is a hydrogen atom or a methyl group; $R^4$ is an aliphatic, aromatic or heterocyclic group which may be substituted; $R^5$ is a methyl or methoxy group, a hydroxymethyl group which may be substituted or a carboxyl group which may be esterified or amidated; Z is a group represented by —C≡C—, —CH=CH—,

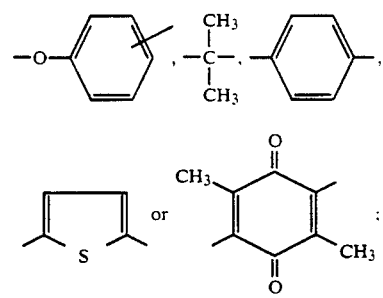

n is an integer of 0 to 10; m is an integer of 0 to 3; k is an integer of 0 to 5, provided, however, that in the case of m being 2 or 3, Z and k can vary arbitrarily within the bracketed repeating unit], or its hydroquinone form, 2. A process for producing a quinone derivative of the general formula (I), characterized in that said process comprises reacting a compound of the general formula:

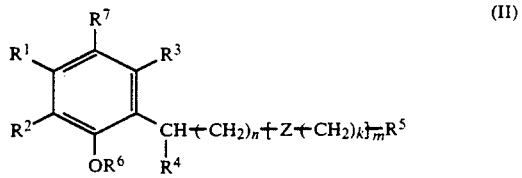

[wherein $R^1$, $R^2$, $R^3$, $R^4$, $R^5$, Z, k, m and n are as defined hereinbefore; $R^6$ is a hydrogen atom, a methyl, methoxymethyl, benzyl or 2-tetrahydropyranyl group; $R^7$ is a hydrogen atom, a hydroxyl, methoxy, methoxymethyloxy, benzyloxy or 2-tetrahydropyranyloxy group] with an oxidizing agent, and 3. A pharmaceutical composition which contains a compound of the general formula (I) or its hydroquinone form as an active ingredient.

In the above general formula (I), the aliphatic group represented by $R^4$ includes, for example, alkyl groups of 1 to 4 carbon atoms, such as methyl, ethyl, n-propyl, i-propyl, n-butyl, i-butyl and t-butyl, alkenyl groups of 2 to 4 carbon atoms, such as vinyl and allyl, and cycloalkyl groups of 3 to 7 carbon atoms, such as cyclopropyl, cyclobutyl, cyclopentyl, cyclohexyl and cycloheptyl; the aromatic group includes, for example, aryl groups, such as phenyl and naphthyl groups; heterocyclic group includes 5- or 6- membered ring containing at least one oxygen atom or at least one sulfur atom as an atom or atoms constituting the ring. and as the embodiment of the heterocyclic group, there may be mentioned, for example, thienyl (2-thienyl, 3-thienyl) and furyl (2-furyl, 3-furyl) groups. These aromatic and heterocyclic groups may have 1 to 5, preferably 1 to 3, of substituents in arbitrary positions on the rings, and such substituents include, for example, a hydroxyl group, halogen atoms, such as fluorine, chlorine and bromine, alkyl groups of 1 to 3 carbon atoms, such as methyl and ethyl, alkoxy groups of 1 to 3 carbon atoms, such as methoxy and ethoxy, and acetyl, phenyl, p-tolyl, m-tolyl, pyridyl (2-pyridyl, 3-pyridyl), 3-pyridylmethyl, benzoyl, methylenedioxy, trimethylene, 1-imidazolyl and 1-imidazolylmethyl

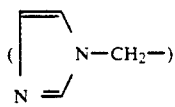

groups. When the aliphatic group is cycloalkyl group, it may have 1 to 5, preferably 1 to 3, of substituents in any positions on the ring, and such substituents include alkyl groups of 1 to 3 carbon atoms, such as methyl and ethyl. $R^4$ is preferably phenyl or m- or p-halogenophenyl.

The hydroxymethyl group represented by $R^5$ may be substituted, and include, for example, unsubstituted hydroxymethyl group as well as methoxymethyloxymethyl, methoxymethyl, acetoxymethyl, nitroxymethyl, aminocarboxymethyl, substituted aminocarbonyloxymethyl, (e.g., methylaminocarbonyloxymethyl, ethylaminocarbonyloxymethyl, dimethylaminocarbonyloxymethyl, phenylaminocarbonyloxymethyl) and cyclic aminocarbonyloxymethyl- (e.g., morpholinocarbonyloxymethyl, piperidinocarbonyloxymethyl, etc.); and as the esterified carboxyl group, for example, there may be mentioned alkoxycarbonyls of 2 to 5 carbon atoms, such as methoxycarbonyl, ethoxycarbonyl, propoxycarbonyl and butoxycarbonyl, and aryloxycarbonyls of 7 to 8 carbon atoms, such as phenoxycarbonyl. The amidated carboxyl group represented by $R^5$ may be substituted aminocarbonyls having its amino group substituted and also cyclic aminocarbonyls. The substituent for the amino group of such substituted aminocarbonyls includes, for example, alkyls of 1 to 4 carbon atoms, such as methyl, ethyl, propyl and butyl, aryls of 6 to 10 carbon atoms (which may have further a substituent or substituents, such as hydroxyl, amino, nitro, halogen, methyl and methoxy, in arbitrary positions on the ring), such as phenyl and naphthyl, and hydroxyl. Specific examples of the amidated carboxyl group include, for example, aminocarbonyl, mono- or di-alkylaminocarbonyl having 2 to 4 carbon atoms (e.g. methylaminocarbonyl, ethylaminocarbonyl, isopropylaminocarbonyl, dimethylaminocarbonyl), aralkylaminocarbonyl[benzylaminocarbonyl, α-phenethylaminocarbonyl, β-phenethylaminocarbonyl, 1-(α-naphthyl)ethylaminocarbonyl], phenylaminocarbonyl, substituted phenylaminocarbonyl (p-hydroxyphenylaminocarbonyl, p-methylaminocarbonyl, m-chlorophenylaminocarbonyl), diphenylaminocarbonyl, hydroxyaminocarbonyl, N-hydroxy-N-methylaminocarbonyl, N-hydroxy-N-phenyl aminocarbonyl, amino acid residue-carbonyl(glycine residue-carbonyl, arginine residue-carbonyl, histidine residue-carbonyl, aspartic acid residue-carbonyl, proline residue-carbonyl, phenylalanine residue-carbonyl, methionine residue-carbonyl, alanine residue-carbonyl and leucine residue-carbonyl.

As the cyclic aminocarbonyl includes morpholinocarbonyl, piperidinocarbonyl, piperadinocarbonyl and pyrrolidinocarbonyl. The cyclic aminocarbonyl may be substituted by 1 to 3 substituents. The substituents includes unsubstituted- or substituted-alkyl (methyl, ethyl, propyl, pyrolidinecarbonylmethyl, 4-fluorophenylcarbonylpropyl, etc.), unsubstituted- or substituted- aryl (phenyl, naphthyl, 2-methoxyphenyl, 4-methylphenyl, 4-bromophenyl, etc.), unsubstituted- or substituted-aralkyl (benzyl, 2-phenylethyl, 4-fluorophenylmethyl, 4-methoxyphenylmethyl, 3,4,5-trimethoxyphenylmethyl, diphenylmethyl, etc.), aminocarbonyl, 6-(9-β-D-ribofuranosido)adenyl and 4-amino-6,7 dimethoxyquinazolinyl. Among the amidated carboxyl groups, aminocarbonyl, carboxymethylaminocarbonyl and 4-ethylpiperazino are preferable, and carbamoyl is the most preferable.

n is preferably 4, 5 or 6.

When m is 2 or 3, the groups: $\left[-Z+CH_2\overline{)_k}\right]_m$ can be shown as follows:

$$Z_1+CH_2\overline{)_{k_1}}-Z_2+CH_2\overline{)_{k_2}}- \quad \text{(when m is 2)}$$

$$Z_1+CH_2\overline{)_{k_1}}-Z_2+CH_2\overline{)_{k_2}}-Z_3+CH_2\overline{)_{k_3}}- \quad \text{(when m is 3)}$$

(wherein $Z_1$, $Z_2$ and $Z_3$ are the same or different and each has the meaning of Z, and $k_1$, $k_2$ and $k_3$ are the same or different and each has the meaning of k.)

In cases where $R^5$ in the compound (I) is a carboxyl group, the compound (I) and its hydroquinone form may be a physiologically acceptable salt such as an alkali metal salt (e.g. sodium salt, potassium salt) or alkaline earth metal salt (e.g. calcium salt, magnesium salt). Among the compound (I), a compound of the formula (I) wherein each of $R^1$, $R^2$ and $R^3$ is methyl, $R^4$ is phenyl or m- or p-halogenophenyl, $R^5$ is carboxyl, hydroxymethyl, aminocarbonyl, carboxymethylaminocarbonyl or 4-phenethylpiperadino, n is 4, 5 or 6 and m is 0 is preferable.

The compound of the general formula (I) according to the present invention can be produced by reacting a compound of the general formula (II) with an oxidizing agent.

With reference to the oxidation of the compound of the general formula (II), the type of oxidizing agent to be used and the reaction conditions to be adopted vary depending upon $R^6$ and $R^7$ in the formula (II).

The compound of the general formula (II) where $R^6$ and $R^7$ independently are a hydrogen atom, namely a phenol compound, can be readily derived to the quinone compound (I) by using a Fremy's salt as an oxidizing agent. In such a case, the amount of Fremy's salt to be used is in the range of 2 to 4 moles per mole of the compound (II), and as the solvent, there are preferably used, for example, methanol, acetonitrile, ethanol, dioxane, 1,2-dimethoxymethane and aqueous solvents of these. The reaction temperature is 10° to 80° C., while the reaction time is normally in the range of 2 to 10 hours.

The compound of the general formula (II) where $R^6$ is a hydrogen atom and $R^7$ is a hydroxy group, namely a hydroquinone compound, can be readily derived to the quinone compound (I) by use of a mild oxidizing agent, such as air, oxygen, Fremy's salt, ferric chloride, ferric sulfate, hydrogen peroxide and peracids. These reactions are carried out normally in the presence of solvent, and as the said solvent, there may be mentioned, for example, methanol, acetonitrile, dioxane, 1,2-dimethoxyethane and aqueous solvent systems consisting of these organic solvents and water. When air or oxygen is used as an oxidizing agent, the reaction is conducted while maintaining a pH of the reaction solution at the neutral to weakly alkaline pH (pH 7.0 to pH 9.0). In order to maintain the pH, a suitable buffer (e.g., from 10° C. to 30° C., and the reaction time is in the range of 1 to 4 hours.

The compounds of the general formula (I) where $R^5$ is a carbamoyloxymethyl, N-substituted-carbamoyloxymethyl, hydroxyaminocarbonyl, N-substituted-hydroxyaminocarbonyl, hydroxymethyl, carboxyl, alkoxycarbonyl, aminocarbonyl or substituted aminocarbonyl group can be derived from the compounds of the general formula (I) where $R^5$ is a hydroxymethyl, carboxyl, alkoxycarbonyl or acyloxymethyl group by the per se known reactions as shown below:

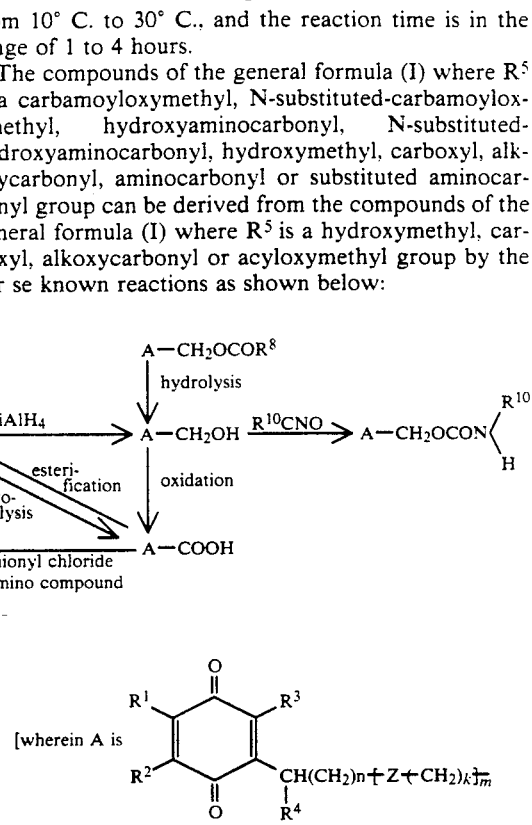

phosphate buffer) is employed. The reaction temperature ranges from $-10°$ C. to 30° C., and the reaction time is normally up to 24 hours.

In cases in which ferric chloride, ferric sulfate, Fremy's salt, hydrogen peroxide or a peracid (e.g., peracetic acid, m-chloroperbenzoic acid) is used as an oxidizing agent, the amount of such oxidizing agents to be used preferably is in the range of 1 to 4 moles per mole of the compound (II). The reaction temperature is normally $-10°$ C. to 30° C., and the reaction time is normally up to 1 hour.

The compounds of the general formula (II) where $R^6$ is a methyl, methoxymethyl, benzyl or 2-tetrahydropyranyl group and $R^7$ is a methoxy, benzyloxy or 2-tetrahydropyranyloxy group, namely hydroquinone diether compounds, can be readily derived to the quinone compounds (I) by using silver oxide (AgO) or ceric ammonium nitrate (hereinafter referred to briefly as "CAN") as an oxidizing agent. In the case of silver oxide (AgO) being used, the reaction is carried out in the temperature range of $-10°$ C. to 30° C. in water or an aqueous organic solvent (e.g., dioxane, acetonitrile) in the presence of nitric acid. In the case of CAN being employed as an oxidizing agent, the reaction is conducted in an aqueous organic solvent (e.g., acetonitrile, methanol), particularly aqueous acetonitrile, in the presence of CAN, either solely or in combination with pyridine-2,6-dicarboxylic acid N-oxide, pyridine-2,4,6-tricarboxylic acid or pyridine-2,6-dicarboxylic acid, etc. The mixing ratio of CAN and the above-described pyridinecarboxylic acids normally is suitably about 1:1 (on a molar equivalent basis). The reaction temperature is in the range of $-5°$ C. to 30° C.

The compounds of the general formula (I) wherein Z is —CH═CH— can also be produced by reducing the compounds of the general formula (I) where Z is —C≡C—. This reaction normally carried out by performing partial reduction in a solvent, such as methanol, ethanol or ethyl acetate with use of quinoline and Rindler catalyst. The amount of the catalyst to be used is in the range of 1/50 to 1/5 (on a weight basis) per mole of the starting compound, while quinoline is employed in the range of 1/10 to 2 (on a weight basis) against the weight of catalyst. The reaction temperature ranges

[wherein A is 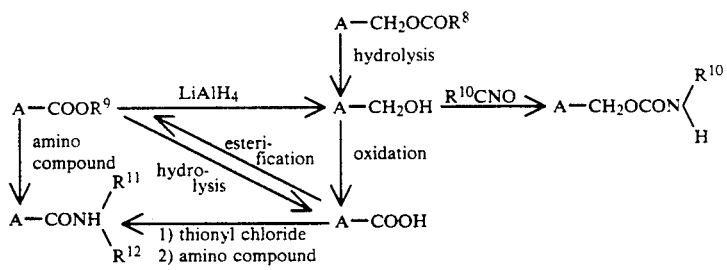

(where $R^1$, $R^2$, $R^3$, $R^4$, n, m, k and Z are as defined hereinbefore); $R^8$ and $R^9$ are independently a $C_{1-3}$ alkyl group (e.g. methyl, ethyl, propyl, etc.); or 4-nitrophenyl group; $R^{10}$ is a $C_{1-7}$ lower alkyl group (e.g. methyl, ethyl, i-propyl, butyl, pentyl, hexyl, etc.) or an aryl group (e.g. phenyl, naphtyl, etc.); $R^{11}$ and $R^{12}$ are independently a hydrogen atom or a group shown by $R^{10}$].

The quinone compound (I) as produced in the above manner can be isolated and collected by the per se known separation and purification means (e.g., chromatography, crystallization method), etc.

The quinone compound (I) of the present invention can readily be undergo interchangeablility with hydroquinone compound of the general formula:

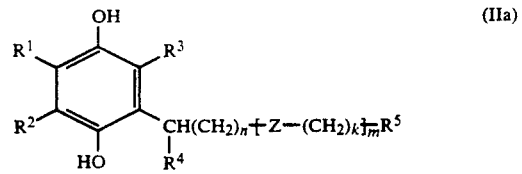

(wherein each of the symbols is as defined hereinbefore) relative to the quinone and hydroquinone nuclei through the chemical or biochemical oxidation and reduction reactions. Since the hydroquinone derivative (IIa) is generally susceptible to oxidation by oxygen, air, etc., the hydroquinone derivative (IIa) is normally handled in the form of the quinone compound (I) as a stable compound. In view of the fact that the chemical and biochemical interchange between the hydroquinone compound (IIa) and the quinone compound (I) easily occurs, the quinone compound (I) and the hydroquinone compound (IIa), when they demonstrate pharmacological activities under physiological conditions, can be regarded as possessing biological equivalent properties.

The quinone compound (I) can be readily converted to the hydroquinone compound (IIa) by conducting reduction by the per se known method with use of a mild reducing agent, such as sodium hydrosulfite, acid sodium sulfite and sodium borohydride.

The quinone compounds (I) and (IIa) have, from the structural standpoint, the asymmetric center of alpha ($\alpha$) carbon in the side-chain of the quinone nucleus, which allows the optically active compounds to exist. Therefore, the compounds (I) and (IIa) of the present invention shall be meant to include any of its optically active compounds and racemic compound.

The compounds (I) and (II) of the present invention exhibit metabolism ameliorating action for polyunsaturated fatty acids (linoleic acid, $\gamma$-linolenic acid, $\alpha$-linolenic acid, arachidonic acid, dihomo-$\gamma$-linolenic acid, eicosapentaenoic acid), particularly inhibitory activity of peroxidation of fatty acids (antioxidant activity), inhibitory activity of 5-lipoxygenase metabolites (e.g., leukotrienes, 5-hydroxyeicosatetraenoic acid, 5-hydroperoxyeicosatetraenoic acid, lipoxins, etc.), inhibitory and/or scavenging action of activated oxygen species (superoxide anion, hydroxy radical, hydrogen peroxide) which are produced in the living cells, strong inhibitory actions of leukotriene $D_4$ or platelet aggregating factor-induced bronchoconstrictions in guinea pigs, improvement of ferric nitrilotriacetate-induced injury of rat kidney, thromboxane $A_2$ receptor antagonism, or inhibitory action on induction of convulsive seizure in the experixental cerebral infarction model of spontaneously hypertensive rats, and also has low toxicity in animal experiments. Consequently, the compounds (I) and (IIa) of the present invention can be expected to develop the therapeutic and prophylactic effects in mammals (mice, rats, rabbits, monkeys, human, etc.) against various diseases, such as bronchial asthma psoriasis, inflammation, immediate type allergy, ischemic heart, brain and kidney, arteriosclerosis, atherosclerosis, immunodeficiency and diminished resistance to bacterial infections, and is useful as drug, such as antiasthmatic, antiallergic agent, therapeutic agent for psoriasis, cerebral-circulatory metabolism ameliorating agent, preventive agent for coronary arteriosclerosis, fatty liver hepatitis, hepatocirrhosis, hyper reactive pneuxonitis, immune regulating agent, protection enhancing agent against bacterial infection and prostagalandin-thromboxane metabolism ameliorating agent. The compounds (I) and (IIa) where $R^4$ is a group containing an imidazole group exhibit thromboxane synthetase inhibitory activity in addition to the above-described actions, and can be used as an antithrombotic agent for the purpose of prevention and treatment of, for example, thrombosis, cardiac infarction, cerebral infarction, heart failure, arrythmia, etc.

The compound of the present invention is low in toxicity, and can be safely administered orally or parenterally, as such or as pharmaceutical compositions [e.g., tablets, capsules (inclusive of soft capsules and microcapsules), solutions, injectable solutions, suppositories] prepared by mixing them with the per se known pharmaceutically acceptable carriers, excipients, etc. Though the dosage level varies depending upon the condition of the patients to be treated, route of administration, conditions of the disease, etc., the compound, for example in the case of oral administration to human adult with asthma, is favorably administered at a single dose of normally about 0.1 mg/kg to 20 mg/kg body weight, preferably about 0.2 mg/kg to 10 mg/kg body weight, about once to twice.

The compounds (I) and (IIa) of the present invention have a bulky group alpha ($\alpha$)-position carbon atom in the side-chain of the quinone or hydroquinone nucleus, and because of this characteristic structure, is less susceptible to an inactivation reaction due to in vivo metabolism. Consequently, the compound can maintain the effective blood concentration level of drug and thus demonstrates improved efficacy at a lowered dosage level and long duration time as compared with the known quinone compounds. The compound of the general formula (I) where $R^4$ is a functional group containing an imidazole group exhibits specific double inhibitory effects on 5-lipoxygenase and thromboxane synthetase simultaneously, and is favorable for the application as a cardiovascular drug.

The compound (II) can be produced by either of the methods to be described below. The compound (IIa) can be obtained by allowing a compound of the general formula:

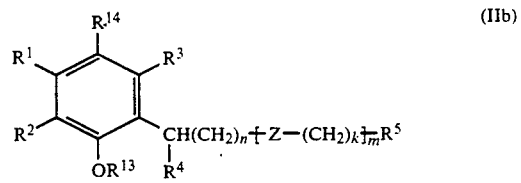

(wherein $R^1$, $R^2$, $R^3$, $R^4$, $R^5$, Z, m and n are as defined hereinbefore; $R^{13}$ is methyl, a methoxymethyl, benzyl or 2-tetrahydropyranyl group; $R^{14}$ is a hydrogen atom, or a methoxy, methoxymethyloxy, benzyloxy or 2-tetrahydropyranyloxy group) to undergo acid hydrolysis or catalytic reduction known per se to conduct deprotection.

Out of the compounds (II), a compound of the general formula:

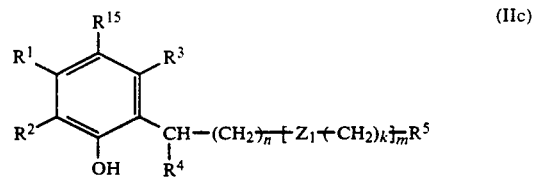

(wherein $R^1$, $R^2$, $R^3$, $R^4$, $R^5$, k, m and n are as defined hereinbefore; $R^{15}$ is a hydrogen atom or a hydroxyl group;

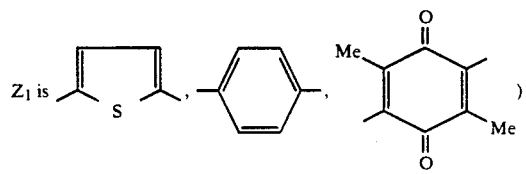

can be formed by allowing a compound of the general formula:

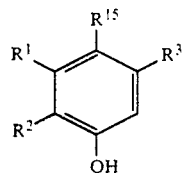

(III)

(wherein each of the symbols is as defined hereinbefore) and a compound of the general formula:

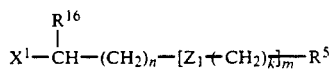

(IV)

(wherein k, m, n, $R^5$ and $Z_1$ are as defined hereinbefore; $X^1$ is a hydroxyl, acetoxy or lower alkoxy group or a halogen atom; $R^{16}$ is a group represented by $R^4$ or a methoxy group) to undergo condensation in the presence of an acid catalyst. Out of the compounds (IIc), a compound of the formula (IIc) where $R^5$ is a carboxyl group can also be obtained by allowing the compound (III) and a compound of the general formula:

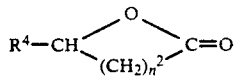

(V)

(wherein $R^4$ is as defined hereinbefore; $n^2$ is 2 or 3) to undergo condensation in the presence of an acid catalyst. This condensation reaction is carried out in a nonpolar solvent (e.g., methylene chloride, chloroform, benzene, toluene, isopropyl ether, 1,2-dichloroethane, 1,1,2,2-tetrachloroethane) in the presence of an acid catalyst (e.g., boron trifluoride ethyl etherate, aluminum chloride, stannic chloride p-toluenesulfonic acid, D-camphorsulfonic acid, etc.) in the temperature range of 10° to 100° C.

Since this condensation reaction depends upon the solubility in solvent of the compound (III) and the reactivity of the acid catalyst with the compound (IV) or (V), the reaction catalyst needs to be changed suitably according to the combination of the compounds (III) and (IV) or (V). The amount of the acid catalyst to be used is in the range of about 1/20 to 3.0 moles to the compound (III). This reaction is carried out preferably under oxygen-free conditions. The reaction under oxygen-free conditions yields the phenolic or hydroquinone compound (IIc).

The compound (IIb) can be produced by halogenating a compound of the general formula:

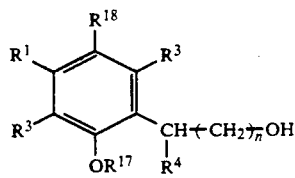

(IId)

(wherein $R^1$, $R^2$, $R^3$, $R^4$ and n are as defined hereinbefore; $R^{17}$ is a methyl, benzyl, 2-tetrahydropyranyl or methoxymethyl group; $R^{18}$ is a hydrogen atom or a methoxy, benzyloxy, 2-tetrahydropyranyloxy or methoxymethyloxy group) to give a compound of the general formula:

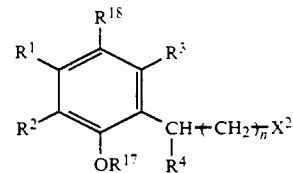

(VI)

(wherein $R^1$, $R^2$, $R^3$, $R^4$, $R^{17}$, $R^{18}$ and n are as defined hereinbefore; $X^2$ is a halogen atom), followed by condensation with a compound of the general formula:

$$H+Z_2-(CH_2)\overline{km}-Y^1$$ (VII)

(wherein k and m are as defined hereinbefore; $Y^1$ is a hydrogen atom or a hydroxyl, carboxyl, alkoxycarbonyl or 2-tetrahydropyranyloxy group; $Z_2$ is $-C{\equiv}C-$ and

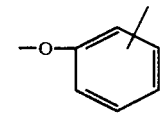

in the presence of of a base. With reference to this condensation reaction, the reaction conditions to be adopted vary with Z in the compound (VII). In the case of Z being $-C{\equiv}C-$ group, for example, n-butyllithium, sodium hydride, potassium hydride, sodium amide, etc. are used as a basic reagent. In the case of Z is

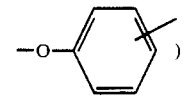

group, on the other hand, potassium carbonate, sodium hydroxide, sodium hydride, etc. are used.

A compound of the general formula (II) where Z is

and k is 0, with $R^5$ being a carboxyl or alkoxycarbonyl group, can also be produced by allowing the compound (VI) and an isobutyrate to undergo condensation in the presence of a base. In such a case, lithiumisopropylamide is preferably used as a base. This reaction is carried out in an anhydrous solvent (e.g., diethyl ether, tetrahydrofuran) under an atmosphere of inert gas (e.g., argon, helium, nitrogen) in the temperature range of −40° C. to 30° C.

The compound (IId) can be produced by subjecting the phenolic or hydroquinone hydroxyl group of the compound (IIc) to either of methylation, benzylation, 2-tetrahydropyranylation or methoxymethylation reaction, followed by a per se conventional and known reductive alcoholation reaction with lithium aluminum hydride.

Also, the compound (IId) can be produced by reacting a compound of the general formula:

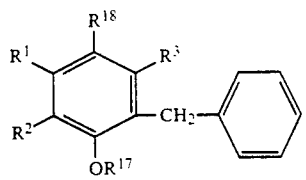
(VIII)

(wherein $R^1$, $R^2$, $R^3$, $R^{17}$ and $R^{18}$ are as defined hereinbefore) with a compound of the general formula:

(IX)

(wherein $X^2$ and n are as defined hereinbefore; $Y^2$ is a hydrogen atom, a hydroxyl, 2-tetrahydropyranyloxy or carboxyl group or a group represented by —C(CH$_3$)$_2$COOH).

The reaction of the compound (VIII) with the compound (IX), which comprises converting the methylene group of the benzyl group into an anion in the presence of a strong base (e.g., n-butyllithium, methyllithium, lithium diisopropylamide, etc.), followed by reaction with an ω-halogenoalkyl derivative (IX), yields the compound (IId). This reaction is carried out in anhydrous tetrahydrofuran, diethyl ether, or 1,2-dimethoxyethane in the presence of tetramethylethylenediamine in the temperature range of 0° C. to 70° C. The preferred reaction temperature conditions are in the range of room temperature to 65° C.

A compound (IIb-1), which consists of the compound (IIb) where $R^4$ is a methyl group and m is 0, can be produced by the per se known reaction.

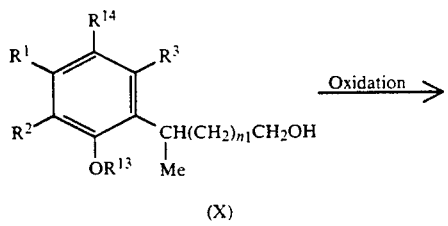
(X)

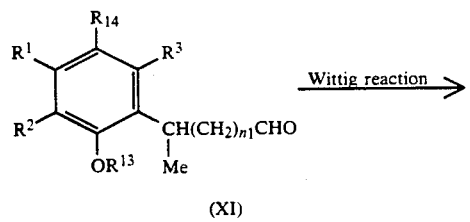
(XI)

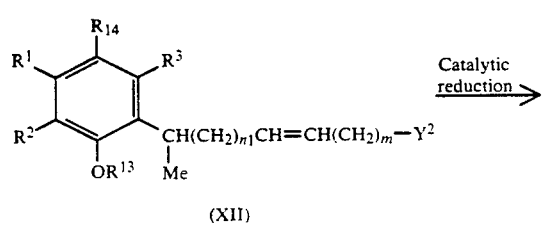
(XII)

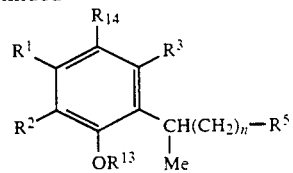
(IIb-1)

(wherein $R^1$, $R^2$, $R^3$, $R^{13}$, $R^{14}$, m, n, $Y^2$ and $R^5$ are as defined hereinbefore); $n_1$ is an integer of 1 to 5).

EXAMPLE 1

(Compound No. 1)

D-Camphor-10-sulfonic acid (0.1 g) was added to a toluene solution (50 ml) of 2,3,5-trimethylhydroquinone (3.1 g, 0.02 mole) and ethyl 6-acetoxy-6-(2-thienyl)hexanoate (5.6 g, 0.02 mole), and the mixture was heated at 60° C. for 6.5 hours, with stirring. After cooling, ethanol (100 ml) and a 10% aqueous solution (20 ml) of ferric chloride were added to the reaction solution, followed by stirring for 10 minutes. The reaction product was extracted with isopropyl ether, and the organic layer was washed with water, dried (over magnesium sulfate) and concentrated under reduced pressure. The residue was chromatographed on a silica gel column, and elution was performed with isopropyl etherhexane (1:1) to give ethyl 6-(3,5,6-trimethyl-1,4-benzoquinon-2-yl)-6-(2-thienyl)hexanoate (5.6 g, 76%). Its typical physical properties and nuclear magnetic resonance spectrum data are shown in Table 1. By following the procedure of this Example, the Compound Nos. 2 to 8 were prepared.

EXAMPLE 2

(Compound No. 9)

2,3,5-Trimethylhydroquinone (3.1 g, 0.02 mole) and 8-acetoxy-8-phenyloctanoic acid (6.0 g, 0.021 mole) were added to toluene (80 ml), and boron trifluoride ethyl etherate (0.3 ml) was added dropwise to the mixture at room temperature, with stirring. The reaction solution was stirred at room temperature for 4 days, and then the solvent was distilled off under reduced pressure. The residue was dissolved in tetrahydrofuran (50 ml), and a 10% aqueous solution of ferric chloride was added to the solution to conduct oxidation to the quinone derivative. The reaction product was extracted twice with ethyl acetate, and the organic layer was washed with water, dried and concentrated under reduced pressure. The resulting crude product was chromatographed on a silica gel column, followed by elution with isopropyl ether, and the quinone derivative was recrystallized from isopropyl ether to give 8-phenyl-8-(3,5,6-trimethyl-1,4-benzoquinon -2-yl)octanoic acid (5.8 g, 78%). Its typical physical properties and nuclear magnetic resonance spectrum data are shown in Table 1. By following the procedure of this Example, the Compound Nos. 10 to 19, 50 and 51 were prepared.

EXAMPLE 3

(Compound No. 20)

D-Camphor-10-sulfonic acid (0.1 g) was added to a toluene solution (50 ml) of 2-methyl-1,4-naphthohydroquinone (3.6 g, 0.02 mole) and 6-ethoxy-6-(4-methoxyphenyl)hexanoic acid (5.6 g, 0.021 mole), and the mixture was heated at 60° C. for 18 hours, with stirring. After cooling, the solvent was distilled off under reduced pressure, and then tetrahydrofuran (20 ml) was added to the residue. A 10% aqueous solution of ferric chloride was added to the solution, followed by stirring for 10 minutes, and the reaction product was extracted with ethyl acetate. The organic layer was washed with water, dried and concentrated under reduced pressure. The residue was chromatographed on a silica gel column, and elution was effected with isopropyl ether to give 6-(3-methyl-1,4-naphthoquinon -2-yl)-6-(4-methoxyphenyl)hexanoic acid (3.5 g, 45%). This product was recrystallized from isopropyl ether. Its typical physical properties and nuclear magnetic resonance spectrum data are shown in Table 1. By following the procedure of this Example, the Compound No. 21 was prepared.

EXAMPLE 4

(Compound No. 22)

D-Camphor-10-sulfonic acid (0.1 g) was added to a toluene solution (60 ml) of 2,3,5-trimethylhydroquinone (3.1 g, 0.02 mole) and 6-hydroxy-6-(4-methoxyphenyl)-hexanoic acid (5.0 g, 0.021 mole), and the mixture was heated at 70° C. for 20 hours, with stirring. The reaction solution was evaporated under reduced pressure, and tetrahydrofuran (50 ml) was added to dissolve the residue, followed by adding furthermore a 10% aqueous solution of ferric chloride and stirring at room temperature for 10 minutes. The reaction product was extracted with ethyl acetate, and the organic layer was washed with water, dried and then concentrated under reduced pressure. The residue was chromatographed on a silica gel column, and elution was performed with isopropyl ether to give 6-(3,5,6-trimethyl-1,4-benzoquinon -2-yl)-6-(4-methoxyphenyl)hexanoic acid (5.1 g, 76%). Its typical physical properties and nuclear magnetic resonance spectrum data are shown in Table 1. By following the procedure of this Example, the Compound Nos. 23 to 34 and 68 were prepared.

EXAMPLE 5

Aluminum chloride (0.7 g, 5.2 mmole was added to a 1,2-dichloroethane solution (20 ml) of hydroquinone (0.5 g, 4.5 mmole) and 4-phenylbutyllactone (0.8 g, 4.9 mmole), and the mixture was heated at 60° C. for 3 hours with stirring. After cooling, 2N-hydrochloric acid (40 ml) was added to the reaction solution, followed by stirring for 10 minutes. The reaction solution was subjected to extraction with ethyl acetate, and the organic layer was washed with water, dried and evaporated. The residue was chromatographed on a silica gel column, and elution was performed with isopropyl ether-ethyl acetate (1:1) to give 4-phenyl-4-(1,4-dihydroxy-2-phenyl)butyric acid (0.6 g, 49%), an oily substance. Nuclear magnetic resonance spectrum: δ 2.43(4H), 4.24(1H), 6.60(3H), 7.30(5H).

EXAMPLE 6

(Compound No. 35)

Aluminum chloride (1.4 g, 0.01 mole) was added to a 1,2-dichloroethane solution (20 ml) of 2,3,5-trimethylhydroquinone (1.5 g, 0.01 mole) and the mixture was heated at 80° C. A 1,2-dichloroethane solution (10 ml) of 4-phenylbutyrolactone (1.6 g, 0.01 mole) was added dropwise to the mixed solution over the 2-hours period, and the reaction was carried out under the same conditions for further 18 hours. After cooling, 2N-hydrochloric acid (40 ml) was added to the reaction solution, followed by stirring for 10 minutes, and the reaction product was extracted with isopropyl ether. The organic layer was washed with water, dried and evaporated and the residue was dissolved in tetrahydrofuran (30 ml). A 10% aqueous solution (5 ml) of ferric chloride was added to the solution, followed by stirring at room temperature for 10 minutes, and the reaction product was extracted twice with ethyl acetate. The organic layer was washed with water, dried and concentrated under reduced pressure, and the residue was chromatographed on a silica gel column, followed by elution with isopropyl ether to give 4-(3,5,6-trimethyl-1,4-benzoquinon -2-yl)-4-phenylbutyric acid (1.2 g, 38%). Its typical physical properties and nuclear magnetic resonance spectrum data are shown in Table 1. By following the procedure of this Example, the Compound Nos. 36 to 38 were prepared.

EXAMPLE 7

(Compound NO. 40)

Boron trifluoride diethyl etherate (0.25 ml) was added dropwise to a toluene solution (80 ml) of 2,3-dimethoxy-6-methyl-1,4-hydroquinone (5.5 g, 0.03 mole) and 5-phenyl-5-valerolactone (5.3 g, 0.03 mole) at room temperature, and the reaction solution was stirred at 50° C. for 20 hours and then concentrated under reduced pressure. The residue was dissolved in tetrahydrofuran (20 ml), and a 10% aqueous solution (10 ml) of ferric chloride was added to the solution, followed by stirring for 10 minutes. The reaction product was extracted with ethyl acetate, and the organic layer was washed with water, dried and concentrated under reduced pressure. The residue was chromatographed on a silica gel column, and elution was performed with isopropyl ether to give 5-(5,6-dimethoxy-3-methyl-1,4-benzoquinon -2-yl)-5-phenylbutyric acid (6.5 g, 57%). This product was recrystallized from isopropyl ether-ethyl acetate. Its typical physical properties and nuclear magnetic resonance spectrum data are shown in Table 1. By following the procedure of this Example, the Compound No. 39 was prepared.

EXAMPLE 8

(Compound No. 41)

4-Phenyl-4-(3,5,6-trimethyl-1,4-benzoquinon -2-yl)butanoic acid (1.2 g) was dissolved in ethanol (50 ml), and thionyl chloride (0.4 ml) was added to the solution, followed by stirring at room temperature for 4 hours. After the reaction solution was concentrated under reduced pressure, the resulting residue was dissolved in isopropyl ether, and the organic layer was washed with water, dried and concentrated under reduced pressure. The residue was chromatographed on a silica gel column, and the object compound was eluted with isopropyl ether to give ethyl 4-phenyl-4-(3,5,6-trimethyl-1,4-benzoquinon -2-yl)butanoate (1.1 g, 84%). Its typical physical properties and nuclear magnetic resonance spectrum data are shown in Table 1. By following the procedure of this example, the Compound No. 42 was prepared.

EXAMPLE 9

(Compound No. 43)

Boron trifluoride diethyl ether (0.5 ml) was added to a toluene solution (100 ml) of 2-methyl-1,4-hydronaphthoquinone (3.5 g, 20 mmole) and 1,6-diacetoxyhexylbenzene (6.0 g, 21 mmole), and the mixture was stirred at 60° C. for 20 hours. After the solvent was distilled off, the residue was dissolved in tetrahydrofuran (50 ml), and a 10% aqueous solution of ferric chloride was added to the solution to conduct the reaction at room temperature for 10 minutes. The reaction product was extracted with ethyl acetate, and the organic layer was washed with water, dried and concentrated under reduced pressure. The residue was chromatographed on a silica gel column, and elution was carried out with isopropyl ether-ethyl acetate (1:1) to give 6-acetoxy-1-(3-methyl-1,4-naphthoquinon -2-yl)-1-phenylhexane (3.0 g, 38%). Its typical physical properties and nuclear magnetic resonance spectrum data are shown in Table 1. By following the procedure of this Example, the Compound No. 44 was prepared.

EXAMPLE 10

(Compound No. 45)

7-(2,5-Dimethoxy-3,4,6-trimethylphenyl)-7-phenylheptanol (1.85 g, 5.0 mmole) was dissolved in a mixed solution of acetonitrile (12 ml) and water (6 ml), and a cooled solution of ceric ammonium nitrate (8.22 g, 5×3 mmole) in 50% aqueous acetonitrile (16 ml) was added dropwise to the solution, under ice cooling, over the 20-minutes period. After stirring was continued for another 20 minutes under ice cooling, acetonitrile was distilled off under reduced pressure, and isopropyl ether was added to the residue to conduct extraction. The isopropyl ether layer was separated out, washed with aqueous sodium chloride solution, dried (magnesium sulfate), and evaporated. The residual solution was chromatographed on a silica gel column, and purification was performed (elution with isopropyl ether) to give 7-(3,5,6-trimethyl-1,4-benzoquinon -2-yl)-7-phenylheptanol (1.53 g, 90%). Its typical physical properties and nuclear magnetic resonance spectrum data are shown in Table 1. By following the procedure of this Example, the Compound Nos. 9, 10, 35, 36, 46 to 55 and 64 to 67 were prepared.

EXAMPLE 11

(Compound No. 56)

A solvent mixture of acetonitrile (12 ml) and water (6 ml) was added to 2.01 g (5.0 mmole) of 7-(2,3,4,5-tetramethoxy-6-methylphenyl)-7-phenylheptanol and 2.51 g (5×3 mmole) of 2,6-pyridinecarboxylic acid, and a cooled solution of 8.22 g (5×3 mmole) of ceric ammonium nitrate in 50% aqueous acetonitrile (16 ml) was added dropwise to the mixture over the 20 minutes period under ice-cooling. After stirring was continued for another 20 minutes under ice-cooling, the insoluble matter was filtered out, and the acetonitrile was distilled off under reduced pressure. Isopropyl ether was added to the residue to carry out extraction. The isopropyl ether layer was separated out, washed with aqeuous sodium chloride solution, dried (magnesium sulfate) and evaporated. The residue was chromatographed on a silica gel column to elute with isopropyl ether/ethyl acetate to give 1.56 g (84%) of 7-(5,6-dimethoxy-3-methyl-1,4-benzoquinon -2-yl)-7-phenylheptanol. Its typical physical properties and nuclear magnetic resonance spectrum data are shown in Table 1. By following the procedure of this Example, the Compound No. 57 was prepared.

EXAMPLE 12

(Compound No. 58)

Toluene (10 ml) was added to 1.20 g (3.68 mmole) of 6-(3,5,6-trimethyl-1,4-benzoquinon -2-yl)-6-phenylhexanol and 0.90 g (3.68×3 mmole) of potassium cyanate, followed by stirring at room temperature, and 1.38 g (3.68×3.3 mmole) of trifluoroacetic acid was added to the mixture over the 5-minutes period. 5 Minutes later, the reaction temperature was raised to 40° C., and stirring was effected at 35° to 40° C. for 3 hours. After water was added, the insoluble matter was filtered out, and isopropyl ether was added to the filtrate to effect extraction. The organic layer was separated out, washed with aqueous sodium chloride solution, dried (magnesium sulfate) and evaporated. The residue was chromatographed on a silica gel column to elute with isopropyl ether to give 0.79 g (58%, recrystallized from isopropyl ether) of 6-(3,5,6-trimethyl-1,4-benzoquinon -2-yl)-6-phenylhexyl carbamate. Its typical physical properties and nuclear magnetic resonance spectrum data are shown in Table 1. By following the procedure of this Example, the Compound NO. 59 was prepared.

EXAMPLE 13

(Ccompound No. 60)

A 35 μl (3×1/10 mmole) portion of stannic chloride was added to a solution of 6-(3,5,6-trimethyl-1,4-benzoquinon-2-yl)-6-phenylhexanol (0.98 g, 3.0 mmole) and methyl isocyanate (0.17 g, 3.0 mmole) in dichloromethane (10 ml) at room temperature, and the mixture was stirred for 30 minutes. By adding ice-cold water, the reaction was suspended, and extraction was effected. The dichloromethane layer was separated out, washed with aqueous sodium chloride solution, dried (magnesium sulfate) and evaporated. The residue was chromatographed on a silica gel column to elute with isopropyl ether to give 1.09 g (95%, recrystallized from isopropyl ether) of N-methyl 6-(3,5,6-trimethyl-1,4-benzoquinon -2-yl)-6-phenylhexyl carbamate. Its typical physical properties and nuclear magnetic resonance spectrum data are shown in Table 1. By following the procedure of this Example, the Compound No. 61 was prepared.

EXAMPLE 14

(Compound NO. 62)

Rindler catalyst (90 mg) and quinoline (15 μl) were added to a solution of 7-(3,5,6-trimethyl-1,4-benzoquinon 2-yl)-7-phenyl-2-heptyn -1-ol (1.01 g, 3.0 mmole) in ethyl acetate (20 ml), and catalytic reduction was carried out at room temperature. 3 Hours later, when absorption (73 ml) of hydrogen was almost stopped, the reaction was suspended and the catalyst was filtered out. The ethyl acetate was distilled off under reduced pressure, and the residue was chromatographed on a silica gel column to elute with isopropayl ether to give (Z)-7-(3,5,6-trimethyl-1,4-benzoquinon -2-yl)-7-phenyl-2-hepten -1-ol (0.95 g, 94%). Its typical physical properties and nuclear magnetic resonance spectrum data are shown in Table 1.

EXAMPLE 15

(Compound No. 52)

Jones' reagent (2.25 ml) was added dropwise to a solution of 7-(3,5,6-trimethyl-1,4-benzoquinon -2-yl)-7- phenyl-2-heptyne-1-ol (1.01 g, 3.0 mmole) in acetone (15 ml) at room temperature over the 15-minutes period. The mixture was stirred at room temperature for another 30 minutes and the acetone was distilled off under reduced pressure. Isopropyl ether and water were added to the residue, and extraction was effected. The isopropyl ether layer was separated out, washed with aqueous sodium chloride solution, dried (magnesium sulfate) and evaporated. The residue was recrystallized from isopropyl ether to give 7-(3,5,6-trimethyl-1,4-benzoquinon -2-yl)-7-phenyl-2-heptynoic acid (0.71 g, 68%).

Its typical physical properties and nuclear magnetic resonance spectrum data are shown in Table 1.

EXAMPLE 16

(Compound No. 63)

To a solution of 0.92 g (2.0 mmole) of 4-[7-(3,5,6-trimethyl-1,4-benzoquinon -2-yl)-7-phenylheptoxy]benzoic acid in dichloromethane (10 ml) were added 0.44 ml (2×3 mmole) of thionyl chloride and dimethylformamide (8 µl),and the mixture was stirred at 40° C. for 1 hour. The solvent was distilled off, and the residue was dissolved in tetrahydrofuran (10 ml), followed by ice-cooling. After 0.21 g (2×1.5 mmole) of hydroxylamine hydrochloride was added, a solution of 0.34 g (2×2 mmole) of sodium hydrogencarbonate in water (5 ml) was added to the reaction mixture, followed by stirring for 15 minutes under ice-cooling. The tetrahydrofuran was distilled off under reduced pressure, and ethyl acetate was added to the residue to conduct extraction. The ethyl acetate layer was separated out, washed with aqueous sodium chloride solution, dried (magnesium sulfate) and evaporated. The residue was chromatographed on a silica gel column to elute with ethyl acetate to give 4-[7-(3,5,6-trimethyl-1,4-benzoquinon -2-yl)-7-phenylheptoxy]benzohydroxamic acid (0.86 g, 91%).

Its typical physical properties and nuclear magnetic resonance spectrum data are shown in Table 1.

EXAMPLE 17

(Compound No. 68)

6N Hydrochloric acid (10 ml) was added to a solution of ethyl 6-(3,5,6-trimethyl-1,4-benzoquinon -2-yl)-6-(2-thienyl)hexanoate (1.7 g, 4.5 mmole) in tetrahydrofuran (10 ml), followed by stirring for 17 hours with heating at 70° C. After cooling, isopropyl ether was added to the mixture, and the organic layer was washed twice with water, dried and concentrated under reduced pressure. The residue was chromatographed on a silica gel column, and elution was performed with isopropyl ether-ethyl acetate (1:1), followed by recrytallization from isopropyl ether to give 6-(3,5,6-trimethyl-1,4-benzoquinon -2-yl)-6-(2-thienyl)hexanoic acid (1.1 g, 70%).

Its typical physical properties and nuclear magnetic resonance spectrum data are shown in Table 1.

EXAMPLE 18

(Compound No. 73)

Lithium aluminum hydride (1.0 g, 27 mmole) was added to a tetrahydrofuran solution (50 ml) containing methyl 10-(3,5,6-trimethyl-1,4-benzoquinon -2-yl)-10-phenyldecanoate, (2.4 g, 6 mmole), followed by stirring for 3 hours with heating at 60° C. After the reaction solution was cooled, water was added to suspend the reaction, and 2N hydrochloric acid was added to adjust to pH 4.0. A 10% aqueous solution of ferric chloride (5 ml) was added to the mixture, and the reaction was allowed to proceed at room temperature for 10 minutes. Ethyl acetate was added to the reaction solution, and extraction was effected. The organic layer was washed with water, dried and concentrated under reduced pressure, and the residue was chromatographed on a silica gel column, followed by elution with isopropyl ether-ethyl acetate (1:1) to give 10-(3,5,6-trimethyl-1,4-benzoquinon-2-yl)-10-phenyldecan-1-ol (2.0 g). Its typical physical properties and nuclear magnetic resonance spectrum data are shown in Table 1. By following the procedure of this Example, the Compound Nos. 74 to 84 were prepared.

EXAMPLE 19

(Compound No. 69)

Thionyl chloride (2 ml) was added to a 1,2-dichloroethane (10 ml) solution containing 6-(3,5,6-trimethyl-1,4-benzoquinon -2-yl)-6-phenylhexanoic acid (0.7 g, 2 mmole), followed by stirring at 60° C. for 1 hour. The reaction solution was concentrated under reduced pressure, and the residue was dissolved in 1,2-dichloroethane (20 ml). Hydroxylamine hydrochloride (0.5 g) and then aqueous saturated solution (20 ml) of sodium hydrogencarbonate were added to the solution, followed by stirring at room temperature for 1 hour. Ethyl acetate was added to the reaction solution to extract the reaction product, and the organic layer was washed with water, dried and evaporated. The resulting residue was chromatographed on a silica gel column, and elution was performed with isopropyl ether-ethyl acetate (1:1), followed by recrystallization of the object compound from isopropyl ether-ethyl acetate (1:1) to give 6-(3,5,6-trimethyl-1,4-benzoquinon -2-yl)-6-phenylhexanehydroxamic acid (0.7 g, 96%). Its typical physical properties and nuclear magnetic resonance spectrum data are shown in Table 1. By following the procedure of this Example, the Compound Nos. 70 to 72 were prepared.

EXAMPLE 20

(Compound No. 77)

6N Hydrochloric acid (20 ml) was added to a tetrahydrofuran solution (20 ml) containing 1-acetoxy-6-(3-methyl-1,4-naphthoquinon -2-yl)-6-phenylhexane (2.8 g, 7.2 mmole), followed by stirring for 5 hours with heating at 70° C. After cooling, ethyl acetate was added to the reaction solution, and the organic layer was separated out, washed with water, dried and evaporated under reduced pressure. The residue was chromatographed on a silica gel column, and elution was performed with isopropyl ether-ethyl acetate (1:1), followed by recrystallization of the object compound from isopropyl ether to give 1-hydroxy-6-(3-methyl-1,4-naphthoquinon -2-yl)-6-phenylhexane (2.1 g). Its typical physical properties and nuclear magnetic resonance spectrum data are shown in Table 1. By following the procedure of this Example, the Compound Nos. 75, 79 and 81 were prepared.

Shown below in Table 1 are typical physical properties and nuclear magnetic resonance spectra of the compounds prepared in accordance with the procedure of the above examples. Melting points were uncorrected.

TABLE 1

$$\text{structure: quinone with } R^1, R^2 \text{ substituents, Me group, and } CH(R^4)-(CH_2)_n-R^5 \text{ side chain}$$

| Compound No. | Prepared by the procedure by Example | $R^1$ | $R^2$ | $R^4$ | $R^5$ | n | Molecular formula | Melting point (°C.) Physical properties | Nuclear magnetic resonance spectrum, δ value (ppm), TMS as internal standard |
|---|---|---|---|---|---|---|---|---|---|
| 1 | 1 | Me | Me | (thienyl) | COOEt | 4 | $C_{21}H_{26}O_4S$ | oil | 1.21(3H, t), 1.10–1.80(4H, m), 2.00(6H, s), 2.07(3H, s), 2.00–2.40(4H, m), 4.09(2H, q), 4.47(1H, t), 6.89(2H, m), 7.12(1H, m) |
| 2 | 1 | Me | Me | (phenyl) | COOEt | 4 | $C_{23}H_{28}O_4$ | oil | 1.20(3H, t), 1.10–1.80(4H, m), 1.95(3H, s), 1.97(3H, s), 2.04(3H, s), 2.00–2.40(4H, m), 4.09(2H, q), 4.29(1H, t), 7.24(5H, m) |
| 3 | 1 | —CH=CH— CH=CH— | | (thienyl) | COOEt | 4 | $C_{23}H_{24}O_4S$ | 37–38 | 1.19(3H, t), 1.10–1.80(4H, m), 2.22(3H, s), 2.00–2.40(4H, m), 4.07(2H, q), 4.65(1H, t), 6.95(2H, m), 7.13(1H, m), 7.70(2H, m), 8.01(2H, m) |
| 4 | 1 | Me | Me | (phenyl) | COOMe | 8 | $C_{26}H_{34}O_4$ | oil | 1.10–1.80(12H, m), 1.97(6H, s), 2.04(3H, s), 2.00–2.40(4H, m), 3.64(3H, s), 4.29(1H, t), 7.24(5H, m) |
| 5 | 1 | —CH=CH— CH=CH— | | (phenyl) | COOEt | 4 | $C_{25}H_{26}O_4$ | oil | 1.18(3H, t), 1.10–1.80(4H, m), 2.20(3H, s), 2.00–2.40(4H, m), 4.07(2H, q), 4.48(1H, t), 7.28(5H, m), 7.66(2H, m), 8.05(2H, m) |
| 6 | 1 | MeO | MeO | (thienyl) | COOEt | 4 | $C_{21}H_{26}O_6S$ | oil | 1.21(3H, t), 1.10–1.80(4H, m), 2.03(3H, s), 2.00–2.30(4H, m), 3.96(6H, s), 4.08(2H, q), 4.45(1H, t), 6.81(2H, m), 7.12(1H, m) |
| 7 | 1 | MeO | MeO | (phenyl) | COOEt | 4 | $C_{23}H_{28}O_6$ | oil | 1.21(3H, t), 1.10–1.80(4H, m), 2.03(3H, s), 2.00–2.30(4H, m), 4.06(6H, s), 4.08(2H, q), 4.27(1H, t) |

TABLE 1-continued

Structure:

$$\begin{array}{c} \text{R}^1,\text{R}^2\text{-substituted 2-methyl-1,4-benzoquinone with } -\text{CH}(\text{R}^4)-(\text{CH}_2)_n-\text{R}^5 \end{array}$$

| Compound No. | Prepared by the procedure by Example | R¹ | R² | R⁴ | R⁵ | n | Molecular formula | Melting point (°C) Physical properties | Nuclear magnetic resonance spectrum, δ value (ppm), TMS as internal standard |
|---|---|---|---|---|---|---|---|---|---|
| 8 | 1 | MeO | MeO | phenyl | COOMe | 8 | $C_{26}H_{34}O_6$ | oil | 1.10–1.80(12H, m), 2.02(3H, s), 2.00–2.40(4H, m), 3.64(3H, s), 4.01(6H, s), 4.27(1H, t), 7.24(5H, m) |
| 9 | 2,10 | Me | Me | phenyl | COOH | 6 | $C_{23}H_{28}O_4$ | 94–98 | 1.10–1.80(8H, m), 1.97(6H, s), 2.00–2.40(2H, m), 2.04(3H), 2.31(2H), 4.29(1H, t), 7.24(5H, m), 10.9(1H) |
| 10 | 2,10 | Me | Me | phenyl | COOH | 4 | $C_{21}H_{24}O_4$ | 125–126 | 1.10–1.60(2H), 1.67(2H), 1.97(6H), 2.0–2.4(2H), 2.04(3H), 2.33(2H), 4.30(1H), 7.24(5H), 10.7(1H) |
| 11 | 2 | Me | Me | phenyl | COOH | 8 | $C_{25}H_{32}O_4$ | 48–50 | 1.10–1.80(12H, m), 1.96(6H, s), 2.04(3H, s), 2.00–2.40(4H, m), 4.29(1H, t), 7.24(5H, m) |
| 12 | 2 | —CH=CH—CH=CH— | | phenyl | COOH | 4 | $C_{23}H_{22}O_4$ | 169–170 | 1.10–1.80(4H, m), 2.21(3H, s), 2.00–2.40(4H, m), 4.48(1H, t), 7.24(5H, m), 7.64(2H, m), 8.03(2H, m) |
| 13 | 2 | —CH=CH—CH=CH— | | thienyl | COOH | 4 | $C_{21}H_{20}O_4S$ | 159–160 | 1.00–1.80(4H, m), 2.22(3H, s), 2.00–2.40(4H, m), 4.65(1H, t), 6.92(2H, m), 7.15(1H, m), 7.67(2H, m), 8.07(2H, m) |
| 14 | 2 | —CH=CH—CH=CH— | | phenyl | COOH | 6 | $C_{25}H_{26}O_4$ | 99–100 | 1.10–1.80(8H, m), 2.19(3H, s), 2.00–2.40(4H, m), 4.48(1H, t), 7.25(5H, m), 7.65(2H, m), 8.02(2H, m) |

TABLE 1-continued

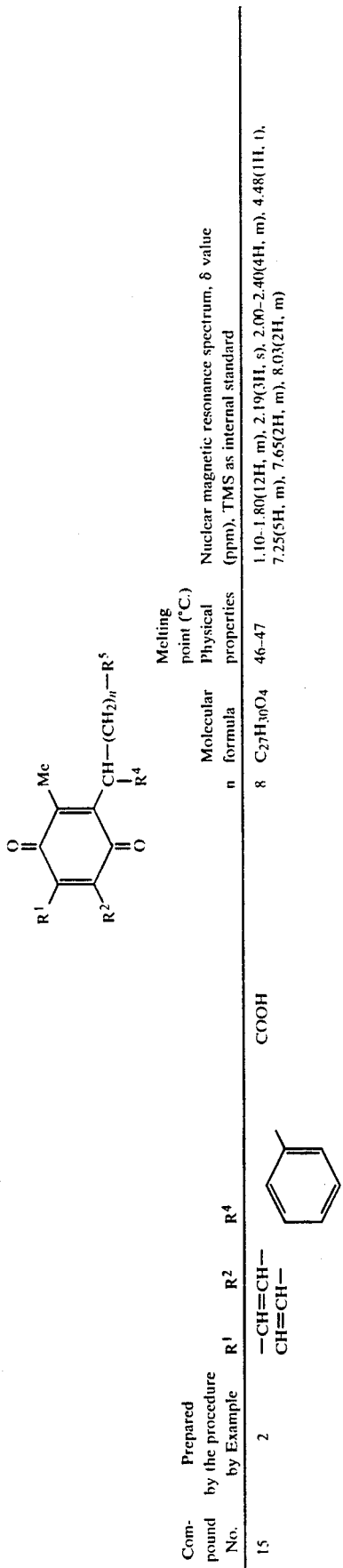

| Compound No. | Prepared by the procedure by Example | R¹ | R² | R⁴ | R⁵ | n | Molecular formula | Melting point (°C.) Physical properties | Nuclear magnetic resonance spectrum, δ value (ppm), TMS as internal standard |
|---|---|---|---|---|---|---|---|---|---|
| 15 | 2 | —CH=CH—CH=CH— | | (phenyl) | COOH | 8 | $C_{27}H_{30}O_4$ | 46-47 | 1.10-1.80(12H, m), 2.19(3H, s), 2.00-2.40(4H, m), 4.48(1H, t), 7.25(5H, m), 7.65(2H, m), 8.03(2H, m) |
| 16 | 2 | MeO | MeO | (phenyl) | COOH | 4 | $C_{21}H_{24}O_6$ | 73-74 | 1.30-1.90(4H, m), 2.02(3H, s), 2.00-2.40(4H, m), 3.94(6H, s), 4.27(1H, t), 7.24(5H, m) |
| 17 | 2 | MeO | MeO | (thienyl) | COOH | 4 | $C_{19}H_{22}O_6S$ | 51-52 | 1.10-1.80(4H, m), 2.04(3H, s), 2.00-2.40(4H, m), 3.97(6H, s), 4.45(1H, t), 6.85(2H, m), 7.12(1H, m) |
| 18 | 2 | MeO | MeO | (phenyl) | COOH | 6 | $C_{23}H_{28}O_6$ | 79-80 | 1.10-1.80(8H, m), 2.02(3H, s), 2.00-2.40(4H, m), 3.94(6H, s), 4.25(1H, t), 7.25(5H, m) |
| 19 | 2 | MeO | MeO | (phenyl) | COOH | 8 | $C_{25}H_{32}O_6$ | 49-50 | 1.10-2.00(12H, m), 2.01(3H, s), 2.00-2.40(4H, m), 3.94(6H, s), 4.26(1H, t), 7.24(5H, m) |
| 20 | 3 | —CH=CH—CH=CH— | | (4-methoxyphenyl) | COOH | 4 | $C_{24}H_{24}O_5$ | 55-56 | 1.10-1.80(4H, m), 2.21(3H, s), 2.00-2.40(4H, m), 3.75(3H, s), 4.40(1H, t), 6.80(2H, d), 7.23(2H, d), 7.63(2H, m), 8.03(2H, m) |

TABLE 1-continued

Structure:

$$\begin{array}{c} \text{R}^1, \text{R}^2 \text{ substituted quinone with Me and CH-(CH}_2)_n\text{-R}^5 / \text{R}^4 \text{ group} \end{array}$$

| Compound No. | Prepared by the procedure by Example | R¹ | R² | R⁴ | | n | Molecular formula | Melting point (°C.) Physical properties | Nuclear magnetic resonance spectrum, δ value (ppm), TMS as internal standard |
|---|---|---|---|---|---|---|---|---|---|
| 21 | 3 | Me | Me | 2-naphthyl | COOH | 5 | $C_{26}H_{28}O_4$ | 126-127 | 1.10-1.80(6H, m), 1.83(3H, s), 1.96(3H, s), 2.01(3H, s), 2.00-2.40(4H, m), 5.06(1H, t), 7.20-7.80(7H, m) |
| 22 | 4 | Me | Me | 4-methoxyphenyl | COOH | 4 | $C_{22}H_{26}O_5$ | 74-75 | 1.10-1.80(4H, m), 1.96(6H, s), 2.06(3H, s), 2.00-2.40(4H, m), 3.75(3H, s), 4.20(1H, t), 6.78(2H, d), 7.19(2H, d) |
| 23 | 4 | Me | Me | 4-methoxyphenyl | COOH | 5 | $C_{23}H_{28}O_4$ | 110-111 | 1.10-1.80(6H, m), 1.95(6H, s), 2.04(3H, s), 2.00-2.40(4H, m), 3.74(3H, s), 4.19(1H, t), 6.77(2H, d), 7.18(2H, d) |
| 24 | 4 | Me | Me | 5-indanyl | COOH | 5 | $C_{25}H_{30}O_4$ | 133-135 | 1.10-1.80(6H, m), 1.97(6H, s), 2.06(3H, s), 2.00-2.40(6H, m), 2.84(4H, m), 4.23(1H, t), 7.07(3H, m) |
| 25 | 4 | Me | Me | 5-indanyl | COOH | 6 | $C_{26}H_{32}O_4$ | oil | 1.10-1.80(8H, m), 1.96(6H, s), 2.06(3H, s), 2.00-2.40(6H, m), 2.85(4H, m), 4.23(1H, t), 7.08(3H, m) |

TABLE 1-continued

| Compound No. | Prepared by the procedure by Example | R¹ | R² | R⁴ | R⁵ | n | Molecular formula | Melting point (°C.) Physical properties | Nuclear magnetic resonance spectrum, δ value (ppm), TMS as internal standard |
|---|---|---|---|---|---|---|---|---|---|
| 26 | 4 | —CH=CH—CH=CH— | | 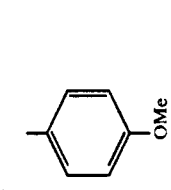 | COOH | 5 | C₂₅H₂₆O₅ | 144–145 | 1.10–1.80(6H, m), 2.21(3H, s), 2.00–2.40(4H, m), 3.76(3H, s), 4.39(1H, t), 6.79(2H, d), 7.24(2H, d), 7.59(2H, m), 8.06(2H, m) |
| 27 | 4 | —CH=CH—CH=CH— | | 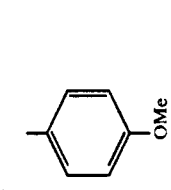 | COOH | 5 | C₂₈H₂₆O₄ | 163–164 | 1.10–1.80(6H, m), 1.96(3H, s), 2.00–2.40(4H, m), 5.26(1H, t), 7.00–8.00(11H, m) |
| 28 | 4 | —CH=CH—CH=CH— | | 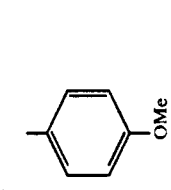 | COOH | 5 | C₂₇H₂₈O₄ | 121–122 | 1.10–1.80(6H, m), 1.90–2.40(4H, m), 2.20(3H, s), 2.83(4H, m), 4.41(1H, t), 7.07(3H, s), 7.66(2H, m), 8.04(2H, m) |
| 29 | 4 | —CH=CH—CH=CH— | | 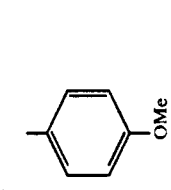 | COOH | 6 | C₂₈H₃₀O₄ | oil | 1.10–1.80(8H, m), 2.21(3H, s), 2.00–2.40(6H, m), 2.85(4H, m), 4.43(1H, t), 7.20(3H, m), 7.65(2H, m), 8.05(2H, m) |
| 30 | 4 | MeO | MeO | 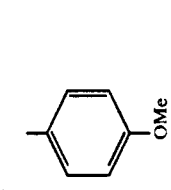 | COOH | 4 | C₂₂H₂₆O₇ | oil | 1.10–1.80(4H, m), 2.03(3H, s), 1.90–2.40(4H, m), 3.74(3H, s), 3.95(6H, s), 4.23(1H, t), 6.78(2H, d), 7.18(2H, d) |

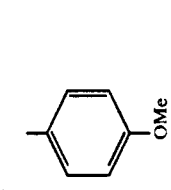

TABLE 1-continued

Structure:

$R^1, R^2$ substituted on a quinone ring with Me and $CH(R^4)-(CH_2)_n-R^5$ group.

| Compound No. | Prepared by the procedure by Example | $R^1$ | $R^2$ | $R^4$ | $R^5$ | n | Molecular formula | Melting point (°C.) Physical properties | Nuclear magnetic resonance spectrum, δ value (ppm), TMS as internal standard |
|---|---|---|---|---|---|---|---|---|---|
| 31 | 4 | MeO | MeO | phenyl | COOH | 5 | $C_{22}H_{26}O_6$ | 92-93 | 1.10-1.80(6H, m), 2.01(3H, m), 2.00-2.45(4H, m), 3.95(6H, s), 4.24(1H, t), 7.24(5H, m) |
| 32 | 4 | MeO | MeO | 5-methylindanyl | COOH | 6 | $C_{26}H_{32}O_6$ | oil | 1.10-1.80(8H, m), 1.90-2.20(4H, m), 2.04(3H, s), 2.31(2H, m), 2.85(4H, m), 3.99(6H, m), 4.22(1H, t), 7.09(3H, m) |
| 33 | 4 | Me | Me | 2,5-dimethylthienyl | COOH | 5 | $C_{21}H_{26}O_4S$ | 77-78 | 1.10-1.80(6H, m), 1.98(6H, s), 2.05(3H, s), 2.00-2.40(4H, m), 2.38(3H, s), 4.36(1H, t), 6.40-6.65(2H, m) |
| 34 | 4 | -CH=CH- | CH=CH- | 2,5-dimethylthienyl | COOH | 5 | $C_{22}H_{24}O_4S$ | 104-105 | 1.10-1.80(6H, m), 2.21(3H, s), 2.00-2.40(4H, m), 2.38(3H, s), 4.54(1H, t), 6.54(1H, m), 6.67(1H, m), 7.64(2H, m), 8.04(2H, m) |
| 35 | 6,10 | Me | Me | phenyl | COOH | 2 | $C_{19}H_{20}O_4$ | 142-143 | 1.96(6H), 2.06(3H), 2.38(2H), 2.52(2H), 4.35(1H), 7.26(5H), 8.10(1H) |
| 36 | 6,10 | Me | Me | phenyl | COOH | 3 | $C_{20}H_{22}O_4$ | 144-145 | 1.30-1.80(2H, m), 1.97(6H, s), 2.07(3H, s), 2.00-2.40(4H, m), 4.30(1H, t), 7.25(5H, m) |

TABLE 1-continued

Structure:
$R^1$, $R^2$ on quinone ring with Me group; side chain CH—(CH$_2$)$_n$—R$^5$ with R$^4$ substituent

| Compound No. | Prepared by the procedure by Example | R$^1$ | R$^2$ | R$^4$ | [Z—(CH$_2$)$_k$]$_m$R$^5$ | n | Molecular formula | Melting point (°C.) Physical properties | Nuclear magnetic resonance spectrum, δ value (ppm), TMS as internal standard |
|---|---|---|---|---|---|---|---|---|---|
| 37 | 6 | —CH=CH—CH=CH— | | phenyl | COOH | 2 | C$_{21}$H$_{18}$O$_4$ | 88–89 | 2.21(3H, s), 2.30–2.70(4H, m), 4.47(1H, t), 7.21(5H, m), 7.57(2H, m), 7.91(2H, m) |
| 38 | 6 | —CH=CH—CH=CH— | | phenyl | COOH | 3 | C$_{22}$H$_{20}$O$_4$ | 157–158 | 1.20–1.80(2H, m), 2.20(3H, s), 2.00–2.40(4H, m), 4.49(1H, t), 7.27(5H, m), 7.64(2H, m), 8.02(2H, m) |
| 39 | 7 | MeO | MeO | phenyl | COOH | 2 | C$_{19}$H$_{20}$O$_6$ | 127–128 | 2.04(3H, s), 2.10–2.80(4H, m), 4.06(6H, s), 4.33(1H, t), 7.25(5H, m) |
| 40 | 7 | MeO | MeO | phenyl | COOH | 3 | C$_{20}$H$_{22}$O$_6$ | 100–101 | 1.30–1.80(2H, m), 2.03(3H, s), 2.20–2.50(4H, m), 3.95(6H, s), 4.28(1H, t), 7.24(5H, m) |
| 41 | 8 | Me | Me | phenyl | COOEt | 2 | C$_{21}$H$_{24}$O$_4$ | 64–65 | 1.21(3H, t), 1.96(6H, s), 2.06(3H, s), 2.00–2.50(4H, m), 4.08(2H, q), 4.34(1H, t), 7.26(5H, m) |

TABLE 1-continued $$\underset{R^1 \phantom{xxx} R^2}{\overset{O \phantom{xxx} Me \phantom{xxx} CH-(CH_2)_n-R^5}{\underset{\underset{O}{\|}}{\bigodot}}}$$

| Compound No. | Prepared by the procedure by Example | R¹ | R² | R⁴ | R⁵ | n | Molecular formula | Melting point (°C.) Physical properties | Nuclear magnetic resonance spectrum, δ value (ppm), TMS as internal standard |
|---|---|---|---|---|---|---|---|---|---|
| 42 | 8 | —CH=CH—CH=CH— | | (phenyl) | COOEt | 2 | C₂₃H₂₂O₄ | 97-98 | 1.16(3H, t), 2.18(3H, s), 2.00–2.60(4H, m), 4.04(2H, q), 4.50(1H, t), 7.25(5H, m), 7.65(2H, m), 7.98(2H, m) |
| 43 | 9 | —CH=CH—CH=CH— | | (phenyl) | CH₂OAc | 4 | C₂₅H₂₆O₄ | oil | 1.10–1.80(6H, s), 2.00(3H, s), 2.20(3H, s), 4.01(2H, s), 4.49(1H, t), 7.28(5H, m), 7.66(2H, m), 8.03(2H, m) |
| 44 | 9 | —CH=CH—CH=CH— | | (4-methoxyphenyl, OMe) | CH₂OAc | 4 | C₂₆H₂₈O₅ | oil | 1.10–1.80(6H, s), 2.00(3H, s), 2.20(3H, s), 3.75(3H, s), 4.01(2H, m), 4.49(1H, t), 6.80(2H, d), 7.23(2H, d), 7.66(2H, m), 8.03(2H, m) |
| 45 | 10 | Me | Me | (phenyl) | CH₂OH | 5 | C₂₂H₂₈O₃ | oil | 1.10–1.70(8H, m), 1.9–2.4(3H), 1.97(6H), 2.05(3H), 3.66(2H), 4.29(1H), 7.24(5H) |
| 46 | 10 | Me | Me | (phenyl) | CH₂OH | 2 | C₁₉H₂₂O₃ | oil | 1.4–1.6(2H), 1.61(1H), 1.95(6H), 2.0–2.4(2H), 2.03(3H), 3.63(2H), 4.33(1H), 7.24(5H) |

TABLE 1-continued

![Structure: quinone with R¹, R² substituents and CH(R⁴)-(CH₂)ₙ-R⁵ and Me groups]

| Compound No. | Prepared by the procedure by Example | R¹ | R² | R⁴ | R⁵ | n | Molecular formula | Melting point (°C.) Physical properties | Nuclear magnetic resonance spectrum, δ value (ppm), TMS as internal standard |
|---|---|---|---|---|---|---|---|---|---|
| 47 | 10 | Me | Me | phenyl | CH₂OH | 4 | $C_{21}H_{26}O_3$ | oil | 1.1–1.7(6H), 1.54(1H), 1.97(6H), 2.0–2.4(2H), 2.04(3H), 3.58(2H), 4.30(1H), 7.23(5H) |
| 48 | 10 | Me | Me | phenyl | CH₂OH | 7 | $C_{24}H_{32}O_3$ | oil | 1.1–1.8(12H), 1.72(1H), 1.96(6H), 2.0–2.4(2H), 2.04(3H), 3.58(2H), 4.29(1H), 7.24(5H) |
| 49 | 10 | Me | Me | phenyl | CH₃ | 5 | $C_{22}H_{28}O_2$ | oil | 0.85(3H), 1.1–1.5(8H), 1.96(6H), 2.0–2.4(2H), 2.04(3H), 4.29(1H), 7.24(5H) |
| 50 | 2,10 | Me | Me | phenyl | COOH | 5 | $C_{22}H_{26}O_4$ | 128–129 | 1.1–1.8(6H), 1.97(6H), 2.0–2.4(2H), 2.04(3H), 2.32(2H), 4.29(1H), 7.24(5H), 8.50(1H) |
| 51 | 2,10 | Me | Me | phenyl | 2-COOH-phenoxy (OMe) | 2 | $C_{25}H_{24}O_5$ | 175–177 | 1.93(3H), 1.97(3H), 2.07(3H), 2.82(2H), 4.24(2H), 4.52(1H), 6.92(1H), 7.13(1H), 7.29(5H), 7.50(1H), 8.14(1H), 12.2(1H) |
| 52 | 10,15 | Me | Me | phenyl | —C≡C·COOH | 3 | $C_{22}H_{22}O_4$ | 134–136 | 1.4–1.8(2H), 1.97(6H), 2.0–2.4(2H), 2.05(3H), 2.38(2H), 4.31(1H), 5.70(1H), 7.24(5H) |

TABLE 1-continued

| Compound No. | Prepared by the procedure by Example | R¹ | R² | R⁴ | CH—(CH₂)ₙ—R⁵ R⁴ (n, R⁵) | n | Molecular formula | Melting point (°C.) Physical properties | Nuclear magnetic resonance spectrum, δ value (ppm), TMS as internal standard |
|---|---|---|---|---|---|---|---|---|---|
| 53 | 10 | Me | Me | phenyl | Me—C(Me)—COOH | 4 | $C_{24}H_{30}O_4$ | 112–113 | 1.1–1.6(6H), 1.17(6H), 1.97(6H), 2.0–2.4(2H), 2.04(3H), 4.27(1H), 7.23(5H), 11.0(1H) |
| 54 | 10 | Me | Me | phenyl | Me—C(Me)—COOH | 6 | $C_{30}H_{34}O_5$ | 75–76 | 1.1–1.7(6H), 1.75(2H), 1.95(6H), 2.0–2.4(2H), 2.04(3H), 3.84(3H), 3.94(2H), 4.30(2H), 6.84(2H), 7.23(5H), 7.94(2H) |
| 55 | 10 | Me | Me | phenyl | 4-(COOH)-C₆H₄-O— | 6 | $C_{29}H_{32}O_5$ | 126–127 | 1.1–1.7(6H), 1.77(2H), 1.96(6H), 2.0–2.4(2H), 2.04(3H), 3.99(2H), 4.30(1H), 6.89(2H), 7.24(5H), 8.03(2H), 11.8(1H) |
| 56 | 11 | MeO | MeO | phenyl | CH₂OH | 5 | $C_{22}H_{28}O_5$ | oil | 1.1–1.7(8H), 1.65(1H), 2.0–2.4(2H), 2.01(3H), 3.59(2H), 3.94(6H), 4.27(1H), 7.23(5H) |
| 57 | 11 | MeO | MeO | phenyl | Me—C(Me)—COOH | 4 | $C_{24}H_{30}O_6$ | 110–112 | 1.1–1.6(6H), 1.17(6H), 2.0–2.4(2H), 2.01(3H), 3.94(6H), 4.25(1H), 7.23(5H), 8.00(1H) |

TABLE 1-continued

Structure:
$$R^1, R^2 \text{ on quinone ring with Me, and } CH(R^4)-(CH_2)_n-R^5$$

| Compound No. | Prepared by the procedure by Example | $R^1$ | $R^2$ | $R^4$ | $R^5$ | n | Molecular formula | Melting point (°C.) Physical properties | Nuclear magnetic resonance spectrum, δ value (ppm), TMS as internal standard |
|---|---|---|---|---|---|---|---|---|---|
| 58 | 12 | Me | Me | phenyl | CH₂OCONH₂ | 4 | C₂₂H₂₇O₄ | 125-126 | 1.1-1.8(6H), 1.97(6H), 2.0-2.4(2H), 2.04(3H), 4.01(2H), 4.28(1H), 4.60(2H), 7.24(5H). |
| 59 | 12 | Me | Me | phenyl | CH₂OCONH₂ | 5 | C₂₃H₂₉NO₄ | 72-73 | 1.1-1.8(8H), 1.97(6H), 2.0-2.4(2H), 2.04(3H), 4.01(2H), 4.29(1H), 4.63(2H), 7.23(5H) |
| 60 | 13 | Me | Me | phenyl | CH₂OCONHMe | 4 | C₂₃H₂₉NO₄ | 135-136 | 1.1-1.8(6H), 1.97(6H), 2.0-2.4(2H), 2.04(3H), 2.76(3H), 4.02(2H), 4.29(1H), 4.56(1H), 7.24(5H) |
| 61 | 13 | Me | Me | phenyl | CH₂OCONHMe | 5 | C₂₄H₃₁NO₄ | 86-87 | 1.1-1.8(8H), 1.97(6H), 2.0-2.4(2H), 2.04(3H), 2.76(3H), 4.02(2H), 4.29(1H), 4.60(1H), 7.23(5H) |
| 62 | 14 | Me | Me | phenyl | —C≡C—CH₂OH | 3 | C₂₂H₂₆O₃ | oil | 1.2-1.8(3H), 1.9-2.4(4H), 1.97(6H), 2.03(3H), 4.16(2H), 4.30(1H), 5.53(2H), 7.23(5H) |
| 63 | 16 | Me | Me | phenyl | —O—C₆H₄—CONHCH | 6 | C₂₉H₃₃NO₅ | amorphous | 1.1-1.9(8H), 1.94(6H), 2.0-2.4(2H), 2.02(3H), 3.85(2H), 4.28(1H), 6.6-6.9(2H), 7.0-7.4(7H), 7.4-7.7(2H) |

TABLE 1-continued

| Compound No. | Prepared by the procedure by Example | R¹ | R² | R⁴ | R⁵ | n | Molecular formula | Melting point (°C.) Physical properties | Nuclear magnetic resonance spectrum, δ value (ppm), TMS as internal standard |
|---|---|---|---|---|---|---|---|---|---|
| 64 | 10 | Me | Me | phenyl | —C≡C(CH₂)₃C≡C—CH₂OH | 3 | C₂₇H₃₀O₃ | oil | 1.3–1.8(4H), 1.84(1H), 1.9–2.5(8H), 1.96(6H), 2.05(3H), 4.21(2H), 4.33(1H), 7.25(5H) |
| 65 | 10 | Me | Me | phenyl | —C≡C.CH₂OH | 3 | C₂₂H₂₄O₃ | 84–85 | 1.51(2H), 1.93(1H), 1.96(6H), 2.0–2.4(4H), 2.05(3H), 4.21(2H), 4.32(1H), 7.25(5H) |
| 66 | 10 | Me | Me | phenyl | —C≡C.CH₂CH₂OH | 4 | C₂₄H₂₈O₃ | oil | 1.2–1.7(4H), 1.9–2.4(5H), 1.96(6H), 2.04(3H), 2.36(2H), 3.61(2H), 4.31(1H), 7.23(5H) |
| 67 | 10 | Me | Me | phenyl | —C≡C.CH₂OH | 6 | C₂₅H₃₀O₃ | oil | 1.1–1.7(8H), 1.85(1H), 1.97(6H), 2.0–2.4(4H), 2.05(3H), 4.21(2H), 4.28(1H), 7.23(5H) |
| 68 | 4,17 | Me | Me | 2-methylthienyl | COOH | 4 | C₁₉H₂₂O₄S | 120–121 | 1.1–1.8(4H), 2.01(6H), 2.05(3H), 2.0–2.4(4H), 4.46(1H), 6.89(2H), 7.12(1H) |
| 69 | 19 | Me | Me | phenyl | CONHOH | 4 | C₂₁H₂₅NO₄ | 59–60 | 1.1–1.8(4H), 1.96(6H), 2.02(3H), 2.0–2.4(4H), 4.27(1H), 7.24(5H), 8.30(1H) |

TABLE 1-continued $$\text{R}^1, \text{R}^2, \text{Me}, \text{CH}-(\text{CH}_2)_n-\text{R}^5, \text{R}^4 \text{ on quinone}$$

| Compound No. | Prepared by the procedure by Example | R¹ | R² | R⁴ | R⁵ | n | Molecular formula | Melting point (°C.) Physical properties | Nuclear magnetic resonance spectrum, δ value (ppm), TMS as internal standard |
|---|---|---|---|---|---|---|---|---|---|
| 70 | 19 | Me | Me | phenyl | -CON(Me)OH | 4 | C₂₂H₂₇NO₄ | oil | 1.1–1.8(4H), 1.97(6H), 2.04(3H), 2.0–2.4(4H), 3.28(3H), 4.28(1H), 7.24(5H) |
| 71 | 19 | Me | Me | phenyl | -CON(Ph)OH | 4 | C₂₇H₂₉NO₄ | 96–97 | 1.1–1.8(4H), 1.96(3H), 1.98(3H), 2.03(3H), 2.00–2.40(4H), 4.24(1H), 7.23(5H), 7.38(5H) |
| 72 | 19 | Me | Me | phenyl | -CON(Ph)OH | 6 | C₂₉H₃₃NO₄ | oil | 1.1–1.8(8H), 1.94(6H), 2.03(3H), 2.0–2.4(4H), 4.24(1H), 7.21(5H), 7.37(5H) |
| 73 | 18 | Me | Me | phenyl | CH₂OH | 8 | C₂₅H₃₄O₃ | oil | 1.1–1.8(14H), 1.96(6H), 2.04(3H), 2.0–2.4(2H), 3.61(2H), 4.29(1H), 7.24(5H) |
| 74 | 18 | Me | Me | 4-MeO-phenyl | CH₂OH | 4 | C₂₂H₂₈O₃ | oil | 1.1–1.80(6H), 1.95(6H), 2.05(3H), 2.0–2.4(2H), 3.58(2H), 3.74(3H), 4.21(1H), 6.77(2H), 7.18(2H) |
| 75 | 18, 20 | Me | Me | 2-methylthienyl | CH₂OH | 4 | C₁₉H₂₂O₃S | oil | 1.1–1.8(6H), 1.98(6H), 2.04(3H), 2.0–2.4(2H), 3.60(2H), 4.48(1H), 6.88(2H), 7.12(1H) |

TABLE 1-continued

![Structure: 2,5-cyclohexadiene-1,4-dione with R1, R2, Me, and CH(R4)-(CH2)n-R5 substituents]

| Compound No. | Prepared by the procedure by Example | R¹ | R² | R⁴ | R⁵ | n | Molecular formula | Melting point (°C.) Physical properties | Nuclear magnetic resonance spectrum, δ value (ppm), TMS as internal standard |
|---|---|---|---|---|---|---|---|---|---|
| 76 | 18 | Me | Me | 5-methylindanyl | CH₂OH | 6 | C₂₆H₃₄O₃ | oil | 1.1–1.8(10H), 1.98(6H), 2.03(3H), 2.0–2.4(4H), 2.84(2H), 3.60(2H), 4.23(1H), 7.08(3H) |
| 77 | 18,20 | —CH=CH— | —CH=CH— | phenyl | CH₂OH | 4 | C₂₃H₂₄O₃ | 127–128 | 1.1–1.8(6H), 2.20(3H), 3.59(2H), 4.50(1H), 7.28(5H), 7.65(2H), 8.03(2H) |
| 78 | 18 | —CH=CH— | —CH=CH— | phenyl | CH₂OH | 6 | C₂₅H₂₈O₃ | oil | 1.1–1.8(10H), 2.21(3H), 2.0–2.4(2H), 3.59(2H), 4.49(1H), 7.25(5H), 7.67(2H), 8.05(2H) |
| 79 | 18,20 | —CH=CH— | —CH=CH— | 4-methoxyphenyl | CH₂OH | 4 | C₂₄H₂₆O₄ | oil | 1.1–1.8(6H), 2.21(3H), 2.0–2.2(2H), 3.58(2H), 3.76(3H), 4.45(1H), 6.78(2H), 7.24(2H), 7.63(2H), 8.01(2H) |
| 80 | 18 | MeO | MeO | 2-methylthienyl | CH₂OH | 4 | C₁₉H₂₄O₅S | oil | 1.1–1.75(6H), 2.03(3H), 2.0–2.3(2H), 3.59(2H), 3.97(6H), 4.46(1H), 6.85(2H), 7.13(1H) |
| 81 | 18,20 | MeO | MeO | phenyl | CH₂OH | 4 | C₂₁H₂₆O₅ | 30–31 | 1.1–1.8(6H), 2.02(3H), 2.0–2.3(2H), 3.60(2H), 3.95(6H), 4.29(1H), 7.24(5H) |

TABLE 1-continued
| Compound No. | Prepared by the procedure by Example | R¹ | R² | R⁴ | n | R⁵ | Molecular formula | Melting point (°C.) Physical properties | Nuclear magnetic resonance spectrum, δ value (ppm), TMS as internal standard |
|---|---|---|---|---|---|---|---|---|---|
| 82 | 18 | MeO | MeO | 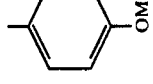 | 4 | CH₂OH | C₂₂H₂₈O₆ | oil | 1.1–1.8(6H), 2.02(3H), 2.0–2.4(2H), 3.59(2H), 3.75(3H), 3.94(6H), 4.21(1H), 6.78(2H), 7.18(2H) |
| 83 | 18 | MeO | MeO | 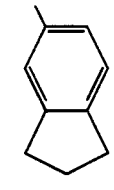 | 6 | CH₂OH | C₂₆H₃₄O₅ | oil | 1.1–1.8(10H), 2.03(3H), 2.00–2.3(4H), 2.85(4H), 3.60(2H), 3.95(6H), 4.23(1H), 7.10(3H) |
| 84 | 18 | MeO | MeO |  | 8 | CH₂OH | C₂₅H₃₄O₅ | 42–43 | 1.1–1.8(14H), 2.02(3H), 2.0–2.3(2H), 3.60(2H), 3.95(6H), 4.27(1H), 7.23(5H) |

EXAMPLE 21

(Compound No. 90)

Toluene (15 ml) was added to 0.76 g (5.0 mmole) of 2,5,6-trimethylhydroquinone and 1.28 g (5.0 mmole) of 7-(4-chlorophenyl)-7-hydroxyheptanoic acid, and the mixture was warmed at 60° C. and stirred. 0.19 ml (5.0×0.3 mmole) of boron trifluoride ethyl etherate was added to the mixture, followed by stirring at 60° C. for 15 hours. After the conclusion of the reaction, a large amount of the toluene was distilled off, and the residue was dissolved in tetrahydrofuran (20 ml). An aqueous solution (10 ml) of ferric chloride (2.7 g, 10.0 mmole was added to the solution, followed by stirring at room temperature for 20 minutes. The tetrahydrofuran was distilled off, and ethyl acetate was added to the residue to extract the reaction product. The organic layer was separated out, washed with aqueous sodium chloride solution and dried (magnesium sulfate). The ethyl acetate solution was chromatographed on a short silica gel (10 g) column, and elution was performed with ethyl acetate. The fractions containing the object compound were collected and concentrated under reduced pressure, and the residue was recrystallized from ethyl acetate/isopropyl ether to give 1.52 g (78%) of 7-(4-chlorophenyl)-7-(3,5,6-trimethyl-1,4-benzoquinon -2-yl)heptanoic acid.

TABLE 1
(continued)

| Compound No. | Prepared by the procedure by Example | $R^1$ | $R^2$ | $R^4$ | $R^5$ | n | Molecular formula | Melting point (°C.) Physical properties | Nuclear magnetic resonance spectrum, δ value (ppm), TMS as internal standard |
|---|---|---|---|---|---|---|---|---|---|
| 85 | 21 | —CH=CH—CH=CH— | | phenyl | $CO_2Et$ | 5 | $C_{26}H_{28}O_4$ | oil | 1.1–1.8(6H), 1.21(3H), 2.0–2.4(4H), 2.20(3H), 4.08(2H), 4.49(1H), 7.0–7.4(5H), 7.5–7.8(2H), 7.9–8.2(2H) |
| 86 | 17, 21 | —CH=CH—CH=CH— | | phenyl | $CO_2H$ | 5 | $C_{24}H_{24}O_4$ | 137–138 | 1.1–1.8(6H), 2.0–2.3(2H), 2.19(3H), 2.30(2H), 4.47(1H), 5.50(1H), 7.0–7.4(5H), 7.5–7.8(2H), 7.9–8.2(2H) |
| 87 | 21 | Me | Me | 4-F-phenyl | $CO_2H$ | 5 | $C_{22}H_{25}FO_4$ | 141–142 | 1.1–1.8(6H), 1.9–2.3(2H), 1.95(3H), 1.97(3H), 2.04(3H), 2.31(2H), 4.21(1H), 6.9–7.3(1H), 6.91(2H), 7.22(2H) |
| 88 | 21 | MeO | MeO | 4-F-phenyl | $CO_2H$ | 5 | $C_{22}H_{25}FO_6$ | 121–122 | 1.1–1.8(6H), 1.9–2.3(2H), 2.03(3H), 2.31(2H), 3.93(3H), 3.94(3H), 4.20(1H), 6.9–7.3(1H), 6.92(2H), 7.22(2H) |
| 89 | 21 | —CH=CH—CH=CH— | | 4-F-phenyl | $CO_2H$ | 5 | $C_{24}H_{23}FO_4$ | 132–133 | 1.1–1.8(6H), 2.0–2.3(2H), 2.21(3H), 2.30(2H), 4.21(1H), 6.9–7.4(1H), 6.94(2H), 7.28(2H), 7.5–7.8(2H), 7.9–8.2(2H) |
| 90 | 21 | Me | Me | 4-Cl-phenyl | $CO_2H$ | 5 | $C_{22}H_{25}ClO_4$ | 142–143 | 1.1–1.8(6H), 1.9–2.3(2H), 1.95(3H), 1.97(3H), 2.04(3H), 2.31(2H), 4.21(1H), 7.0–7.3(1H), 7.20(4H) |
| 91 | 21 | MeO | MeO | 4-Cl-phenyl | $CO_2H$ | 5 | $C_{22}H_{25}ClO_6$ | 141–142 | 1.1–1.8(6H), 1.9–2.3(2H), 2.02(3H), 2.31(2H), 3.93(3H), 3.94(3H), 4.19(1H), 6.9–7.2(1H), 7.20(4H) |
| 92 | 21 | —CH=CH—CH=CH— | | 4-Cl-phenyl | $CO_2H$ | 5 | $C_{24}H_{23}ClO_4$ | 147–149 | 1.1–1.8(6H), 2.0–2.3(2H), 2.20(3H), 2.30(2H), 4.39(1H), 7.0–7.3(1H), 7.24(4H), 7.5–7.8(2H), 7.9–8.2(2H) |

TABLE 1-continued

| Compound No. | Prepared by the procedure by Example | $R^1$ | $R^2$ | $R^4$ | $R^5$ | n | Molecular formula | Melting point (°C.) Physical properties | Nuclear magnetic resonance spectrum. δ value (ppm). TMS as internal standard |
|---|---|---|---|---|---|---|---|---|---|
| 93 | 21 | Me | Me | 4-Me-C6H4 | $CO_2H$ | 5 | $C_{23}H_{28}O_4$ | 138-139 | 1.1-1.8(6H), 1.9-2.3(2H), 1.96(6H), 2.04(3H), 2.27(3H), 2.30(2H), 4.22(1H), 6.9-7.2(1H), 7.02(2H), 7.15(2H) |
| 94 | 21 | MeO | MeO | 4-Me-C6H4 | $CO_2H$ | 5 | $C_{23}H_{28}O_6$ | 134-135 | 1.1-1.8(6H), 1.9-2.3(2H), 2.01(3H), 2.27(3H), 2.31(2H), 3.94(6H), 4.21(1H), 6.9-7.2(1H), 7.02(2H), 7.15(2H) |
| 95 | 21 | Me | Me | 4-i-Pr-C6H4 | $CO_2H$ | 5 | $C_{25}H_{32}O_4$ | 135-137 | 1.1-1.8(6H), 1.20(6H), 1.9-2.3(2H), 1.96(6H), 2.04(3H), 2.30(2H), 2.84(1H), 4.23(1H), 7.0-7.2(1H), 7.12(4H) |
| 96 | 21 | MeO | MeO | 4-i-Pr-C6H4 | $CO_2H$ | 5 | $C_{25}H_{32}O_6$ | 85-87 | 1.1-1.8(6H), 1.20(6H), 1.9-2.3(2H), 2.02(3H), 2.31(2H), 2.84(1H), 3.93(6H), 4.22(1H), 7.0-7.3(1H), 7.12(4H) |
| 97 | 21 | Me | Me | 3,4-(MeO)2-C6H3 | $CO_2H$ | 5 | $C_{24}H_{30}O_6$ | 123-124 | 1.1-1.8(6H), 1.96(6H), 2.05(3H), 2.00-2.45(4H), 3.88(6H, s) 4.18(1H), 6.77(3H) |

EXAMPLE 22

(Compound No. 98)

Trimethylhydroquinone (1.5 g, 10 mmole) and 5-(1-hydroxyethyl)-2-thienylacetic acid (2.5 g, 8.5 mmole) were added to 50 ml of toluene, and D-camphorsulfonic acid (0.2 g) was added to the mixture, followed by heating at 50° C. for 6 hours with stirring. After cooling, the reaction solution was concentrated under reduced pressure, and the residue was dissolved in THF. An aqueous solution of ferric chloride was added to the solution, followed by stirring at room temperature for 10 minutes. The reaction solution was extracted with isopropyl ether, and the organic layer was washed with water, dried and evaporated under reduced pressure. The crude product was purified by silica gel column chromatography using IPE:hexane(1:1) to give ethyl-5-[1-(3,5,6-trimethyl-1, 4-benzoquinon -2-yl)ethyl]-2-thienylacetate (2.4 g, 72%). Hydrolysis of this compound with 6N hydrochloric acid in THF yielded 5-[1-(3,5,6-trimethyl-1,4-benzoquinon-2-yl)ethyl]-2-thienylacetic acid (2.1 g, 90%). δ6.69(2H,m), 4.61(1H,m), 3.73(2H,s), 1.98(9H,s), 1.61(3H,d, 7Hz).

EXAMPLE 23

(Compound No. 99)

To 100 ml of toluene were added 2.2 g (2 mmole) of trimethylhydroquinone and 3 g (1.5 mmole) of ethyl 4-(1-hydroxyethyl)phenylacetate, and after 0.2 g of D-camphorsulfonic acid was added, the reaction solution was stirred for 18 hours with heating at 60° C., cooled and evaporated under reduced pressure. The residue was dissolved in THF, and an aqueous solution of ferric chloride was added to the solution to carry out oxidation. Isopropyl ether (IPE) was added to the reaction solution, and the mixed solution was washed with water, dried and then evaporated under reduced pressure. The crude product was purified by silica gel column chromatography using solution: IPE to give ethyl 4-[1-(3,5,6-trimethyl-1,4-benzoquinon -2-yl)ethyl]phenylacetate. Hydrolysis of this compound with 6N hydrochloric acid in THF yielded 4-[1-(3,5,6-trimethyl-1,4-benzoquinon-2-yl)ethyl]phenylacetic acid (1 g, uield of 31%). This compound was recrystallized from IPE, m.p. 142°-143° C. δ8.70(1H,COOH), 7.19(4H,s), 4.52(1H,m), 3.58(2H,s), 1.98 (9H,s), 1.57(2H,d,7Hz).

EXAMPLE 24

(Compound No. 100)

To 80 ml of toluene were added trimethylhydroquinone (1.5 g, 10 mmole) and 4,4-dimethoxybenzohydrol (2.4 g, 10 mmole), and D-camphor-sulfonic acid (0.1 g) was added to the mixture, followed by heating at 60° C. for 6 hours with stirring. After cooling, the reaction solution was concentrated under reduced pressure. The residue was dissolved in THF, and an aqueous solution of ferric chloride was added to the solution, followed by stirring at room temperature for 10 minutes. The reaction solution was extracted with isopropyl ether, and the organic layer was washed with water, dried and then evaporated under reduced pressure. The crude product was purified by silica gel column chromatography using IPE: hexane (1:2) to give bis(4-methoxyphenyl)-3,5,6-trimethyl-1,4-benzoquinonylmethane (2.9 g, 81%). δ7.04(4H,d,8Hz), 6.77(4H,d,8Hz), 5.83(1H,s), 3.76(6H,s), 1.98(6H,s), 1.82(3H,s).

EXAMPLE 25

(Compound NO. 101)

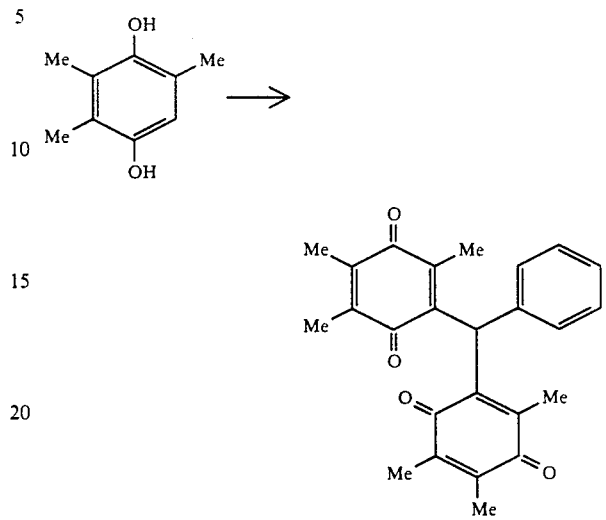

To 100 ml of toluene were added trimethylhydroquinone (4.4 g, 4 mmole) and benzal chloride (2.3 g, 1.4 mmole), and after the addition of boron trifluoride diethyl etherate (0.5 ml), the reaction solution was heated at 50° C. for 18 hours under stirring, cooled and evaporated under reduced pressure. The residue was dissolved in THF, and an aqueous solution of ferric chloride was added to the solution, followed by stirring at room temperature for 10 minutes. Isopropyl ether (IPE) was added to the reaction solution, and the organic layer was washed with water, dried and evaporated under reduced pressure. The crude product was purified by silica gel column chromatography using IPE to give phenyl-bis-3,5,6-trimethyl-1,4-benzoquinonylmethane (4 g, yield of 74%). δ7.17(5H,m), 3.71(1H,s), 2.00(12H,s), 1.78(6H,s).

EXAMPLE 26

(Compound No. 102)

A cooled solution of ceric ammonium nitrate (1.37 g, 25 mmole) in 50% aqueous acetonitrile (20 ml) was added dropwise to a solution of 7-(1,4-dimethoxy-3,5,6-trimethyl phenyl)octanoic acid (2 g, 6.2 mmole) in 30% aqueous acetonitrile (20 ml) under ice-cooling. The reaction solution was stirred as such for 20 minutes, and extracted with IPE. The organic layer was washed with water, dried and concentrated under reduced pressure, and the resulting crude product was purified by silica gel column chromatography using IPE to give 7-(3,5,6-trimethyl-1,4-benzoquinon-2-yl)octanoic acid (1.6 g, 72%). 2.92(1H,m), 2.30(3H,t,6Hz), 2.02(3H,s), 1.99(6H,s), 1.59 (6H,m), 1.21(3H,d,7Hz).

EXAMPLE 27

(Compound No. 119)

1,2-Dichloroethane (15 ml) was added to 0.76 g (5.0 mmole) of trimethylhydroquinone and 1.45 g (5.0 mmole) of 7-(3-trifluoromethylphenyl)-7-hydroxyheptanoic acid, and the mixture was warmed to 80° C. under stirring and admixed with 0.19 ml (5.0×0.3 mmole) of boron trifluoride ethyl etherate, followed by stirring at 80° C. for 2 hours. After the reaction solution was cooled by standing at room temperature, the solvent was distilled off, and the residue was dissolved in tetrahydrofuran (15 ml). A solution of 2.7 g (10.0 mmole) of ferric chloride in water (10 ml) was added to the solution, followed by stirring at room temperature for 20 minutes. The tetrahydrofuran was distilled off, and ethyl acetate was added to the residue to carry out extraction. The organic layer was separated out, washed with aqueous sodium chloride solution, dried (magnesium sulfate) and evaporated, and the residue was chromatographed on a silica gel column chromatography, followed by elution with isopropyl ether. The fractions containing the object compound were collected and concentrated under reduced pressure, and the residue was recrystallized from isopropyl ether-hexane to give 0.50 g (24%) of 7-(3-trifluoromethylphenyl)-7-(3,5,6-trimethyl-1,4-benzoquinon -2-yl)heptanoic acid.

EXAMPLE 28

(Compound No. 126)

1,2-Dichloroethane (15 ml) was added to 0.76 g (5.0 mmole) of trimethylhydroquinone and 1.51 g (5.0 mmole) of methyl 7-hydroxy-7-[4-(1-imidazolyl)phenyl]heptanoate, followed by warming at 80° C. and stirring. 1.42 ml (5.0×2.3 mmole) of boron trifluoride ethyl etherate was added dropwise to the mixture, followed by stirring at 80° C. for 2 hours. Then, methanol (15 ml) was added to the reaction solution, followed by further stirring at 80° C. for 2 hours. After cooling by standing at room temperature, the solvent was distilled off, and the residue was dissolved in tetrahydrofuran (20 ml). A solution of 2.7 g (10.0 mmole) of ferric chloride in water (10 ml) was added to the solution, followed by stirring at room temperature for 20 minutes. The tetrahydrofuran was distilled off, and chloroform was added to the residue to conduct extraction. The organic layer was separated out, washed with aqueous sodium hydrogencarbonate solution added, then washed with aqueous sodium chloride solution, dried (magnesium sulfate) and evaporated. The residue was chromatographed on a silica gel column, and elution was effected with ethyl acetate. The fractions containing the object compound were collected, and the solvent was distilled off under reduced pressure to give 1.70 g (78%) of methyl 7-[4-(1-imidazolyl)phenyl]-7-(3,5,6-trimethyl-1,4-benzoquinon -2-yl)heptanoate.

EXAMPLE 29

(Compound No. 127)

In acetic acid (17 ml) was dissolved 1.70 g (3.92 mmole) of methyl 7-[4-(1-imidazolyl)phenyl]-7-(3,5,6-trimethyl-1,4-benzoquinon -2-yl)heptanoate, and concentrated hydrochloric acid (7.8 ml) was added to the solution, followed by stirring at 100° C. for 1 hour. The solvent was distilled off, and acetone was added to the residue, followed by concentration under reduced pressure. The crystals, which separated out, were collected by filtration and recrystallized from ethanol/ethyl ether to give 1.30 g (73%) of 7-[4-(1-imidazolyl)phenyl]-7-(3,5,6-trimethyl-1,4-benzoquinon -2-yl)heptanoic acid.-hydrochloride.

EXAMPLE 30

(Compound No. 133)

In acetic acid (35 ml) was dissolved 3.50 g (8.06 mmole) of methyl 6-[4-(1-imidazolyl)benzyl]-6-(3,5,6-trimethyl-1,4-benzoquinon -2-yl)hexanoate, and concentrated hydrochloric acid (16.1 ml) was added to the solution, followed by stirring at 100° C. for 1 hour. The solvent was distilled off, and acetone was added to the residue, followed by concentration under reduced pressure. The residue was chromatographed on a silica gel column, and elution was performed with chloroform/methanol (6:1). The fractions containing the object compound were collected nd concentrated under reduced pressure, and the residue was crystallized to give 2.94 g (87%) of 6-[4-(1-imidazolyl)benzyl]-6-(3,5,6-trimethyl-1,4-benzoquinon -2-yl)hexanoic acid.

TABLE 1

| Compound No. | Prepared by the procedure by Example | $R^1$ | $R^2$ | $R^4$ | $R^5$ | n | Molecular formula | Melting point (°C) Physical properties | Nuclear Magnetic resonance spectrum, δ value (ppm). TMS as internal standard |
|---|---|---|---|---|---|---|---|---|---|
| 103 | 2 | Me | Me | phenyl | $CO_2H$ | 7 | $C_{24}H_{30}O_4$ (382.50) C, 75.36; H, 7.91 | m.p 125~127° C. | 1.1–1.8(10H), 1.9–2.3(2H), 1.97(6H), 2.04(3H), 2.32(2H), 4.29(1H), 7.0–7.4(1H), 7.23(5H) |
| 104 | 2 | MeO | MeO | phenyl | $CO_2H$ | 7 | $C_{24}H_{30}O_6$ (414.50) C, 69.54; H, 7.30 | m.p 73~75° C. | 1.1–1.8(10H), 1.9–2.3(2H), 2.01(3H), 2.32(2H), 3.94(6H), 4.27(1H), 7.0–7.4(1H), 7.23(5H) |
| 105 | 2 | Me | Me | 2-OMe-phenyl | $CO_2H$ | 5 | $C_{23}H_{28}O_5$ (384.47) C, 71.85; H, 7.34 | m.p 152~153° C. | 1.1–1.8(6H), 1.9–2.3(2H), 1.94(6H), 2.03(3H), 2.31(2H), 3.68(3H), 4.43(1H), 6.7–7.6(5H) |
| 106 | 2 | MeO | MeO | 2-OMe-phenyl | $CO_2H$ | 5 | $C_{23}H_{28}O_7$ (416.47) C, 66.33; H, 6.78 | m.p 93-94° C. | 1.1–1.8(6H), 1.9–2.3(2H), 1.97(3H), 2.31(2H), 3.69(3H), 3.93(6H), 4.45(1H), 6.7–7.6(5H) |
| 107 | 2 | Me | Me | 3-F-phenyl | $CO_2H$ | 5 | $C_{22}H_{25}FO_4$ (372.44) C, 70.95; H, 6.77 | m.p 113~114° C. | 1.1–1.8(6H), 1.9–2.3(2H), 1.96(3H), 1.97(3H), 2.04(3H), 2.31(2H), 4.26(1H), 6.7–7.4(5H) |
| 108 | 2 | MeO | MeO | 3-F-phenyl | $CO_2H$ | 5 | $C_{22}H_{25}FO_6$ (404.43) C, 65.34; H, 6.23 | m.p 72~73° C. | 1.1–1.8(6H), 1.9–2.3(2H), 2.01(3H), 2.31(2H), 3.95(6H), 4.24(1H), 6.7–7.4(5H) |
| 109 | 2 | Me | Me | 2-Me-phenyl | $CO_2H$ | 5 | $C_{23}H_{28}O_4$ (368.47) C, 74.97; H, 7.66 | m.p 156~158° C. | 1.1–1.8(6H), 1.9–2.3(2H), 1.88(3H), 1.98(6H), 2.10(3H), 2.31(2H), 4.37(1H), 7.0–7.6(4H), 7.86(1H) |

TABLE 1-continued

| Compound No. | Prepared by the procedure by Example | R¹ | R² | R⁴ | R⁵ | n | Molecular formula | Melting point (°C.) Physical properties | Nuclear Magnetic resonance spectrum, δ value (ppm). TMS as internal standard |
|---|---|---|---|---|---|---|---|---|---|
| 110 | 2 | MeO | MeO | (2-Me-phenyl) | CO₂H | 5 | C₂₃H₂₈O₆ (400.47) C, 68.98; H, 7.05 | m.p. 100~102° C. | 1.1–1.8(6H), 1.84(3H), 1.9–2.3(2H), 2.10(3H), 2.32(2H), 3.96(6H), 4.39(1H), 7.0–7.6(4H), 8.67(1H) |
| 111 | 2 | Me | Me | (3-MeO-phenyl) | CO₂H | 5 | C₂₃H₂₈O₅ (384.47) C, 71.85; H, 7.34 | m.p. 102~104° C. | 1.1–1.8(6H), 1.9–2.3(2H), 1.97(6H), 2.03(3H), 2.31(2H), 3.76(3H), 4.26(1H), 6.6–7.3(5H) |
| 112 | 2 | Me | Me | (3-Cl-phenyl) | CO₂H | 5 | C₂₂H₂₅ClO₄ (388.89) C, 67.95; H, 6.48 | m.p. 108~110° C. | 1.1–1.8(6H), 1.9–2.3(2H), 1.96(3H), 1.97(3H), 2.04(3H), 2.31(2H), 4.23(1H), 6.00(1H), 7.1–7.3(4H) |
| 113 | 2 | MeO | MeO | (3-Cl-phenyl) | CO₂H | 5 | C₂₂H₂₅ClO₅ (420.89) C, 62.78; H, 5.99 | m.p. 84~86° C. | 1.1–1.8(6H), 1.9–2.3(2H), 2.0(3H), 2.31(2H), 3.96(6H), 4.21(1H), 6.57(1H), 7.1–7.3(4H) |
| 114 | 2 | Me | Me | (4-F-phenyl) | CO₂H | 4 | C₂₁H₂₃FO₄ (358.41) C, 70.37; H, 6.47 | m.p. 88~89° C. | 1.1–1.8(4H), 1.9–2.3(2H), 1.95(3H), 1.96(3H), 2.04(3H), 2.32(2H), 4.21(1H), 4.0–4.7(1H), 6.91(2H), 7.22(2H) |
| 115 | 2 | Me | Me | (4-Cl-phenyl) | CO₂H | 4 | C₂₁H₂₃ClO₄ (374.86) C, 67.29; H, 6.18 | m.p. 93~95° C. | 1.1–1.8(4H), 1.9–2.3(2H), 1.95(3H), 1.96(3H), 2.04(3H), 2.32(2H), 4.21(1H), 4.0–4.7(1H), 7.20(4H) |
| 116 | 2 | Me | Me | (4-Me-phenyl) | CO₂H | 4 | C₂₂H₂₆O₄ (354.45) C, 74.55; H, 7.39 | m.p. 109~110° C. | 1.1–1.8(4H), 1.9–2.3(2H), 1.96(6H), 2.04(3H), 2.27(3H), 2.32(2H), 4.23(1H), 7.0–7.3(1H), 7.04(2H), 7.15(2H) |

TABLE 1-continued

| Compound No. | Prepared by the procedure by Example | $R^1$ | $R^2$ | $R^4$ | $R^5$ | n | Molecular formula | Melting point (°C.) Physical properties | Nuclear Magnetic resonance spectrum, δ value (ppm). TMS as internal standard |
|---|---|---|---|---|---|---|---|---|---|
| 117 | 2 | —CH=CH—CH=CH— | | 4-Me-phenyl | $CO_2H$ | 5 | $C_{25}H_{26}O_4$ (390.48) C, 76.90; H, 6.70 | m.p. 135~137° C. | 1.1-1.8(6H), 2.0-2.3(2H), 2.20(3H), 2.27(3H), 2.30(2H), 4.42(1H), 7.0-7.3(1H), 7.05(2H), 7.21(2H), 7.5-7.8(2H), 7.9-8.2(2H) |
| 118 | 2 | Me | Me | 4-Br-phenyl | $CO_2H$ | 5 | $C_{22}H_{25}BrO_4$ (433.35) C, 60.98; H, 5.82 | m.p. 148~150° C. | 1.1-1.8(6H), 1.9-2.3(2H), 1.95(3H), 1.97(3H), 2.04(3H), 2.31(2H), 4.18(1H), 7.0-7.5(1H), 7.12(2H), 7.37(2H) |
| 119 | 27 | Me | Me | 3-$CF_3$-phenyl | $CO_2H$ | 5 | $C_{23}H_{25}F_3O_4$ (422.44) C, 65.39; H, 5.97 | m.p. 104~105° C. | 1.1-1.8(6H), 1.9-2.3(2H), 1.95(3H), 1.95(3H), 1.99(3H), 2.05(3H), 2.32(2H), 4.30(1H), 7.3-7.6(5H) |
| 120 | 28 | Me | Me | 4-Me-phenyl-pyrrolyl | $CO_2Me$ | 2 | $C_{24}H_{26}N_2O_4$ (392.46) C, 70.39; H, 6.16; N, 7.14 | oil | 1.96(3H), 1.99(3H), 2.12(3H), 2.1-2.8(4H), 3.64(3H), 4.35(1H), 7.16(1H), 7.23(1H), 7.27(2H), 7.42(2H), 7.80(1H) |
| 121* | 29 | Me | Me | 4-Me-phenyl-pyrrolyl | $CO_2H$ | 2 | $C_{22}H_{22}N_2O_4$ (414.89) C, 63.69; H, 5.59; N, 6.75 | m.p. 185~187° C. | 1.87(3H), 1.94(3H), 2.08(3H), 2.1-2.5(4H), 4.33(1H), 5.0-7.8(2H), 7.48(2H), 7.72(2H), 7.85(1H), 8.22(1H), 9.70(1H) |
| 122 | 28 | Me | Me | 4-Me-phenyl-pyrrolyl | $CO_2Me$ | 3 | $C_{24}H_{26}N_2O_4$ (406.48) C, 70.92; H, 6.45; N, 6.89 | oil | 1.5-1.8(2H), 1.96(3H), 1.99(3H), 2.12(3H), 2.1-2.4(2H), 2.37(2H), 3.66(3H), 4.31(1H), 7.16(1H), 7.23(1H), 7.28(2H), 7.42(2H), 7.81(1H) |
| 123* | 29 | Me | Me | 4-Me-phenyl-pyrrolyl | $CO_2H$ | 3 | $C_{23}H_{24}N_2O_4\cdot HCl$ (428.92) C, 64.41; H, 5.64; N, 6.53 | m.p. 117~119° C. | 1.3-1.7(2H), 1.89(3H), 1.93(3H), 2.0-2.3(2H), 2.06(3H), 2.25(2H), 3.3-5.6(2H), 4.32(2H), 7.50(2H), 7.73(2H), 7.84(1H), 8.22(1H), 9.73(1H) |
| 124 | 28 | Me | Me | 4-Me-phenyl-pyrrolyl | $CO_2Me$ | 4 | $C_{25}H_{28}N_2O_4$ (420.51) C, 71.41; H, 6.71; N, 6.66 | oil | 1.2-1.9(4H), 1.96(3H), 2.00(3H), 2.0-2.3(2H), 2.11(3H), 2.31(2H), 3.63(3H), 4.28(1H), 7.17(1H), 7.23(1H), 7.28(2H), 7.41(2H), 7.81(1H) |

TABLE 1-continued

| Compound No. | Prepared by the procedure by Example | $R^1$ | $R^2$ | $R^4$ | $R^5$ | n | Molecular formula | Melting point (°C.) Physical properties | Nuclear Magnetic resonance spectrum, δ value (ppm). TMS as internal standard |
|---|---|---|---|---|---|---|---|---|---|
| 125* | 30 | Me | Me | pyrrole-N-phenyl | $CO_2H$ | 4 | $C_{24}H_{26}N_2O_4$ (406.48) C, 70.92; H, 6.45; N, 6.89 | m.p. 163~165° C. | 1.0–1.7(4H), 1.92(6H), 2.03(3H), 1.9–2.3(4H), 2.7–3.8(4H), 4.27(1H), 7.06(1H), 7.37(2H), 7.51(2H), 7.62(1H), 8.14(1H) |
| 126 | 28 | Me | Me | pyrrole-N-phenyl | $CO_2Me$ | 5 | $C_{26}H_{30}N_2O_4$ (434.54) C, 71.87; H, 6.96; N, 6.45 | oil | 1.2–1.9(6H), 1.96(3H), 2.00(3H), 2.0–2.3(2H), 2.10(3H), 2.25(2H), 3.64(3H), 4.28(1H), 7.17(1H), 7.23(1H), 7.28(2H), 7.41(2H), 7.81(1H) |
| 127* | 29 | Me | Me | pyrrole-N-phenyl | $CO_2H$ | 5 | $C_{25}H_{28}N_2O_4$·HCl (456.97) C, 65.71; H, 6.40; N, 6.13 | m.p. 114~116° C. | 1.0–1.7(6H), 1.88(3H), 1.93(3H), 1.9–2.3(4H), 2.05(3H), 4.30(1H), 6.0–7.8(2H), 7.49(2H), 7.72(2H), 7.87(1H), 8.23(1H), 9.70(1H) |
| 128 | 28 | Me | Me | pyrrole-N-CH2-phenyl | $CO_2Me$ | 2 | $C_{24}H_{26}N_2O_4$ (406.48) C, 70.92; H, 6.45; N, 6.89 | oil | 1.94(3H), 1.96(3H), 2.07(3H), 2.0–2.74(4H), 3.62(3H), 4.31(1H), 5.06(2H), 6.87(1H), 7.02(1H), 7.06(2H), 7.29(2H), 7.50(1H) |
| 129* | 30 | Me | Me | pyrrole-N-CH2-phenyl | $CO_2H$ | 2 | $C_{23}H_{24}N_2O_4$ (392.46) C, 70.39; H, 6.16; N, 7.14 | m.p. 190° C. (dec.) | 1.88(3H), 1.92(3H), 2.02(3H), 2.0–2.5(4H), 3.0–4.1(1H), 4.24(1H), 5.13(2H), 6.86(1H), 7.08(1H), 7.13(2H), 7.25(2H), 7.67(1H) |
| 130 | 28 | Me | Me | pyrrole-N-CH2-phenyl | $CO_2Me$ | 3 | $C_{25}H_{28}N_2O_4$ (420.51) C, 71.41; H, 6.71; N, 6.66 | oil | 1.4–1.8(2H), 1.95(3H), 1.97(3H), 2.0–2.3(2H), 2.06(3H), 2.34(2H), 3.63(3H), 4.26(1H), 5.06(2H), 6.88(1H), 7.05(2H), 7.06(1H), 7.28(2H), 7.50(1H) |
| 131* | 30 | Me | Me | pyrrole-N-CH2-phenyl | $CO_2H$ | 3 | $C_{24}H_{26}N_2O_4$ (406.48) C, 70.92; H, 6.45; N, 6.89 | m.p. 128~132° C. | 1.2–1.6(2H), 1.89(6H), 1.98(3H), 1.9–2.2(2H), 2.21(2H), 4.23(1H), 5.13(2H), 6.7–7.4(1H), 6.91(1H), 7.13(2H), 7.16(1H), 7.25(2H), 7.77(1H) |
| 132 | 28 | Me | Me | pyrrole-N-CH2-phenyl | $CO_2Me$ | 4 | $C_{26}H_{30}N_2O_4$ (434.54) C, 71.87; H, 6.96; N, 6.45 | oil | 1.2–1.9(4H), 1.94(3H), 1.96(3H), 2.05(3H), 2.0–2.3(2H), 2.28(2H), 3.62(3H), 4.24(1H), 5.05(2H), 6.88(1H), 7.04(2H), 7.05(1H), 7.27(2H), 7.50(1H) |

TABLE 1-continued

| Compound No. | Prepared by the procedure by Example | $R^1$ | $R^2$ | $R^4$ | $R^5$ | n | Molecular formula | Melting point (°C.) Physical properties | Nuclear Magnetic resonance spectrum, δ value (ppm). TMS as internal standard |
|---|---|---|---|---|---|---|---|---|---|
| 133* | 30 | Me | Me |  | $CO_2H$ | 4 | $C_{25}H_{28}N_2O_4$ (420.51) C, 71.41; H, 6.71; N, 6.66 | 98–102° C. | 1.0–1.7(4H), 1.87(3H), 1.89(3H), 1.98(3H), 1.9–2.2(2H), 2.16(2H), 4.23(1H), 5.23(2H), 7.19(1H), 7.25(4H), 7.39(1H), 8.38(1H), 9.20(1H) |
| 134 | 28 | Me | Me |  | $CO_2Me$ | 5 | $C_{27}H_{32}N_2O_4$ (448.56) C, 72.30; H, 7.19; N, 6.25 | oil | 1.1–1.8(6H), 1.95(3H), 1.97(3H), 2.04(3H), 2.0–2.3(2H), 2.26(2H), 3.63(3H), 4.23(1H), 5.05(2H), 6.87(1H), 7.04(2H), 7.05(1H), 7.26(2H), 7.50(1H) |
| 135* | 30 | Me | Me |  | $CO_2H$ | 5 | $C_{26}H_{30}N_2O_4$ (434.54) C, 71.87; H, 6.96; N, 6.45 | 118–123 | 1.0–1.7(6H), 1.88(3H), 1.90(3H), 1.99(3H), 1.9–2.2(2H), 2.14(2H), 4.22(1H), 4.4–6.0(1H), 5.21(2H), 7.11(1H), 7.23(4H), 7.32(1H), 8.19(1H) |
| 136 | 1 | Me | Me |  | COOH | 5 | $C_{24}H_{30}O_4$ | 133–134 | 1.30(8H, m), 1.96(6H, s), 2.04(3H, s), 2.19(6H, s), 2.26(2H, m), 4.20(1H, t), 6.99(3H, m) |
| 137 | 1 | Me | Me |  | COOH | 5 | $C_{23}H_{28}O_4$ | 110–111 | 1.40(8H, m), 1.99(5H, s), 2.02(3H, s), 2.28(3H, s), 2.29(2H, m), 4.26(1H, t), 7.08(4H, m) |
| 138 | 1 | —CH=CH—CH=CH— | | | COOH | 5 | $C_{26}H_{28}O_4$ | 162–163 | 1.40(8H, m), 2.19(9H, s), 2.28(2H, m), 4.40(1H, t), 7.05(3H, m), 7.70(2H, m), 8.06(2H, m) |

TABLE 1-continued

| Compound No. | Prepared by the procedure by Example | R¹ | R² | R⁴ | R⁵ | n | Molecular formula | Melting point (°C.) Physical properties | Nuclear Magnetic resonance spectrum, δ value (ppm). TMS as internal standard |
|---|---|---|---|---|---|---|---|---|---|
| 139 | 1 | —CH=CH—CH=CH— | | (3,4-dimethoxyphenyl) | COOH | 5 | $C_{26}H_{28}O_6$ | 118–119 | 1.35(8H, m), 2.22(3H, s), 3.83(6H, s), 4.39(1H, s), 7.83(3H, m), 7.59(2H, m), 8.03(2H, m) |
| 140 | 1 | MeO | MeO | (3,4-dimethoxyphenyl) | COOH | 5 | $C_{24}H_{30}O_8$ | 86–87 | 1.38(8H, m), 2.04(3H, s), 2.30(2H, m), 3.83(9H, s), 4.16(1H, t), 6.76(3H, m) |
| 141 | 1 | MeO | MeO | (5-methylthiophen-2-yl) | COOH | 5 | $C_{21}H_{26}O_6S$ | 55–56 | 1.40(8H, m), 2.02(3H, s), 2.30(2H, m), 2.36(3H, s), 3.95(6H, s), 4.31(1H, t), 6.58(2H, m) |
| 142 | 1 | MeO | MeO | (indanyl) | COOH | 5 | $C_{25}H_{30}O_6$ | 99–100 | 1.40(8H, m), 2.04(3H, s), 2.25(4H, m), 2.85(4H, m), 3.96(6H, s), 4.22(1H, t), 7.07(3H, m) |
| 143 | 1 | MeO | MeO | (4-methoxyphenyl) | COOH | 5 | $C_{23}H_{28}O_7$ | 103–104 | 1.40(8H, m), 2.01(3H, s), 2.26(2H, m), 3.74(3H, s), 3.93(6H, s), 4.19(1H, t), 6.78(2H, m), 7.18(2H, m) |
| 144 | 10 | Me | Me | (phenyl) | CH≡CCH₂OH | 5 | $C_{24}H_{28}O_3$ | oil | 1.1–1.6(6H), 1.78(1H), 1.9–2.1(4H), 1.98(6H), 2.05(3H), 4.23(2H), 4.32(1H), 7.26(5H) |

*d₆-DMSO

EXAMPLE 31

By a similar manner to Example 8, methyl 7-(3,5,6-trimethyl-1,4-benzoquinon-2-yl)-7-phenyl heptanoate (oil) was obtained by esterifying Compound No. 50 with methanol.

NMR spectrum δ: 1.1-1.8 (6H), 1.9-2.3 (2H), 1.97 (6H),
2.04 (3H), 2.28 (2H), 3.63 (3H),
4.29 (1H), 7.25 (5H).

EXAMPLE 32

By a similar manner to Example 8, methyl 7-(3,5,6-trimethyl-1,4-benzoquinon-2-yl)-7-(4-methylphenyl)-heptanoate (oil) was obtained by esterifying Compound No. 93 with methanol.

NMR spectrum δ: 1.1-1.8 (6H), 1.9-2.4 (4H), 1.96 (6H),
2.04 (3H), 2.27 (3H), 3.63 (3H),
4.23 (1H), 7.04 (2H), 7.17 (2H).

EXAMPLE 33

Compound No. 50 (0.35 g, 1.0 mmole) was dissolved in ethyl acetate (7 ml), and 5% pd-C (35 mg) was added to the solution. The mixture was subjected to catalytic reduction at room temperature for 2 hours. The catalyst was filtered out and the solvent was distilled off. The residue was subjected to recrystallization from ethyl acetate-isopropyl ether to give 2.0 g of 7-(3,5,6-trimethyl-1,4-hydrobenzoquinon-2-yl)-7-phenylheptanoic acid. Melting point: 169°-172° C.

EXAMPLE 34

By a similar manner to Example 33, 7-(3,5,6-trimethyl-1,4-hydrobenzoquinon-2-yl)-7-(4-fluorophenyl) heptanoic acid was obtained from Compound No. 87. Melting point: 167°-169° C.

EXAMPLE 35

By a similar manner to Example 33, 7-(3,5,6-trimethyl-1,4-hydrobenzoquinon-2-yl)-7-(4-methylphenyl) heptanoic acid was obtained from Compound No. 93. Melting point: 172°-176° C.

EXAMPLE 36

Compound No. 50 (7.08 g, 20 mmole) was dissolved in ethyl acetate (142 ml), and L-(−)-α-phenylethylamine (2.57 ml, 20 mmole) was added dropwise to the solution at room temperature over 5-minutes The mixture was vigorously stirred for one hour. The resulting crystals were collected by filtration and suspended in ethyl acetate (100 ml). To the suspension was added 1N-hydrochloric acid (30 ml), and the mixture was stirred for 15 minutes. The ethyl acetate layer was separated, washed with aqueous sodium chloride solution and dried (magnesium sulfate). The solvent was distilled off to give dextrorotatory rich compound.

The compound obtained above was repeated by the above procedure four times to give optically active compound of dextrorotatory form, $[\alpha]_D^{22} = +23.6°$ (C=1, chloroform).

The compound thus obtained was subjected to recrystallization from ethanol (6.8 ml), the resulting precipitates were filtered out and the solvent was distilled off. The resultant was subjected to crystallization from isopropyl ether to give (+)-7-(3,5,6-trimethyl-1,4-benzoquinon-2-yl)-7-phenylheptanoic acid (1.10 g) yield: 16%, $[\alpha]_D^{22} = +24.4°$ (C=1, chloroform), Melting point: 79°-82° C.

By a similar manner to the above procedure, (−)-7-(3,5,6-brimethyl-1,4-benzoquinon-2-yl)-7-phenylheptanoic acid (1.20 g) was obtained from Compound No. 50 (7.08 g) by using D-(+)-α-phenylethylamine. Yield: 17%, $[\alpha]_D^{22} = -24.4°$ (C=1, chloroform), Melting point: 79°-82° C.

EXAMPLE 37

(Pharmaceutical Composition)

| A) Capsule | |
|---|---|
| (1) Compound No. 93 | 50 mg |
| (2) Cellulose fine powder | 30 mg |
| (3) Lactose | 37 mg |
| (4) Magnesium stearate | 3 mg |
| Total | 120 mg |

All the materials were mixed and filled into a gelatin capsule.

| B) Soft Capsule | |
|---|---|
| (1) Compound No. 22 | 50 mg |
| (2) Corn Starch oil | 100 mg |
| Total | 150 mg |

A mixed solution of (1) and (2) was prepared and filled into a soft capsule by a conventional manner.

| C) Tablet | |
|---|---|
| (1) Compound No. 50 | 50 mg |
| (2) Lactose | 34 mg |
| (3) Corn starch | 10.6 mg |
| (4) Corn starch (gelatinized) | 5 mg |
| (5) Maganesium stearate | 0.4 mg |
| (6) Calcium carboxymethyl cellulose | 20 mg |
| Total | 120 mg |

All the materials were mixed and compressed by a tableting machine to prepare a tablet in accordance with a conventional manner.

EXAMPLE 38

(Compound 145)

To a stirred solution of 7-(3,5,6-trimethyl-1,4-benzoquinon-2-yl)-7-phenylheptanoic acid (7.08 g, 20 mmoles) and p-nitrophenol (3.06 g, 22 mmoles) in dichloromethane (70 ml) was added dicyclo-hexylcarbodiimide (4.53 g, 22 mmoles) during 5 min. in an ice-water bath. The solution was continued to stir for 30 min. at the same conditions and then for an hour at room temperature. After the reaction was completed, the solvent was evaporated in a reduced pressure. To the residue was added ethyl acetate (50 ml) and the mixture was allowed to stand for 17 hours at 0° C. ~ −5° C. The insoluble product was filtered off and the filtrate was dried with magnesium sulfate. After the solvent was evaporated, the crystalline mass was crystallized from isopropyl ether to p-nitrophenyl 7-(3,5,6-trimethyl-1,4-benzoquinon-2-yl)-7-phenylheptanoate (8.65 g, 91%). The physical data are listed in Table 1-b.

EXAMPLE 39

(Compound 146)

To a stirred solution of p-nitrophenyl 7-(3,5,6-trimethyl-1,4-benzoquinon-2-yl)-7-phenyl-heptanate (0.71 g, 1.5 mmoles) in tetrahydrofuran (7 ml) was added concentrated ammonia (1.0 ml) at room temperature and kept stirring for 4 hours. After the reaction was completed, the solvent was evaporated in a reduced pressure. To the residue was added aqueous potassium carbonate and then extracted with ethylacetate. The organic layer was washed with water, dried over magnesium sulfate. Evaporation of the solvent gave 7-(3,5,6-trimethyl-1,4-benzoquinon-2-yl)-7-phenylheptanamide (0.46 g, 87%)

According to the above example, Compound No. 147 to 162 were prepared The physical data are listed in Table 1-b.

EXAMPLE 40

(Compound 163)

A solution of p-nitrophenyl 7-(3,5,6-trimethyl-1,4-benzoquinon-2-yl)-7-phenyl-heptanoate (0.50 g, 1.05 mmoles) and 4-(2-phenylethyl)piperazine (0.20 g, 1.05 mmoles) in dichloromethane was allowed to stand at room temperature under stirring for 18 hours. After the solvent was evaporated in a reduced pressure, the residue was dissolved in ethylacetate and the solution was washed with aqueous potassium carbonate and water, and dried over magnesium sulfate. The solvent was evaporated and the residue was chromatographed on silica gel column with ethylacetate followed by chloroform-methanol (10:1) as eluant to give 4-[7-(3,5,6-trimethyl-1,4-benzoquinon-2-yl)-7-phenylheptanoyl]-(2-phenylethyl)piperazine (0.51 g, 92%) as an oil.

The physical data are listed in Table 1-b.

EXAMPLE 41

(Compound 164)

To a mixture of p-nitrophenyl 7-(3,5,6-trimethyl-1,4-benzoquinon-2-yl)-7-phenylheltanoate (0.95 g, 20 mmoles) was added a solution of triethylamine (0.29 ml, 2.1 mmoles) in dichloromethane (10 ml) with stirring at room temperature for 2.5 days. After removal of the solvent in a reduced pressure, the residue was dissolved in ethylacetate. The solution was washed with water and saturated sodium chloride solution, dried over magnesium sulfate, and evaporated. The residue was chromatographed on silica gel column with isopropylether followed by ethylacetate-isopropylether (1:1) as eluant to give benzyl 7-(3,5,6-trimethyl-1,4-benzoquinon-2-yl)-7-phenylheptanoylglycinate (0.78 g, 78%) as an oil.

The physical data are listed in Table 1-b.

EXAMPLE 42

(Compound 165)

Benzyl 7-(3,5,6-trimethyl-1,4-benzoquinon-2-yl)-7-phenylheptanoylglycinate (0.78 g) in ethanol (8 ml) was hydrogenated in the presence of 5% palladium-charcoal (0.08 g) at room temperature. After the reaction was completed, the catalyst was removed by filtration. The solution was treated with ferric chloride (0.51 g) in water (5 ml) at room temperature for 20 min. with stirring. The reaction mixture was worked up in the usual manner. The product was recrystallized from ethylacetate to give 7-(3,5,6-trimethyl-1,4-benzoquinon-2-yl)-7-phenylheptanoylglycine (0.63 g, 98%), mp 162°–164° C.

According to the above examples 41 and 42, compound No. 166 to 172 were prepared. The physical data are listed in Table 1-b.

EXAMPLE 43

(Compound 173)

To a mixture of benzyl 7-(3,5,6-trimethyl-1,4-benzoquinon-2-yl)-7-phenylheptanoylglycinate (0.95, 2.0 mmoles) and L-proline (0.24 g, 2.1 mmoles) was added a solution of N-ethylmorpholine (0.48 g, 4.2 mmoles), in dimethylformamide (10 ml) at room temperature. After 15 hours, 1N hydrochloric acid (5 ml) was added to the reaction mixture. The product was extracted with ethylacetate. The extract was worked up in the usual manner. The crude product was chromatographed on a reversed phase ODS column (YMC-Gel ODS, 60/200 mesh, Yamamura Chemical Co. Kyoto) with methanol-$H_2O$ (9:1) as eluant to give 7-(3,5,6-trimethyl-1,4-benzoquinon-2-yl)-7-phenylheptanoyl-L-proline (0.64 g, 71%) as an oil.

The physical data are listed in Table 1-b.

EXAMPLE 44

(Compound 176)

A mixture of (7R)-(+)-7-(3,5,6-trimethyl-1,4-benzoquinon-2-yl)-7-phenylheptanoic acid (0.71 g, 2.0 mmoles), p-bromophenacylbromide (0.56 g, 2.0 mmoles), and potassium carbonate (0.30 g, 2.2 mmole) in acetone (15 ml) was stirred for 2.5 hours at room temperature. After the reaction was completed, the solvent was evaporated in a reduced pressure, the residue was taken up in the isopropylether. Working up in the usual manner gave the crude product, which was chromatographed on silica gel column with isopropylether to give p-bromophenacyl (7R)-(+)-7-(3,5,6-trimethyl-1,4-benzoquinon-2-yl)-7-phenylheptanoate (1.09 g, 99%) as an oil.

The physical data are listed in Table 1-b.

EXAMPLE 45

(Compound 177)

To a stirred solution of (7R)-(+)-7-(3,5,6-trimethyl-1,4-benzoquinon-2-yl)-7-phenylheptanoic acid (0.71 g, 2.0 mmoles) in tetrahydrofuran (10 ml) was added a solution of ethyl chloroformate (0.24 g, 2.2 mmole) in tetrahydrofuran (2 ml) at −10° C. under argon, followed by the addition of a solution of triethylamine (0.31 ml, 2.2 mmoles) in tetrahydrofuran (2 ml) during 5 min. After 15 min., a solution of p-bromoaniline (0.36 g, 2.1 mmoles) in the same solvent (4 ml) was added to the reaction mixture. When the mixture was continued stirring at −10°~0° C. for 1 hour, the solvent was evaporated in a reduced pressure.

The residue was worked up in the usual manner to give the crude product, which was recrystallized from isopropylether to afford N-(4-bromophenyl (7R)-(+)-7-(3,5,6-trimethyl-1,4-benzoquinon-2-yl)-7-phenylheptanomide.

The physical data are listed in Table 1-b.

TABLE 1-b

[Structure: 2,3,5-trimethyl-1,4-benzoquinone with side chain –CH(C₆H₅)–(CH₂)₇–CO–R¹⁹ at position 6]

| Compound No. | Prepared by the procedure by Example | R¹⁹ | Molecular formula | Melting point (°C.) physical properties | Nuclear magnetic resonance spectrum. δ value (ppm), TMS as internal standard |
|---|---|---|---|---|---|
| 145 | 38 | –O–C₆H₄–NO₂ (para) | C₂₈H₂₉NO₆ 475.54 | 86–88 | 1.1–1.9(6H), 1.98(6H), 2.0–2.4, 2.06(3H), 2.57(2H), 4.32(1H), 7.24(2H), 7.25(5H), 8.24(2H). |
| 146 | 39 | –NH₂ | C₂₂H₂₇NO₃ 353.46 | 105–106 | 1.1–1.8(6H), 1.9–2.4(4H), 1.97(6H), 2.04(3H), 4.29(1H), 5.95(2H), 7.24(5H). |
| 147 | 39 | –NH-i-C₃H₇ | C₂₅H₂₇NO₃ 395.54 | 99–101 | 1.11(6H), 1.1–1.8(6H), 1.9–2.3(4H), 1.96(6H), 2.03(3H), 4.05(1H), 4.29(1H), 5.50(1H), 7.23(5H) |
| 148 | 39 | 4-carbamoylpiperidin-1-yl (–N(piperidine)–CONH₂) | C₂₈H₃₆N₂O₄ 464.61 | oil | 1.1–1.8(6H), 1.7–2.4(9H), 1.97(6H), 2.03(3H), 2.65(1H), 3.02(1H), 3.86(1H), 4.28(1H), 4.54(1H), 5.78(2H), 7.24(5H) |
| 149 | 39 | 4-(diphenylaminomethyl)piperidin-1-yl (–N(piperidine)–NCHPh₂) | C₃₉H₄₄N₂O₃ 588.79 | oil | 1.1–1.8(6H), 1.9–2.3(4H), 1.95(6H), 2.02(3H), 2.34(4H), 3.42(2H), 3.59(2H), 4.22(1H), 4.28(1H), 7.1–7.5(15H) |

TABLE 1-b-continued

[Structure: quinone with CH3 groups and CH—(CH2)5CO—R19 substituent, phenyl group]

| Compound No. | Prepared by the procedure by Example | R19 | Melting point (°C.) physical properties | Molecular formula | Nuclear magnetic resonance spectrum, δ value (ppm), TMS as internal standard |
|---|---|---|---|---|---|
| 150 | 39 | [imidazole-ribose-piperazine structure] | amorphous | C36H44N6O7 672.78 | 1.1–1.8(6H), 1.9–2.4(4H), 1.95(6H), 2.03(3H), 3.58(4H), 3.5–4.5(10H), 4.8–5.2(1H), 4.94(1H), 5.81(1H), 7.23(5H), 7.86(1H), 8.14(1H) |
| 151 | 39 | [2-methoxyphenyl-piperazine] | oil | C33H40N2O4 528.69 | 1.1–1.8(6H), 1.9–2.4(4H), 1.97(6H), 2.05(3H), 3.00(4H), 3.61(2H), 3.86(3H), 3.77(2H), 4.30(1H), 6.92(4H), 7.26(5H) |
| 152 | 39 | [4-fluorobenzyl-piperazine] | oil | C33H40FN2O3 530.68 | 1.1–1.8(6H), 1.9–2.4(4H), 1.97(6H), 2.04(3H), 2.37(4H), 3.41(2H), 3.45(2H), 3.58(2H), 4.29(1H), 6.98(4H), 7.1–7.4(2H), 7.25(5H) |
| 153 | 39 | [benzyl-piperazine] | oil | C33H40N2O3 512.69 | 1.1–1.8(6H), 1.9–2.4(4H), 1.97(6H), 2.03(3H), 2.38(4H), 3.41(2H), 3.48(2H), 3.59(2H), 4.29(1H), 7.24(5H), 7.30(5H) |

TABLE 1-b-continued
[Structure shown at top of table]
| Compound No. | Prepared by the procedure by Example | R[19] | Molecular formula | Melting point (°C.) physical properties | Nuclear magnetic resonance spectrum, δ value (ppm), TMS as internal standard |
|---|---|---|---|---|---|
| 154 | 39 | 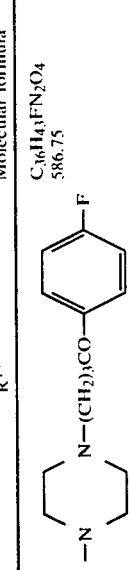 | $C_{36}H_{43}FN_2O_4$ 586.75 | oil | 1.1–1.8(6H), 1.8–2.5(12H), 1.98(6H), 2.04(3H), 2.97(2H), 3.37(2H), 3.51(2H), 4.30(1H), 7.12(2H), 7.26(5H), 7.99(2H) |
| 155 | 39 | 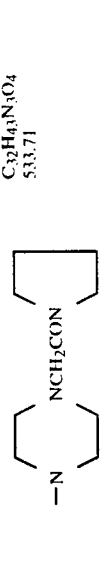 | $C_{32}H_{43}N_3O_4$ 533.71 | oil | 1.1–1.8(6H), 1.7–2.4(8H), 1.97(6H), 2.04(3H), 2.54(4H), 3.13(2H), 3.3–3.7(8H), 4.29(1H), 7.25(5H) |
| 156 | 39 | 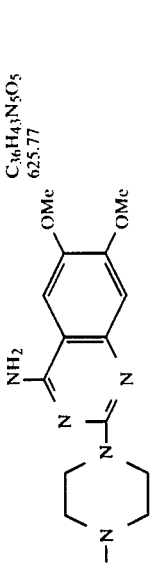 | $C_{36}H_{43}N_5O_5$ 625.77 | 207–209 | 1.1–1.8(6H), 1.9–2.4(4H), 1.95(6H), 2.02(3H), 3.4–4.0(8H), 3.87(3H), 3.94(3H), 4.30(1H), 5.40(2H), 6.90(2H), 7.24(5H) |
| 157 | 39 | 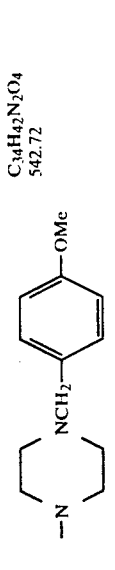 | $C_{34}H_{42}N_2O_4$ 542.72 | oil | 1.1–1.8(6H), 1.9–2.4(4H), 1.96(6H), 2.03(3H), 2.36(4H), 3.39(2H), 3.42(2H), 3.59(2H), 3.77(3H), 4.30(1H), 6.83(2H), 7.21(5H), 7.24(5H) |
| 158 | 39 | 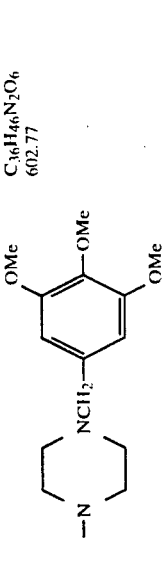 | $C_{36}H_{46}N_2O_6$ 602.77 | oil | 1.1–1.8(6H), 1.9–2.4(4H), 1.96(6H), 2.03(3H), 2.39(4H), 3.3–3.7(4H), 3.41(2H), 3.82(3H), 3.85(6H), 4.29(1H), 6.55(2H), 7.24(5H) |

TABLE 1-b-continued

Structure:

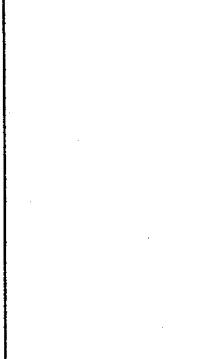

| Compound No. | Prepared by the procedure by Example | R[19] | Molecular formula | Melting point (°C.) physical properties | Nuclear magnetic resonance spectrum. δ value (ppm), TMS as internal standard |
|---|---|---|---|---|---|
| 159 | 39 | 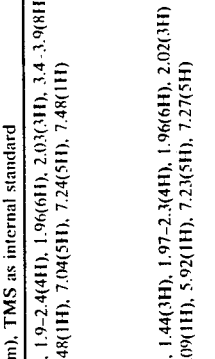 | C₃₁H₃₆N₂O₅ 516.64 | oil | 1.1–1.8(6H), 1.9–2.4(4H), 1.96(6H), 2.03(3H), 3.4–3.9(8H), 4.31(1H), 6.48(1H), 7.04(5H), 7.24(5H), 7.48(1H) |
| 160 | 39 | *1 —HNCHMe (S) —Ph | C₃₀H₃₅NO₃ 457.61 | oil | 1.1–1.8(6H), 1.44(3H), 1.97–2.3(4H), 1.96(6H), 2.02(3H), 4.26(1H), 5.09(1H), 5.92(1H), 7.23(5H), 7.27(5H) |
| 161 | 39 | *2 —NHCHMe (S) —Ph | C₃₀H₃₅NO₃ 457.61 | oil | 1.1–1.8(6H), 1.45(3H), 1.9–2.3(4H), 1.96(6H), 2.02(3H), 4.27(1H), 5.10(1H), 5.91(1H), 7.22(5H), 7.27(5H) |
| 162 | 39 | —NHCHMe (S) -naphthyl | C₃₄H₃₇NO₃ 507.67 | oil | 1.1–1.8(6H), 1.59(3H), 1.9–2.3(4H), 1.93(6H), 2.00(3H), 4.23(1H), 5.95(1H), 6.00(1H), 7.23(5H), 7.3–7.5(4H), 7.78(2H), 8.07(1H) |
| 163 | 40 | 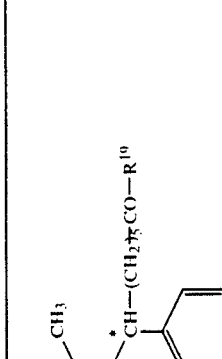 NCH₂CH₂— N(piperidine) | C₃₄H₄₂N₂O₃ 526.72 | oil | 1.1–1.8(6H), 1.9–2.9(12H), 1.97(6H), 2.04(3H), 3.46(2H), 3.63(2H), 4.30(1H), 7.22(5H), 7.24(5H) |
| 164 | 41 | —GlyOBzl | C₃₁H₃₅NO₅ 501.62 | oil | 1.1–1.8(6H), 1.9–2.3(4H), 1.98(6H), 2.05(3H), 4.07(2H), 4.30(1H), 5.19(2H), 6.03(1H), 7.28(5H), 7.39(5H) |

TABLE 1-b-continued

Structure:
```
        O
        ‖
   CH₃     CH₃
      ╲   ╱
       [ring]        CH₃
      ╱   ╲          |
   CH₃     C—CH—(CH₂)₇CO—R¹⁹
        ‖      |
        O    phenyl
```

| Compound No. | Prepared by the procedure by Example | R¹⁹ | Molecular formula | Melting point (°C.) physical properties | Nuclear magnetic resonance spectrum, δ value (ppm), TMS as internal standard |
|---|---|---|---|---|---|
| 165 | 42 | —GlyOH | C₂₄H₂₉NO₅ 411.50 | oil | 1.1–1.8(6H), 1.9–2.3(4H), 1.97(6H), 2.03(3H), 4.02(2H), 4.28(1H), 5.39(1H), 7.23(5H), 7.60(1H). |
| 166 | 41 | —Arg(NO₂)OBzl | C₃₅H₄₃N₅O₇ 645.76 | oil | 1.1–1.9(10H), 1.9–2.5(6H), 1.95(6H), 2.02(3H), 3.30(2H), 4.27(1H), 4.64(1H), 5.15(2H), 6.55(1H), 7.24(5H), 7.32(5H), 7.68(2H), 8.32(1H). |
| 167 | 42 | —ArgOH.HCl | C₂₈H₃₈N₄O₅.HCl 547.10 | Amorphous | 1.0–1.8(10H), 1.9–2.4(6H), 1.93(3H), 1.99(3H), 3.27(2H) 4.24(1H) 4.48(1H), 6.8–7.2(1H), 7.29(5H), 7.63(1H), 8.13(3H) |
| 168 | 41,42 | —HisOH | C₂₈H₃₃N₃O₅ 491.59 | Amorphous | 1.0–1.7(6H), 1.9–2.3(4H), 1.93(6H), 1.99(3H), 3.09(2H), 4.23(1H), 4.48(1H), 6.90(1H), 7.0–7.5(6H), 8.26(1H) 11.24(2H) |
| 169 | 41 | —Asp(OBzl)OBzl | C₄₀H₄₃NO₇ 649.78 | oil | 1.1–1.8(6H), 1.9–2.3(4H), 1.96(6H), 2.04(3H), 2.95(2H), 4.28(1H), 4.89(1H), 5.04(2H), 5.12(2H), 6.48(1H), 7.25(5H), 7.30(10H). |
| 170 | 42 | —AspOH | C₂₆H₃₁NO₇ 469.53 | Amorphous | 1.1–1.8(6H), 1.9–2.3(4H), 1.96(6H), 2.03(3H), 2.92(2H) 4.27(1H), 4.83(1H), 6.62(2H), 6.97(1H), 7.24(5H) |
| 171 | 41 | —Glu(OBzl)OBzl | C₄₁H₄₅NO₇ 663.81 | oil | 1.1–1.8(6H), 1.8–2.5(8H), 1.96(6H), 2.04(3H), 4.27(1H), 4.64(1H), 5.07(2H), 5.14(2H), 6.18(1H), 7.25(5H) 7.33(10H). |
| 172 | 42 | —GluOH | C₂₇H₃₃NO₇ 483.56 | Amorphous | 1.1–1.8(6H), 1.9–2.6(8H), 1.95(6H), 2.03(3H), 4.27(1H), 4.59(1H), 6.86(1H), 7.21(5H), 8.23(2H). |
| 173 | 43 | —ProOH | C₂₇H₄₁NO₅ 451.56 | oil | 1.1–1.8(6H), 1.9–2.4(8H), 1.97(6H), 2.03(3H), 3.50(2H), 4.30(1H), 4.54(1H), 7.1–7.5(5H) |
| 174 | 41 | —PheOBzl | C₃₈H₄₁NO₅ 591.75 | oil | 1.1–1.8(6H), 1.9–2.3(4H), 1.96(6H), 2.02(3H), 3.09(2H), 4.27(1H), 4.92(1H), 5.13(2H), 5.84(1H), 6.9–7.4(5H) 7.24(5H), 7.32(5H) |
| 175 | 42 | —PheOH | C₃₁H₃₅NO₅ 501.62 | Amorphous | 1.1–1.8(6H), 1.9–2.3(4H), 1.96(6H), 2.03(3H), 3.14(2H), 4.26(1H), 4.83(1H), 6.15(1H), 7.17(5H), 7.23(5H), 7.39(1H) |
| 176 | 44 | *1 —OCH₂CO—⟨C₆H₄⟩—Br | C₃₀H₃₁BrO₅ 551.48 | oil | 1.1–1.8(6H), 1.9–2.3(2H), 1.96(6H), 2.04(3H), 2.44(2H), 4.30(1H), 5.23(2H), 7.23(2H), 7.57(2H), 7.74(2H) |
| 177 | 45 | *2 —NH—⟨C₆H₄⟩—Br | C₂₈H₃₀BrNO₃ 508.46 | 163–164 | 1.1–1.9(6H), 1.9–2.4(4H), 1.96(6H), 2.03(3H), 4.29 (1H), 7.23(5H), 7.38(4H). |

In the column of R¹⁹ in the above table, *1 means optical isomer (R)-(+) and *2 means (S)-(-), and "Gly", "Arg", "His", "Asp", "Pro", "Phe", and "Bzl" mean "glycyl", "arginyl", "histidyl", "asparagyl", "prolyl", "phenylalanyl" and "benzyl", respectively.

EXPERIMENTAL EXAMPLE 1

5-Lipoxygenase Inhibitory Activity $10^7$ RBL-1 cells (rat basophilic leukemia cells) were suspended in 0.5 ml of MCM (mast cell medium), and test solutions (made up of 0.5 ml of MCM, 50 µg of arachidonic acid, 10 µg of A 23187 (calcium ionophore, Eli Lilly) and 1 µM, 0.1 µM, 0.01 µM and 0.001 µM as the final concentration of the quinone compound, respectively) prepared previously were added respectively to the suspension, followed by reaction at 37° C. for 20 minutes. After the conclusion of the reaction, 4 ml of ethanol and 1,4-dimethoxy-2-methyl-3-(3-methoxypropyl)naphthalene as the internal reference drug were added to the reaction solution, and the mixture was shaken thoroughly and allowed to stand at room temperature for 10 minutes. Then, it was centrifuged (2000 r.p.m.) for 10 minutes, and the supernatant fluid was separated and concentrated to dryness under reduced pressure. 0.5 Milliliter of 60% aqueous methanol was added to the concentrate, and 100 µl of the resulting solution was taken and subjected to high-performance liquid chromatography to determine amount of 5-HETE (5-hydroxyeicosatetraenoic acid). Determination of 5-HETE was made through measurement of an absorption at 237 nm with a UV absorption monitor.

The 5-HETE production inhibitory effect (IE) was expressed by $$\left(1 - \frac{b}{a}\right) \times 100.$$

wherein a is a peak height or peak area corrected by the peak for the internal reference when the quinone compound is not contained; b is a peak height or peak area corrected by the peak for the internal reference when the quinone compound is contained.

Experiment Results

The experiment results as shown in Table 2 indicate that the quinone compounds have potent 5-HETE production inhibitory activity.

TABLE 2

| | 5-HETE production inhibiting effect | | |
|---|---|---|---|
| Comp'd. No. | 5-HETE production inhibiting effect ($IC_{50}$, $10^{-8}$M)* | Comp'd. No. | 5-HETE production inhibiting effect ($IC_{50}$, $10^{-8}$M) |
| 1 | 8 | 17 | 20 |
| 3 | 6 | 18 | 20 |
| 5 | 3 | 23 | 1.0 |
| 6 | 2.8 | 35 | 44 |
| 7 | 14 | 36 | 32 |
| 9 | 3.2 | 39 | 130 |
| 10 | 3.4 | 45 | 2.8 |
| 11 | 3.4 | 46 | 73 |
| 13 | 8 | 50 | 2.8 |
| 14 | 20 | 56 | 6.2 |
| 15 | 5 | 87 | 10 |
| 16 | 3.2 | 93 | 9 |

Note.
*The 5-HETE production inhibiting effect ($IC_{50}$) is expressed in terms of concentration ($10^{-8}$M) of drug at which the peak height or peak area for 5-HETE in the high-performance liquid chromatogram is inhibited by 50%.

EXPERIMENTAL EXAMPLE 2

Action on the Immunoglobulin-$G_1$ Mediated Bronchoconstriction Reaction in Guinea Pigs In accordance with the method of Orange and Moore (Orange, R. P. and Moore E. G., J. Immunol., 116, 392–397, 1976), female and male Hartley guinea pigs weighing about 350 g were sensitized by intraperitoneal application of an emulsion (1 ml) composed of egg albumin (1 mg) and Freund's complete adjuvant (produced by Wako Pure-Chemical Industries, Ltd. of Japan). 3 Weeks after the sensitization, a serum antibody level in the sensitized guinea pigs was measured by means of the 3-hours passive cutaneous anaphylaxis (PCA) reaction in guinea pigs. Guinea pigs, which showed positive PCA with 1000 fold-diluted serum, were used as a sensitized animal. The broncoconstriction reaction resulting from the antigen-antibody reaction was measured in accordance with the Konzett-Rössler method (Konzett, H. and Rössler, R., Naunyn-Schmiedeberg's s Arch. exp. Path. pharmak., 195, 71–74, 1940). The guinea pigs were fixed on the dorsal position under anesthesia with a urethane (1.5 g/kg given intraperitonealy). An incision was made through the trachea, which was connected to an artificial respirator (manufactured by Harvard Co.) through an endotracheal tube, with a side tube of the endotracheal tube being attached to a brochoconstricting transducer (type 7020, manufactured by Ugobasile Co.). While an air volume per ventilation was adjusted to 5 to 7 ml and an air ventilation rate was controlled at 70 times/min., with a load pressure to the lung set at 10 cm $H_2O$, the overflown air volume was recorded on Rectigraphy-8S (manufactured by Sanei Sokki Inc. of Japan) through a transducer. After 1 mg/kg of gallamine triethiodide was given intravenously to the animals, 1 mg/kg of antigen, egg albumin dissolved in physiological saline, was applied intravenously to induce a brochoconstriction reaction. The bronchconstriction reaction was recorded for the period of time of 15 minutes. A drug was suspended in 5% gum arabic solution, and given orally 1 hour before the application of the antigen. Percent inhibition of the immunoglobuin $G_1$ mediated bronchoconstriction reaction in guinea pigs are shown below in Table 3.

EXPERIMENTAL EXAMPLE 3

Acute Toxicity Test in Mice (Acute Toxicity)

1000 Milligrams per kilogram of each set specimen was applied orally to groups of 5 five-weeks old male mice of ICR breed, and a number of dead animals observed for the 7-days period was counted.

Representative examples of the above test results are also tabulated in Table 3.

TABLE 3

| Action on immunoglobulin-$G_1$ mediated bronchoconstriction reaction in guinea pigs and acute toxicity test in mice | | | |
|---|---|---|---|
| Compound No. | % Inhibition | Number of animals | Acute toxicity |
| 9 | 71* | 7 | — |
| 10 | 80** | 7 | — |
| 12 | 78** | 8 | — |
| 14 | 78** | 8 | — |
| 22 | 82* | 7 | — |
| 23 | 83* | 7 | — |
| 25 | 83** | 8 | — |
| 26 | 85* | 6 | — |
| 27 | 81* | 8 | — |

TABLE 3-continued

Action on immunoglobulin-$G_1$ mediated bronchoconstriction reaction in guinea pigs and acute toxicity test in mice

| Compound No. | % Inhibition | Number of animals | Acute toxicity |
|---|---|---|---|
| 28 | 85* | 6 | — |
| 29 | 81** | 8 | — |
| 33 | 75* | 8 | 0/5 |
| 34 | 78 | 7 | — |
| 36 | 80** | 8 | 0/5 |
| 38 | 73* | 8 | — |
| 45 | 91* | 5 | — |
| 49 | 84** | 7 | — |
| 50 | 76* | 7 | 0/5 |
| 59 | 83* | 6 | — |
| 76 | 89* | 7 | — |
| 86 | 80 | 8 | — |
| 87 | 81** | 8 | 0/5 |
| 88 | 79* | 7 | 0/5 |
| 89 | 65* | 7 | — |
| 90 | 61* | 7 | 0/5 |
| 92 | 92** | 8 | 0/5 |
| 93 | 83* | 7 | 0/5 |
| 94 | 81* | 5 | 0/5 |
| 95 | 63* | 6 | 0/5 |
| 97 | 85* | 7 | 0/5 |
| 137 | 89** | 7 | 0/5 |

Dose: 20 mg/kg (Oral administration)
*statistical significancy
*$P < 0.05$.
**$P < 0.01$
In column of Acute toxicity, the numerator means the number of dead animals and the denominator means the number of animals used in the test.

EXPERIMENTAL EXAMPLE 4

Inhibitory Action on Lipid Peroxides Production in Rat Brain Homogenates

The male SD rat brain tissue was used as 5% homogenate in phosphate-buffered solution. After incubation of the homogenate for 1 hour at 37° C., the amount of lipid peroxides produced was determined by the thiobarbituric acid method according to the description of Ohkawa et al. (Analytical Biochemistry, 95: 551, 1979)

Test compounds were used as a solution of dimethylsulfoxide. The inhibitory action on lipid peroxide production was expressed as a % inhibition as compared with the amount of production in the vehicle group. Results The results are shown in Table 4.

TABLE 4

Inhibitory action on lipid peroxides production in rat brain homogenates

| Compound No. | Inhibition at each concentration (%) | | | |
|---|---|---|---|---|
| | $10^{-7}$M | $10^{-6}$M | $10^{-5}$M | $10^{-4}$M |
| 50 | 16.7 ± 3.2 | 66.6 ± 12.4 | 100 ± 0 | — |
| α-tocopherol | — | 0 | 51.8 ± 10.2 | 46.5 ± 2.5 |

Number of experiments, n = 4–6

EXPERIMENTAL EXAMPLE 5

Anti-Edema Action in an Experimental Cerebral Infarction Model of Mongolian Gerbil Male Monglian gerbils (8-10 weeks of age) were used. Under light ether anesthesia, the right common carotid artery was ligated for 1 hour to induce experimental cerebral infarction, and then reperfused on removing the ligature. One hour after reperfusion, the animal was guillotined, the brain was excised, and divided into the left and right brain hemispheres. The wet weight of each hemisphere was determined, and then the dry weight was determined after drying for 24 hours at 96° C. The water content (%) of each hemisphere was estimated according to the following equation.

$$\text{Water content } (\%) = \frac{(\text{Wet weight} - \text{Dry weight}) \times 100}{\text{Wet weight}}$$

In addition, neurological deficit symptoms were observed during ligation-and-reperfusion periods.

Test drugs were orally administered as a gum arabic suspension 1 hour before the common carotid artery ligation under an unanesthetized condition. Results The results are shown in Table 5.

TABLE 5

Anti-edema action in an experimental cerebral infarction model of Mongolian gerbils

| Compound No. | Water content (%) | | Incidence of appearance of neurological deficit symptoms |
|---|---|---|---|
| | Normal side (left) | Infarct side (right) | |
| control | 80.1 ± 0.3 | 81.3 ± 0.9* | 5/6 |
| 50 | 79.8 ± 1.0 | 80.3 ± 1.0 | 1/6 |

*$P < 0.05$, compared with the normal side (paired-t test)

EXPERIMENTAL EXAMPLE 6

Inhibitory Action on Induction of Convulsive Seizure in an Experimental Cerebral Infarction Model of Spontaneously Hypertensive Rats Cerebral ischemia was induced by simultaneous ligation of bilateral common carotid arteries in male spontaneously hypertensive (SHR) rats (about 22 weeks of age) under light pentobarbital anesthesia. Thereafter, over about 4 hours, the behaviour was observed under conscious state.

Test drugs were orally administered as a gum arabic suspension 1 hour before the ligation of bilateral common carotid arteries under an unanesthetized condition.

TABLE 6

Inhibitory action on induction of ischemic convulsive seizure due to bilateral common carotid artery ligation in SHR rats]

| compound No. | Dose (mg/kg) | Time to appearance of convulsive seizure (min) |
|---|---|---|
| control | — | 151 ± 5 |
| 50 | 3 | 204 ± 7* |
| | 10 | 220 ± 9* |

$P < 0.05$, compared with control

EXPERIMENTAL EXAMPLE 7

Effect on LTD$_4$-Induced Brochoconstriction in Guinea Pigs

Bronchoconstriction in guinea pigs was measured by the method of Konzett-Rössler[Naunyn-Schmiedeberg's Arch. exp. Path. Pharmak., 195, 71-74(1940)]. The animals were anesthetized with urethane (1.5 g/kg, intraperitoneally) and the trachea was cannulated. The animals were artificially ventilated by means of a respirator (Harvard apparatus rodent respirator) at a rate of 70 strokes/min and a constant volume of 5-7 ml. Inflation pressure was kept constantly at 10 cm H$_2$O. Changes in overflow of air from a side-arm of the cannula were recorded on Rectigraph-8S via a bronchospasm transducer for 15 min. LTD$_4$ (10 μg/kg) was given into the carotide vein through an indwelling cannula. Each specimen suspended in a 5% gum arabic solution was also given through the same cannula 1 or 24 hrs before the LTD₄ administraction.

TABLE 7

[Effect on LTD₄-induced bronchoconstriction in guinea pigs]

| Compound No. | Dose (mg/kg) | % Inhibition 1 hr. | | 24 hrs. | |
|---|---|---|---|---|---|
| 50 | 0.313 | 58 | (7)[a] | — | |
|  | 1.25 | 77** | (7) | — | |
|  | 5 | 94** | (7) | 72** | (10) |
| 22 | 0.313 | 39 | (8) | — | |
|  | 1.25 | 85** | (8) | — | |
|  | 5 | 90** | (8) | 24 | (10) |
| 23 | 0.313 | 69* | (9) | — | |
|  | 1.25 | 80* | (8) | — | |
|  | 5 | 68* | (7) | 49* | (10) |
| 87 | 0.313 | 80* | (10) | — | |
|  | 1.25 | 89* | (10) | — | |
|  | 5 | 93** | (10) | 79* | (10) |
| 93 | 0.313 | 73* | (9) | — | |
|  | 1.25 | 83* | (8) | — | |
|  | 5 | 85** | (9) | 53* | (10) |

[a]Number of animals used.
*P < 0.05.
**P < 0.01. compared with control groups

EXPERIMENTAL EXAMPLE 8

Platelet Activating Factor (PAF)-Induced Bronchoconstriction in Guinea Pigs

Experimental procedure in this experiment was the same as that in LTD₄-induced bronchoconstriction shown in Experimental example 7. PAF is an intravenous dose of 1 μg/kg was used. Each specimen suspended in a 5% gum arabic solution was given orally one hour before the PAF administration.

TABLE 8

[Effect on PAF-induced bronchoconstriction in guinea pigs]

| Compound No. | Dose mg/kg | Number of animals | % Inhibition |
|---|---|---|---|
| 50 | 0.313 | 8 | 66** |
|  | 1.25 | 8 | 94** |
|  | 5 | 8 | 85** |
| 22 | 0.313 | 8 | 43* |
|  | 1.25 | 8 | 92** |
|  | 5 | 8 | 91** |
| 23 | 0.08 | 8 | 75** |
|  | 0.313 | 8 | 71* |
|  | 1.25 | 8 | 73** |
| 87 | 0.08 | 8 | 64** |
|  | 0.313 | 8 | 48 |
|  | 1.25 | 8 | 71* |
| 93 | 0.08 | 8 | 58 |
|  | 0.313 | 8 | 87** |
|  | 1.25 | 8 | 70** |
| 146 | 0.31 | 8 | 49.7* |
|  | 1.25 | 8 | 80.3** |
|  | 5 | 8 | 100.0** |
| 163 | 5 | 8 | 59.9* |
| 175 | 5 | 8 | 72.1* |

*P < 0.05.
**P < 0.01. compared with control groups

EXPERIMENTAL EXAMPLE 9

Ferric Nitrilotriacetate ($Fe^{3+}$-NTA)-Induced Injury of Rat Kidney

Male Wistar rats of 4 weeks old weighing about 80 g were used. Injury of kidney was induced by the method of Awai et al. [Amer. J. Pathol., 95, 663–674 (1979)]. The mixture of ferric nitrate and NTA as a ratio of 1:4 was intraperitoneally given: iron of 5 mg/kg for 3 days followed 10 mg/kg for 9 days. Twelve days later, the animals were killed. Body weight gain, urinary volume, urinary protein and wet and dry weights of kidney were measured. Drugs were suspended in a 5% gum arabic solution and given orally once a day in a dose of 20 mg/kg.

TABLE 9

[Inhibitory effect on $Fe^{3+}$—NTA-induced injury of rat kidney]

| Compound No. | Dose mg/kg | Number of rats | Urinary protein mg/day (% inhibition) | Urinary volume ml/day (% Inhibition) | body weight gain g. | Water content in kidney ml. (% Inhibition) |
|---|---|---|---|---|---|---|
| Normal | — | 6 | 5.1 | 6.8 | 68.3 ± 2.3 | 528.0 ± 8.8 |
| Control | — | 5 | 25.1 | 20 | 9.8 ± 5.4 | 713.8 ± 52.9 |
| 50 | 20 | 6 | 7.5** (88) | 8.4** (88) | 39.3 ± 7.4** | 562.7 ± 24.3* (81) |
| 93 | 20 | 5 | 23.1 (10) | 13.6 (47) | 26.2 ± 4.9 | 700.2 ± 35.6 (7) |

*P < 0.05.
**P <0.01. compared with control groups

EXPERIMENTAL EXAMPLE 10

Effects on Increased Vascular Permeability and Slow Reacting Substance of Anaphylaxis (SRS-A) Generation in Rat Reversed Passive Arthus Pleurisy The rat reversed passive Arthus pleurisy was induced by the method of Yamamoto et al. Agents Actions, 5, 374–377 (1975)]. Rats were given 1 ml of saline containing 5 mg of egg albumin intravenously followed 0.2 ml of rabbit anti-agg albumin antiserum injected into the pleural cavity. Just after that, 0.5 ml of saline contained 1% Evans blue was administered intravenously to the rats. 30 Minutes later, the animals were killed by bleeding, and the pleural cavity was rinsed with 2 ml of saline. The concentrations of the dye in the pleural exudate and the peripheral blood were measured to calculate the volume of serum infiltrated into the pleural cavity. The vascular permeability (dye concentration in pleural cavity/dye concentration in peripheral blood) was expressed as μl serum/30 min. On the other hand, the amount of SRS-A generated in the pleural cavity was determined by the following procedures. 30 Minutes after induction of the pleurisy, the aminals were killed by bleeding and the pleural cavity was rinsed with 2 ml of saline. 9 Milliliter of cold absolute ethanol were immediately added to the rinsed solution. The mixture was allowed to stand at 4° C. for 30 min. After the mixture was centrifuged at 3000 r.p.m. for 10 min, the supernatant was concentrated by evaporation. The resulting residue was dissolved in 0.5 ml of saline. The amount of SRS-A generated was bioassayed using guinea pig ileum.

TABLE 10-a

[Effects on vascular permeability during early response of rat reversed passive Arthus pleurisy]

| Dose (mg/rat) | Compound No. 50 | Compound No. 93 |
|---|---|---|
|  | % Inhibition |  |
| 0.1 | 21 | 14 |
| 1 | 47** | 43 |

**P < 0.01, compared with control groups

TABLE 10-b

[Effects on SRS-A generation in rats pleural exudate during early response of rat reversed passive Arthus pleurisy]

| Dose (mg/rat) | Compound No. 50 | Compound No. 93 |
|---|---|---|
|  | % Inhibition |  |
| 0.1 | 49 | −6 |
| 1 | 77** | 56** |

*P < 0.01, compared with control groups

EXPERIMENTAL EXAMPLE 11

Superoxide ($O_2^-$) Production in Guinea Pig Peritoneal Macrophages

Male Hartley guinea pigs weighing 400–450 g were given intraperitoneally 5 ml of liquid paraffin. Four days later, 15 ml of Hank's buffer were administered into the peritoneal cavity for harvest of peritoneal cells. Macrophages in the peritoneal cells were purified by the method of Wood, P. R. [J. Immunol. Methods, 28, 117–124 (1979)].

The purity of macrophages was more than 95%. The reaction mixture contained 75 μl of macrophages ($1 \times 10^7$ cells/ml), 5 μl of luminol, 10 μl of phorbol myristate acetate and 10 μl of drugs in a total volume of 100 μl. $O_2^-$ Product was assayed by chemiluminescence. Drugs were dissolved in a 10% dimethyl sulfoxide.

TABLE 11

[Inhibitory effect on $O_2^-$ production in guinea pigs peritoneal macrophages]

| Compound No. | Concentration (M) | % Inhibition |
|---|---|---|
| 93 | $10^{-6}$ | 9 ± 6 |
|  | $10^{-5}$ | 33 ± 12 |
|  | $10^{-4}$ | 91 ± 3 |
| 50 | $10^{-6}$ | 16 ± 6 |
|  | $10^{-5}$ | 38 ± 3 |
|  | $10^{-4}$ | 88 ± 2 |
| dl-α-tocophenol | $10^{-5}$ | 3 ± 2 |
|  | $10^{-4}$ | 11 ± 6 |

Number of experiments: 3

EXPERIMENTAL EXAMPLE 12

Slow Reacting Substance of Anaphylaxis (SRS-A) Generation in Rat Peritoneal Cavity Generation of SRS-A in rat peritoneal cavity was determined by the method of Orange et al. [J. Immunol., 105, 1087–1095 (1970)] Rat-anti-egg albumin antiserum wad diluted twice with saline, and 2 ml of it was intraperitoneally given to the rat. Two hours later, egg albumin 2 mg in 5 ml of Tyrode solution containing heparin (50 μl/ml) and gelatin (0.1%) was intraperitoneally administered. Fifteen minutes after the antigen challenge, the animals were killed by bleeding under ether anesthesia and the solution given into the peritoneal cavity was harvested. The solution was centrifuged at 900 g for 5 min. Two ml of the supernatent was mixed with 7 ml of cold absolute ethanol and the mixture stood for 30 min at 4° C. After centrifugation at 1,500 g for 10 min, the supernatant was evaporated. The residue was dissolved in 1 ml of saline. Amount of SRS-A was bioassayed using guinea pig ileum. Drug dissolved in a 1% dimethylsulfoxide was intraperitoneally given 1 min before the antigen challenge.

TABLE 12

[Effects on the immunologically stimulated generation of SRS-A in the rat peritoneal cavity]

| Compounds No. | Dose mg/kg | Number of rats | SRS-A generation ($LTD_4$ ng/rat) | Inhibition (%) |
|---|---|---|---|---|
| Control | — | 6 | 26.5 ± 3.9 | — |
| 50 | 1 | 6 | 7.5 ± 2.0** | 72 |

**P < 0.01, compared with the control groups

EXPERIMENTAL EXAMPLE 13

Method

Luminol (3-aminophthaloylhydrazine), 10 nmole, and phorbol myristate acetate (PMA), 10 ng, were added to guinea pig peritoneal polymorphonuclear leukocytes ($1.5 \times 10^4$ cells) suspended in Hanks' balanced salt solution-HEPES buffer (pH 7.4). A total volume of the reaction mixture was 0.1 ml. The chemiluminescence resulted from release of superoxide ($O_2^-$) during 30 sec was measured continuously for 10 min at 37° C. using a chemiluminometer analyzer (Packard Pico-Lite). A peak value of the chemiluminescence was compared as an index of the release of $O_2^-$, and the chemiluminescence inhibitable by superoxide dismutase (300 μg/ml) was measured as 100%. Compound No. 50 was added immediately before the addition of PMA.

Results

Inhibitory effect of compound No. 50 on PMA-stimulated release of $O_2^-$ in guinea pig peritoneal polymorphonuclear leukocytes was studied. Compound No. 50 at the concentrations of 0.001–0.1 mM suppressed the release of $O_2^-$ in a concentration-dependent manner.

TABLE

Inhibitory effect of Compound No. 50 on PMA-stimulated release of $O_2^-$ in guinea pig peritoneal polymorphonuclear cells

|  | (mM) | % Inhibition |
|---|---|---|
| Compound No. 50 | 0.001 | 12 |
|  | 0.01 | 56 |
|  | 0.1 | 93 |

REFERENCE EXAMPLE 1

Thionyl chloride (40 ml) was added to monoethyl suberate (40 g, 0.2 mole), and the mixture was heated at 40° C. for 2 hours. After cooling, the excessive thionyl chloride was removed under reduced pressure, and the resulting oily material was dissolved in benzene (300 ml), followed by ice-cooling. Aluminum chloride (80 g, 0.6 mole) was added gradually to the mixture. The reaction solution was stirred at room temperature for 2 hours and poured into ice-water (500 ml), to which concentrated hydrochloric acid (100 ml) was added, followed by stirring. The organic layer was separated out, washed with water, dried and then concentrated The resulting carboxylic acid ethyl ester was dissolved in ethanol (200 ml), and the solution was cooled with ice. Sodium boron hydride (5 g) was added portionwise to the solution, and the reaction solution was stirred at room temperature for 1 hour. After the excessive reagent was decomposed with acetone, water (400 ml) was added, and the product was extracted with isopropyl ether. The organic layer was washed with water, dried and concentrated under reduced pressure, and the residue was dissolved in a solvent mixture of methanol (200 ml) and water (100 ml). Sodium hydroxide (15 g) was added to the solution, followed by stirring at room temprature. 2 Hours later, the reaction solution was concentrated under reduced pressure, and 2N hydrochloric acid was added to the residue to adjust to pH 4.0, followed by extraction of the product with ethyl acetate. The organic layer was washed with water, dried and concentrated under reduced pressure to give 8-hydroxy-8-phenyloctanoic acid (25 g). Its typical physical properties and nuclear magnetic resonance spectrum data are shown in Table 13.

REFERENCE EXAMPLE 2

8-Hydroxy-8-phenyloctanoic acid (25 g) was dissolved in dichloromethane (100 ml), and acetic anhydride (12 ml), pyridine (25 ml) and dimethylaminopyridine (0.1 g) were added to the solution, followed by stirring at room temperature for 3 hours. The reaction solution was washed with water and then twice with 2N hydrochloric acid, and the organic layer was washed with water, dried and concentrated under reduced pressure to give 8-acetoxy-8-phenyloctanoic acid (21 g). Its typical physical properties and nuclear magnetic resonance spectrum are shown in Table 13.

REFERENCE EXAMPLE 3

A solution of ethyl 5-(4-methoxybenzoyl)pentanoate (50 g, 0.19 mole) in ethanol (500 ml) was cooled with ice, and sodium boron hydride (10 g) was added gradually to the solution. After the reaction was allowed to proceed for 1 hour, water (200 ml) and 2N hydrochloric acid (50 ml) were added to the reaction solution, followed by concentration under reduced pressure. The resulting residue was dissolved in ethyl acetate, and the organic layer was washed with water, dried and concentrated under reduced pressure. Methanol (300 ml), water (100 ml) and sodium hydroxide (40 g) were added to the resulting residue, followed by stirring for 2 hours, and the methanol was removed under reduced pressure. The water layer was washed with isopropyl ether and then adjusted to pH 4.0 with hydrochloric acid, followed by extraction with ethyl acetate. The organic layer was washed with water, dried and concentrated under reduced pressure, and the residue was chromatographed on a silica gel column, followed by elution with isopropyl ether-ethyl acetate (1:1) to give firstly 6-ethoxy-6-(4-methoxyphenyl)hexanoic acid (21 g) and then 6-hydroxy-6-(4-methoxyphenyl)hexanoic acid (20 g).

REFERENCE EXAMPLE 4

A solution of 3-benzoylpropionic acid (35 g, 0.18 mole) in ethanol (200 ml) was cooled with ice, and sodium boron hydride (10 g, 0.26 mole) was added little by little to the solution. After stirring for 2 hours, water (200 ml) and 2N hydrochloric acid (100 ml) were added. The reaction solution was concentrated under reduced pressure, and the product was extracted with ethyl acetate. The organic layer was washed with water, dried and concentrated under reduced pressure, and the residue was dissolved in toluene (300 ml), followed by addition of D-camphor-10-sulfonic acid (0.1 g) and heating under reflux for 1 hour. After cooling, the reaction solution was washed with aqueous saturated sodium hydrogencarbonate solution and water successively, and the organic layer was dried and concentrated under reduced pressure to give 4-phenyl-4-butenolide (30 g), as an oily substance.

Nuclear magnetic resonance spectrum: $\delta 2.00-2.80$ (4H), 5.42(1H), 7.32(5H).

By following the same procedure, from 4-benzoylbutanoic acid, there was prepared 5-phenyl-5-pentanolide, as an oily substance.

Nuclear magnetic resonance spectrum: 1.30–2.20(4H), 2.40–2.70(2H), 5.40(1H), 7.30(5H).

REFERENCE EXAMPLE 5

Magnesium (1.2 g, 0.05 mole) was added to tetrahydrofuran (50 ml), and a solution of bromobenzene (8 g, 0.05 mole) in tetrahydrofuran (20 ml) was added dropwise to the mixture under stirring. After refluxing for 1 hour and cooling at −70° C., a solution of δ-valerolactone (6 g, 0.05 mole) in tetrahydrofuran (20 ml) was added dropwise to the solution. The reaction solution was stirred at −60° C. for 30 minutes, and its temperature was allowed to rise up to room temperature over the period of 1 hour. 2N hydrochloric acid and then ethyl acetate were added to the reaction solution to extract the product. The organic layer was washed with water, dried and concentrated under reduced pressure, and the residue was chromatographed on a silica gel column, followed by elution with isopropyl ether-ethyl acetate (1:1) to give 5-benzoylpentan-1-ol (5.5 g). This compound was dissolved in ethanol (50 ml), and after ice-cooling, sodium boron hydride (1.0 g) was added to the solution, followed by stirring for 1 hour. Water (50 ml) was added to the reaction solution, and the ethanol was removed under reduced pressure. The product was extracted with ethyl acetate, and the organic layer was washed with water, dried and concentrated under reduced pressure. The residue was dissolved in dichloromethane (50 ml), and pyridine (20 ml) and acetic anhydride (8 ml) were added to the solution, followed by allowing the mixture to stand at room temperature for 18 hours. Ether (100 ml) was added to the reaction solution, and the mixed solution was washed with water, 2N hydrochloric acid and water successively. The ether layer was dried and concentrated under reduced pressure to give 1-phenyl-1,6-diacetoxyhexane (6 g). Its typical physical properties and nuclear magnetic resonance spectrum data are shown in Table 13.

REFERENCE EXAMPLE 6

A 24.1 ml (38.6 mmole) of n-butyllithium.hexane solution was added dropwise to 10.0 g (38.6 mmole) of 1-bromo-2,5-dimethoxy-3,4,6-trimethylbenzene dissolved in anhydrous tetrahydrofuran (100 ml), under an atmosphere of argon at −40° C. over the period of 10 minutes, followed by stirring for another 20 minutes. Then, 3.32 g (38.6×0.6 mmole) of cuprous bromide was added, followed by stirring at −40° to −20° C. for 1 hour. After addition of a solution of 6.60 g (38.6 mmole) of benzyl bromide in tetrahydrofuran (15 ml), the cooling bath was removed, the reaction solution was stirred at 70° C. for 1 hour and cooled with ice, followed by addition of 1N hydrochloric acid (50 ml) and stirring.

The tetrahydrofuran was distilled off under reduced pressure, and isopropyl ether was added to the residue. The insoluble matter was filtered through a bed of Hyflo Supercell, and the isopropyl ether layer was separated out, washed with water and aqueous sodium chloride solution successively, dried (magnesium sulfate) and evaporated. The residual solution was distilled under reduced pressure to give 8.62 g (83%) of 1-benzyl-2,5-dimethoxy-3,4,6-trimethylbenzene, b.p.140°-142° C. (0.3 torr) and m.p. 70° to 71° C.

By following the same procedure, there were prepared 1-(4-methoxybenzyl)-2,5-dimethoxy-3,4,6-trimethylbenzene, m.p. 53°-54° C., and 1-benzyl-2-methyl-3,4,5,6-tetramethoxybenzene, bp 148°-150° C. (0 3 torr).

REFERENCE EXAMPLE 7

A 16.3 ml (26 mmole) of n-butyllithium.hexane solution was added dropwise to 7.02 g (26.0 mmole) of 1-benzyl-2,5-dimethoxy-3,4,6-trimethylbenzene and 4.32 ml (26×1.1 mmole) of 1,1,2,2-tetramethylethylenediamine dissolved in anhydrous tetrahydrofuran (70 ml), under an atmosphere of argon at 50° C. over the period of 10 minutes, followed by stirring at 50° to 56° C. for 20 minutes. Then, a solution of 5.80 g (26 mmole) of 3-bromopropanol.tetrahydropyranyl ether in tetrahydrofuran (30 ml) was added dropwise to the mixed solution over the period of 10 minutes, followed by stirring at 50° C. for further 10 minutes. After ice-cooling, a 10% aqueous phosphoric acid solution was added to make the solution acid, and isopropyl ether was added to conduct extraction. The organic layer was separated out, washed with aqueous saturated sodium chloride solution, dried (magnesium sulfate) and evaporated. The residue was dissolved in methanol (70 ml), and 0.25 g (26×1/20 mmole) of p-toluenesulfonic acid was added to the solution, followed by stirring at 70° C. for 15 minutes. After cooling by standing at room temperature, an aqueous sodium hydrogen-carbonate solution was added for neutralization, and the solvent was evaporated. Isopropyl ether and water were added to the residue to effect extraction, and the isopropyl ether layer was washed with aqueous sodium chloride solution, dried (magnesium sulfate) and evaporated. The residual solution was chromatographed on a silica gel column to effect purification (elution with isopropyl ether) to thereby give 7.00 g (82%) of 4-(2,5-dimethoxy-3,4,6-trimethylphenyl)-4-phenylbutanol. Its typical physical properties and nuclear magnetic resonance spectrum data are shown in Table 14.

REFERENCE EXAMPLE 8

A 3.1 ml (5.0 mmole) portion of n-butyllithium.hexane solution was added dropwise to 1.35 g (5.0 mmole) of 1-benzyl-2,5-dimethoxy-3,4,6-trimethylbenzene and 0.83 ml (5×1.1 mmole) of 1,1,2,2-tetramethylethylenediamine dissolved in anhydrous tetrahydrofuran (15 ml), under an atmosphere of argon at 50° C. over the period of 5 miniutes, followed by stirring at 50° to 55° C. for 25 minutes. Then, a solution of 0.83 g (5.0 mmole) of n-hexyl bromide in tetrahydrofuran (5 ml) was added dropwise to the mixed solution over the period of 5 minutes, followed by stirring at 50° C. for further 10 minutes. The reaction solution was cooled with ice and made acid by adding a 10% aqueous phosphoric acid solution, and the product was extracted with isopropyl ether. The organic layer was separated out, washed with aqueous sodium chloride solution, dried (magnesium sulfate) and evaporated. The residual solution was chromatographed on a silica gel column to effect purification (elution with hexane/isopropyl ether) to thereby give 1.37 g (77%) of 7-(2,5-dimethoxy-3,4,6-trimethylphenyl)-7-phenylheptane. Its typical physical properties and nuclear magnetic resonance specrum data are shown in Table 14.

REFERENCE EXAMPLE 9

A 9.4 ml (5.0 mmole) of n-butyllithium.hexane solution was added dropwise to 4.05 g (15 mmole) of 1-benzyl-2,5-dimethoxy-3,4,6-trimethylbenzene and 2.49 ml (15×1.1 mmole) of 1,1,2,2-tetramethylethylenediamine dissolved in anhydrous tetrahydrofuran (40 ml), under an atmosphere of argon at 50° C. over the period of 5 minutes. followed by stirring at 50° to 55° C. for 25 minutes. Then, a solution of 0.98 g (5.0 mmole) of 6-bromohexanoic acid and 0.76 ml (5.0 mmole) of 1,1,2,2-tetramethylethylenediamine in tetrahydrofuran (10 ml) was added dropwise to the mixed solution over the period of 5 minutes, followed by stirring at 50° C. for further 10 minutes. The reaction solution was cooled with ice and made acid by adding a 10% aqueous phosphoric acid solution, and the product was extracted with isopropyl ether. The organic layer was separated out, washed with aqueous saturated sodium chloride solution and extracted with 0.5N sodium hydroxide (aqueous solution)(50 ml) added. The aqueous layer was separated out, made acid by adding a 10% aqueous phosphoric acid solution, and extracted with isopropyl ether added. The isopropyl ether layer was separated out, washed with aqueous sodium chloride solution, dried (magnesium sulfate) and evaporated to give a crude product.

On the other hand, methanol (10 ml) was cooled to −10° C., and 1.08 ml (15 mmole) of thionyl chloride was added dropwise to it over the period of 10 minutes. 10 minutes later, a solution of the above crude product in methanol (10 ml) was added dropwise to the mixed solution 20 Minutes later, the cooling bath was removed, and stirring was carried out at room temperature for 30 minutes. The solvent was distilled off, and isopropyl ether and water were added to the residue to effect extraction. The isopropyl ether layer was washed with aqueous sodium chloride solution, dried (magnesium sulfate) and evaporated. The residual solution was chromatographed on a silica gel column to perform purification (elution with isopropyl ether/hexane) to thereby give 1.00 g of methyl 7-(2,5-dimethoxy-3,4,6-trimethylphenyl)-7-phenylheptanoate. Its typical properties and nuclear magnetic resonance spectrum data are shown in Table 14.

REFERENCE EXAMPLE 10

A 3.1 ml (5.0 mmole) of n-butyllithium.hexane solution was added dropwise to 1.51 g (5.0 mmole) of 1-benzyl-2,3,4,5-tetramethoxy-6-methylbenzene and 0.83 ml (5×1.1 mmole) of 1,1,2,2-tetramethylethylenediamine dissolved in anhydrous tetrahydrofuran (15 ml), under an atmosphere of argon at −5° C. over the period of 5 minutes, followed by stirring at −5° to 0° C. for 25 minutes. Then, a solution of 0.96 g (5.0 mmole) of 4-chlorobutanol.tetrahydropyranyl ether in tetrahydrofuran (5 ml) was added to the mixed solution over the period of 5 minutes, followed by stirring for further 15 minutes under ice-cooling. Subsequently, the cooling bath was removed, and stirring was effected at room temperature for 20 minutes. The reaction solution was cooled with ice, and made acid by adding a 10% aqueous phosphoric acid solution, and the product was extracted with isopropyl ether. The organic layer was separated out, washed with aqueous sodium chloride solution, dried (magnesium sulfate). The solvent was distilled off and the residue was dissolved in methanol (15 ml), followed by addition of 48 mg (5×1/20 mmole) of p-toluenesulfonic acid and stirring at 70° C. for 15 minutes. After cooling by standing at room temperature, the mixed solution was neutralized by adding an aqueous sodium hydrogen-carbonate solution, and the solvent was distilled off. Isopropyl ether and water were added to the residue to effect extraction. The isopropyl ether layer was washed with aqueous sodium chloride solution, dried (magnesium sulfate) and evaporated. The residual solution was chromatographed on a silica gel column to perform purification (elution with isopropyl ether) to thereby give 1.29 g (69%) of 5-(2,3,4,5-tetramethoxy-6-methylphenyl)-5-phenylpentane-1-ol. Its typical physical properties and nuclear magnetic resonance spectrum data are shown in Table 14.

REFERENCE EXAMPLE 11

A solution of 1.37 g (10×1.2 mmole) of methanesulfonyl chloride in dichloromethane (10 ml) was added dropwise to 3.28 g (10.0 mmole) of 4-(2,5-dimethoxy-3,4,6-trimethylphenyl)-4-phenylbutan -1-ol and 2.10 ml (10×1.5 mmole) of triethylamine dissolved in dichloromethane (30 ml) at −5° C. over the period of 30 minutes, and the reaction was continued for 20 minutes under stirring, with ice cooling. The reaction was stopped by adding cold water to the reaction solution, and the dichloromethane layer was separated out, washed with cold dilute hydrochloric acid and aqueous sodium chloride solution successively, dried (magnesium sulfate) and evaporated. The residue was dissolved in acetone (50 ml), and 4.5 g (10×3 mmole) of sodium iodide was added to the solution, followed by stirring at 50° C. for 2 hours. The acetone was distilled off, and isopropyl ether and water were added to the residue to extract the product. The isopropyl ether layer was separated out, washed with aqueous sodium chloride solution, and evaporated, and the residual solution was chromatographed on a silica gel column to perform purification (elution with hexane/isopropyl ether) to thereby give 4.07 g (93%) of 1-iodo-4-(2,5-dimethoxy-3,4,6-trimethylphenyl)-4-phenylbutane. Its typical physical properties and nuclear magnetic resonance spectrum data are shown in Table 14.

REFERENCE EXAMPLE 12

To a solution of 4.19 g (5.0 mmole) of 1-iodo-4-(2,5-dimethoxy-3,4,6-trimethylphenyl)-4-phenylbutane in dimethylsulfoxide (30 ml) was added 0.74 g (5×3 mmole) of sodium cyanide, and the mixture was stirred at 50° C. for 2 hours. The reaction solution was cooled with ice, and isopropyl ether and water were added to it, followed by stirring. The isopropyl ether layer was separated out, washed with aqueous sodium chloride solution, dried (magnesium sulfate) and evaporated. The residual solution was chromatographed on a silica gel column to perform purification (elution with isopropyl ether/hexane) to thereby give 1.65 g (98%) of 5-(2,5-dimethoxy-3,4,6-trimethylphenyl)-5-phenylvaleronitrile. Its typical physical properties and nuclear magnetic resonance spectrum data are shown in Table 14.

REFERENCE EXAMPLE 13

In ethanol (10 ml) was dissolved 1.01 g (3.0 mmole) of 5-(2,5-dimethoxy-3,4,6-trimethylphenyl)-5-phenylvaleronitrile, and 3N sodium hydroxide (10 ml) was added to the solution, followed by stirring at 90° C. overnight (15 hours). After cooling by standing at room temperature, the ethanol was distilled off under reduced pressure, and isopropyl ether was added to the residue. The mixture was made acid by adding a 10% aqueous phosphoric acid solution, followed by extraction. The organic layer was washed with aqueous sodium chloride solution, dried (magnesium sulfate) and evaporated, and the object compound was crystallized to give 1.06 g(99%) of 5-(2,5-dimethoxy-3,4,6-trimethylphenyl)-5-phenylvaleric acid, m.p. 142°–143° C. Its typical physical properties and nuclear magnetic resonance spectrum data are shown in Table 14.

REFERENCE EXAMPLE 14

A 2.40 g (4.0×6 mmole) quantity of thoroughly dried chromium trioxide was carefully added little by little to anhydrous pyridine at 15° to 20° C. under stirring, and an orange to yellow mush-like solution was prepared. A solution of 1.42 g (4.0 mmole) of 6-(2,5-dimethoxy-3,4,6-trimethylphenyl)-6-phenylhexan -1-ol in pyridine (10 ml) was added to the solution, followed by stirring at room temperature overnight (16 hours). The reaction solution was poured into ice-cold water, and the product was extracted with dichloromethane. The dichloromethane layer was separated out, and evaporated. Isopropyl ether and 1N hydrochloric acid were added to the residue to effect extraction, and the isopropyl ether layer was separated out, washed with aqueous sodium chloride solution and then admixed with 0.5N NaOH (50 ml) to allow the product to pass into the aqueous phase. The aqueous phase was separated out and made acid by adding a 10% aqueous phosphoric acid solution, and the carboxylic acid was extracted with isopropyl ether. The isopropyl ether layer was separated out, washed with aqueous sodium chloride solution, dried (magnesium sulfate) and evaporated. The residue was chromatographed on a silica gel column to perform purification (elution with isopropyl ether) to thereby give 1.07 g (72%) of 6-(2,5-dimethoxy-3,4,6-trimethylphenyl)-6-phenylhexanoic acid. Its typical physical properties and nuclear magnetic resonance spectrum data are shown in Table 14.

REFERENCE EXAMPLE 15

In methanol (20 ml) was dissolved 1.99 g (5.0 mmole) of 7-(2,5-dimethoxy-3,4,6-trimethylphenyl)-7-phenylheptanoic acid, and 1N sodium hydroxide (10 ml) was added to the solution, followed by stirring at 50° C. for 2 hours. After cooling by standing at room temperature, the methanol was distilled off under reduced pressure, and the residue was made acid by adding a 10% aqueous phosphoric acid solution, followed by extraction of the product with isopropyl ether. The isopropyl ether layer was separated out, washed with aqueous sodium chloride solution, dried (magnesium sulfate) and evaporated to give 1.92 g (100%) of 7-(2,5-dimethoxy-3,4,6-trimethylphenyl)-7-phenylheptanoic acid. Its typical physical properties and nuclear magnetic resonance spectrum data are shown in Table 14.

REFERENCE EXAMPLE 16

A solution of 2.24 g (12.8×1.25 mmole) of propargyl alcohol.tetrahydropyranyl ether in tetrahydrofuran (15 ml) was added dropwise to a suspension of 0.87 g (12.8×1.25×1.4 mmole) of sodium amide in anhydrous tetrahydrofuran (10 ml) under an atmosphere of argon at room temperature over the period of 5 minutes. Thereafter, the reaction temperature was raised up to 50° C., followed by stirring for 1 hour. Subsequently, the temperature was lowered to −5° C., whereby hexamethylphosphoroamide (6 ml) was added and a solution of 5.60 g (12.8 mmole) of 1-iodo-4-(2,5-dimethoxy-3,4,6-trimethylphenyl)-4-phenylbutane in tetrahydrofuran (23 ml) was added dropwise to the reaction solution over the period of 10 minutes. After stirring was continued for further 30 minutes under stirring with ice-cooling, the cooling bath was removed, and stirring was effected at room temperature for 30 minutes. The reaction solution was cooled with ice, and the reaction was suspended by adding aqueous saturated ammonium chloride solution, followed by extraction of the product with isopropyl ether added. The organic layer was separated out, washed with aqueous saturated sodium chloride solution, dried (magnesium sulfate) and evaporated.

The residue was dissolved in methanol (15 ml), followed by addition of 0.12 g (12.8×1/20 mmole) or p-toluenesulfonic acid and stirring at 70° C. solution was neutralized by adding an aqueous sodium hydrogencarbonate solution, and the solvent was distilled off. Isopropyl ether and water added to the residue to effect aqueous sodium chloride solution, dried (magnesium sulfate) and evaporated.

The residual solution was chromatographed on a silica gel column to perform purification (elution with isopropyl ether/hexane) to thereby give 4.31 g (92%) of 7-(2,5-dimetoxy-3,4,6-trimethylphenyl)-7-phenyl-2-heptyn -1-ol. Its typical physical properties and nuclear magnetic resonance spectrum data are shown in Table 14.

REFERENCE EXAMPLE 17

5% Palladium-carbon (0.2 g) was added to a solution of 1.970 g (5.0 mmole) of 9-(2,5-dimethoxy-3,4,6-trimethylphenyl)-9-phenyl-3-nonyn -1-ol in ethanol (20 ml), and catalytic reduction was conducted at room temperature for 2 hours. The catalyst was filtered out, and the ethanol was distilled off under reduced pressure. The residue was chromatographed on a silica gel column to perform purification (elution with isopropyl ether) to thereby give 1.97 g (99%) of 9-(2,5-dimethoxy-3,4,6-trimethylphenyl)-9-phenylnonanol. Its typical physical properties and nuclear magnetic resonance spectrum data are shown in Table 14.

REFERENCE EXAMPLE 18

A 0.42 g (10×1.05 mmole) quantity of sodium hydride (60%, oily preparation) was added to a solution of 1.52 g (10.0 mmole) of methyl p-hydroxybenzoate in dimethylformamide (15 ml) under ice-cooling, followed by stirring for 5 minutes. The cooling bath was removed, and a solution of 4.80 g (10.0 mmole) of 1-iodo-7-(2,5-dimethoxy-3,4,6-trimethylphenyl)-7-phenylheptane in dimethylformamide (15 ml) was added to the mixture. Then, the temperature was raised to 50° C., and stirring was effected for 1 hour. After ice-cooling, dilute hydrochloric acid was added to suspend the reaction, and the product was extracted with isopropyl ether. The isopropyl ether layer was separated out, washed with aqueous sodium chloride solution, dried (magnesium sulfate) and evaporated. The residual solution was chromatographed on a silica gel column to perform purification (elution with hexane/isopropyl ether) to thereby give 4.95 g (98%) of methyl 4-[7-(2,5-dimethoxy-3,4,6-trimethylphenyl)-7-phenylheptoxy]-benzoate. Its typical physical properties and nuclear magnetic resonance spectrum data are shown in Table 14.

REFERENCE EXAMPLE 19

A 2.1 ml (3.0×1.1 mmole) portion of n-butyllithium. hexane solution was added dropwise to a solution of 0.50 ml (3.0×1.2 mmole) of diisopropylamine in anhydrous tetrahydrofuran (5 ml) under an atmosphere of argon at −20° C. over the period of 5 minutes, followed by stirring at −20° to −5° C. for 10 minutes. The mixed solution was cooled at −20° C. and a solution of 0.38 g (3.0×1.1 mmole) of ethyl isobutyrate in tetrahydrofuran (4 ml) was added dropwise to it over the period of 5 minutes, followed by stirring at −20° to −5° C. for 20 minutes. A solution of 1.36 g (3.0 mmole) of 1-iodo-5-(2,5-dimethoxy-3,4,6-trimethylphenyl)-5-phenylpentane in tetrahydrofuran (14 ml) was added dropwise to the mixed solution over the period of 5 minutes, followed by stirring at −20° to −10° C. for 1.5 hours. After the reaction solution was cooled with ice, the reaction was suspended by adding 1N hydrochloric acid, and isopropyl ether and sodium chloride were added to extract the product. The organic layer was separated out, washed with aqueous saturated sodium chloride solution, dried (magnesium sulfate) and evaporated. The residual solution was chromatographed on a silica gel column to perform purification (elution with hexane/isopropyl ether) to thereby give 1.20 g (91%) of ethyl 7-(2,5-dimethoxy-3,4,6-trimethylphenyl)-2,2-dimethyl-7-phenylheptanoate. Its typical physical properties and nuclear magnetic resonance spectrum data are shown in Table 14.

REFERENCE EXAMPLE 20

3N Sodium hydroxide (9 ml) was added to a solution of 1.20 g (2.73 mmole) of ethyl 7-(2,5-dimethoxy-3,4,6-trimethylphenyl)-2,2-dimethyl-7-phenylheptanoate in ethanol (12 ml), followed by stirring at 90° C. overnight (15 hours). After cooling by standing at room temperature, the ethanol was distilled off under reduced pressure, and the residue was made acid by adding a 10% aqueous phosphoric acid solution, followed by extraction of the product with isopropyl ether. The isopropyl ether layer was washed with aqueous sodium hydrochloride solution, dried (magnesium suflate) and evaporated to give 1.11 q (99%) of 7-(2,5-dimethoxy-3,4,6-trimethylphenyl)-2,2-dimethyl-7-phenylheptanoic acid. Its typical physical properties and nuclear magnetic resonance spectrum data are shown in Table 14.

REFERENCE EXAMPLE 21

In methanol (90 ml) was dissolved 9.00 g (30 mmole) methyl 6-[4-(1-imidazolyl)benzoyl]hexanoate, and the solution was stirred under ice-cooling. 0.86 Gram (30×0.75 mmole) of of sodium boron hydride was added to it, and stirring was continued for 30 minutes under ice-cooling. After acetone was added, the solvent was distilled off, and chloroform and water were added to the residue to effect extraction. The chloroform layer was separated out, washed with aqueous sodium chloride solution, dried (magnesium sulfate) and evaporated to give 9.10 g (100%) of methyl 7-hydroxy-7-[4-(1-imidazolyl)phenyl]heptanoate (part of the compound was recrystallized from ethyl acetate/isopropyl ether. m.p. 77°–78° C.).

TABLE 13

$$R^4-CH-(CH_2)_{n^1}-Y^1$$
$$|$$
$$X^1$$

| Compound No. | Prepared by the procedure by Ref. Example | $R^4$ | $X^1$ | $Y^1$ | $n^1$ | Molecular formula Physical properties Melting point (°C.) | NMR spectrum TMS as internal standard (δ value, ppm) |
|---|---|---|---|---|---|---|---|
| A-1 | 1 | phenyl | OH | COOH | 6 | $C_{14}H_{20}O_3$ oil | 1.1–1.8(6H), 2.29(2H), 4.63(1H), 7.30(5H) |
| A-2 | 2 | phenyl | OCOMe | COOH | 6 | $C_{16}H_{22}O_4$ oil | 1.08–1.98(10H), 2.04(3H), 2.30(2H), 5.70(1H), 7.30(5H) |
| A-3 | 3 | 4-OMe-phenyl | OH | COOH | 4 | $C_{13}H_{18}O_4$ oil | 1.1–1.9(6H), 2.29(2H), 3.77(3H), 4.59(1H), 6.83(2H), 7.20(2H) |
| A-4 | 3 | 4-OMe-phenyl | OEt | COOH | 4 | $C_{15}H_{22}O_4$ oil | 1.16(3H), 1.1–1.95(4H), 2.31(2H), 3.26(2H), 3.78(3H), 4.13(1H), 6.84(2H), 7.19(2H) |
| A-5 | 5 | phenyl | OCOMe | OCOMe | 5 | $C_{16}H_{22}O_4$ oil | 1.10–1.98(8H), 2.00(3H), 2.03(3H), 4.00(2H), 5.71(1H), 7.30(5H) |
| A-6 | 2 | phenyl | OCOMe | COOH | 4 | $C_{14}H_{18}O_4$ oil | 1.1–1.98(6H), 2.06(6H), 2.32(2H), 5.72(1H), 7.31(5H) |
| A-7 | 2 | phenyl | OCOMe | COOH | 8 | $C_{18}H_{26}O_4$ oil | 1.1–1.98(14H), 2.07(3H), 2.37(2H), 5.71(1H), 7.33(5H) |
| A-8 | 2 | thienyl | OCOMe | COOH | 4 | $C_{12}H_{16}O_4S$ oil | 1.1–1.9(6H), 2.03(3H), 2.33(2H), 6.01(1H), 6.93(2H), 7.21(1H) |
| A-9 | 1 | phenyl | OH | COOH | 5 | $C_{13}H_{18}O_3$ oil | 1.1–1.8(8H), 2.29(2H), 4.63(1H), 7.30(5H) |
| A-10 | 1 | indanyl | OH | COOH | 6 | $C_{17}H_{24}O_3$ oil | 1.2–1.85(10H), 2.05(2H), 2.30(2H), 2.88(2H), 4.60(1H), 7.14(3H) |

TABLE 13-continued $$R^4-CH-(CH_2)_{n^1}-Y^1$$
$$\phantom{R^4-CH}|$$
$$\phantom{R^4-CH-}X^1$$

| Compound No. | Prepared by the procedure by Ref. Example | $R^4$ | $X^1$ | $Y^1$ | $n^1$ | Molecular formula Physical properties Melting point (°C.) | NMR spectrum TMS as internal standard (δ value, ppm) |
|---|---|---|---|---|---|---|---|
| A-11 | 1 | 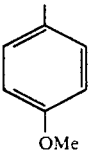 | OH | COOH | 5 | $C_{16}H_{22}O_4$ oil | 1.1–1.9(8H), 2.29(2H), 3.77(3H), 4.59(1H), 6.83(2H), 7.20(2H) |
| A-12 | 1 | 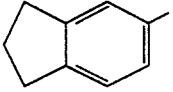 | OH | COOH | 5 | $C_{16}H_{22}O_3$ oil | 1.10–1.90(8H), 2.0(2H), 2.29(2H), 2.88(4H), 4.59(1H), 7.13(3H) |
| A-13 | 1 | 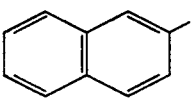 | OH | COOH | 5 | $C_{17}H_{20}O_3$ 83–85 | 1.1–1.9(8H), 2.30(2H), 5.43(1H), 7.20–8.20(7H) |
| A-14 | 1 | 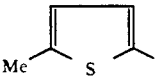 | OH | COOH | 5 | $C_{12}H_{18}O_3S$ | 1.1–1.9(8H), 2.0–2.4(2H), 2.43(3H), 4.80(1H), 6.5–6.8(2H) |
| A-15 | 2 | 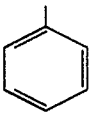 | OCOMe | COOEt | 4 | $C_{16}H_{22}O_4$ oil | 1.20(3H), 1.1–1.9(6H), 2.30(3H), 2.25(2H), 4.08(2H), 5.71(1H), 7.29(5H) |
| A-16 | 2 | 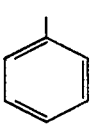 | OCOMe | COOMe | 8 | $C_{19}H_{28}O_4$ oil | 1.1–1.98(14H), 2.05(3H), 2.28(2H), 3.64(3H), 5.71(1H), 7.30(5H) |
| A-17 | 2 | 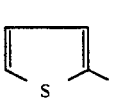 | OCOMe | COOEt | 4 | $C_{14}H_{20}O_4S$ oil | 1.22(3H), 1.1–2.2(6H), 2.03(3H), 2.27(2H), 4.07(2H), 6.01(1H), 7.00(2H), 7.24(2H) |
| A-18 | 1,2 | 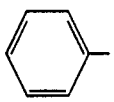 | OAc | $CO_2Et$ | 5 | $C_{17}H_{24}O_4$ | 1.2–2.0(8H), 1.22(3H), 2.03(3H), 2.24(2H), 4.09(2H), 5.70(1H), 7.29(5H) |
| A-19 | 1 | 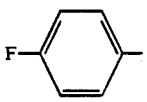 | OH | $CO_2H$ | 5 | $C_{13}H_{17}FO_3$ | 1.1–1.9(8H), 2.30(2H), 4.63(1H), 6.97(2H), 7.0–7.5(2H), 7.27(2H) |
| A-20 | 1 | 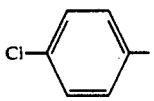 | OH | $CO_2H$ | 5 | $C_{13}H_{17}ClO_3$ 97–98 | 1.1–1.9(8H),2.29(2H), 4.61(1H), 5.83(2H), 7.24(4H) |
| A-21 | 1 | 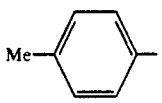 | OH | $CO_2H$ | 5 | $C_{14}H_{20}O_3$ 62–64 | 1.1–1.9(8H), 2.27(2H), 2.30(3H), 4.57(1H), 6.51(2H), 7.12(4H) |
| A-22 | 1 | 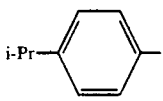 | OH | $CO_2H$ | 5 | $C_{16}H_{24}O_3$ | 1.1–1.9(8H), 1.22(6H), 2.28(2H), 2.87(1H), 4.59(1H), 6.57(2H), 7.17(4H) |

TABLE 13-continued $$R^4-\underset{\underset{X^1}{|}}{CH}-(CH_2)_{n^1}-Y^1$$

| Compound No. | Prepared by the procedure by Ref. Example | R⁴ | X¹ | Y¹ | n¹ | Molecular formula Physical properties Melting point (°C.) | NMR spectrum TMS as internal standard (δ value, ppm) |
|---|---|---|---|---|---|---|---|
| A-23 | 1 | 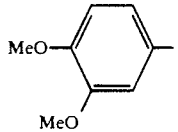 | OH | CO₂H | 5 | C₁₅H₂₂O₅ | 1.1–1.85(8H), 2.25(2H), 3.76(6H), 4.50(1H), 6.75(3H) |
| A-24 | 1 | 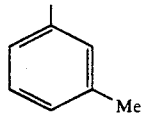 | OH | COOH | 5 | C₁₄H₂₀O₃ | 1.40(10H, m), 2.28(2H, m), 2.34(3H, s), 4.61(1H, t), 7.32(4H, m) |
| A-25 | 1 | 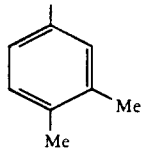 | OH | COOH | 5 | C₁₅H₂₂O₃ | 1.40(10H, m), 2.24(6H, s), 4.58(1H, t), 7.06(3H, m) |
| A-26 | 1 |  | OH | CO₂H | 7 | C₁₅H₂₂O₃ (250.34) C, 71.97; H, 8.86 oil | 1.1–1.9(12H), 2.30(2H), 4.63(1H), 7.29(5H), 7.61(2H) |
| A-27 | 1 | 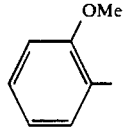 | OH | CO₂H | 5 | C₁₄H₂₀O₄ (252.31) C, 66.65; H, 7.99 oil | 1.1–1.9(8H), 2.30(2H), 3.81(3H), 4.86(1H), 6.70(2H), 6.89(2H), 7.22(2H) |
| A-28 | 1 | 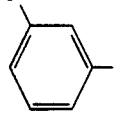 | OH | CO₂H | 5 | C₁₃H₁₇FO₃ (240.27) C, 64.99; H, 7.13 oil | 1.1–1.9(8H), 2.28(2H), 4.62(1H), 6.4–7.4(6H) |
| A-29 | 1 | 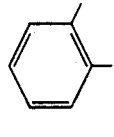 | OH | CO₂H | 5 | C₁₄H₂₀O₃ (236.31) C, 71.16; H, 8.53 oil | 1.1–1.9(8H), 2.30(5H), 4.89(1H), 6.22(2H), 7.0–7.5(4H) |
| A-30 | 1 | 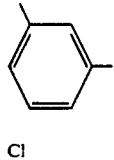 | OH | CO₂H | 5 | C₁₄H₂₀O₄ (252.31) C, 66.65; H, 7.99 oil | 1.1–1.9(8H), 2.29(2H), 3.78(3H), 4.61(1H), 5.89(2H), 6.7–7.3(4H) |
| A-31 | 1 | 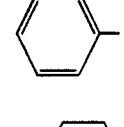 | OH | CO₂H | 5 | C₁₃H₁₇ClO₃ (256.73) C, 60.82; H, 6.67 oil | 1.1–1.9(8H), 2.30(2H), 4.61(1H), 6.38(2H), 7.1–7.4(4H) |
| A-32 | 1 |  | OH | CO₂H | 4 | C₁₂H₁₅FO₃ (226.25) C, 63.70; H, 6.68 103–104 | 1.1–1.9(6H), 2.33(2H), 4.67(1H), 6.9–7.4(2H), 7.00(2H), 7.29(2H) |

TABLE 13-continued $$R^4-CH-(CH_2)_{n^1}-Y^1$$
$$\phantom{R^4-CH-}|$$
$$\phantom{R^4-CH-}X^1$$

| Compound No. | Prepared by the procedure by Ref. Example | R$^4$ | X$^1$ | Y$^1$ | n$^1$ | Molecular formula Physical properties Melting point (°C.) | NMR spectrum TMS as internal standard (δ value, ppm) |
|---|---|---|---|---|---|---|---|
| A-33 | 1 | Cl—C$_6$H$_4$— | OH | CO$_2$H | 4 | C$_{12}$H$_{15}$ClO$_3$ (242.70) C, 59.39; H, 6.23 108~109 | 1.1–1.9(6H), 2.33(2H), 4.66(1H), 7.1–7.4(2H), 7.27(4H) |
| A-34 | 1 | Me—C$_6$H$_4$— | OH | CO$_2$H | 4 | C$_{13}$H$_{18}$O$_3$ (222.28) C, 70.25; H, 8.16 72~73 | 1.1–1.9(6H), 2.30(2H), 2.32(3H), 4.61(1H), 5.99(2H), 7.16(4H) |
| A-35 | 1 | Br—C$_6$H$_4$— | OH | CO$_2$H | 5 | C$_{13}$H$_{17}$BrO$_3$ (301.19) C, 51.84; H, 5.69 87~89 | 1.1–1.9(8H), 2.29(2H), 4.60(1H), 6.36(2H), 7.16(2H), 7.44(2H) |
| A-36 | 1 | F$_3$C—C$_6$H$_4$— | OH | CO$_2$H | 5 | C$_{14}$H$_{17}$F$_3$O$_3$ (290.28) C, 57.93; H, 5.90 oil | 1.1–1.9(8H), 2.30(2H), 4.71(1H), 6.24(2H), 7.4–7.7(4H) |
| A-37 | 4 | imidazolyl-C$_6$H$_4$— | | 4-butanolide | 2 | C$_{13}$H$_{12}$N$_2$O$_2$ (228.25) C, 68.41; H, 12.27 oil | 2.0–2.9(2H), 2.65(2H), 5.54(1H), 7.19(1H), 7.27(1H), 7.44(4H), 7.85(1H) |
| A-38 | 21 | imidazolyl-C$_6$H$_4$— | OH | CO$_2$Me | 3 | C$_{15}$H$_{18}$N$_2$O$_3$ (274.32) C, 65.68; H, 6.61; N, 10.21 104~106 | 1.6–1.9(4H), 2.35(2H), 3.65(3H), 3.79(1H), 4.76(1H), 7.13(1H), 7.25(1H), 7.30(2H), 7.47(2H), 7.70(1H) |
| A-39 | 21 | imidazolyl-C$_6$H$_4$— | OH | CO$_2$Me | 4 | C$_{16}$H$_{20}$N$_2$O$_3$ (288.35) C, 66.65; H, 6.99; N, 9.72 oil | 1.2–1.9(6H), 2.30(2H), 3.63(3H), 3.74(1H), 4.74(1H), 7.12(1H), 7.24(1H), 7.29(2H), 7.46(2H), 7.68(1H) |
| A-40 | 21 | imidazolyl-C$_6$H$_4$— | OH | CO$_2$Me | 5 | C$_{17}$H$_{22}$N$_2$O$_3$ (302.37) C, 67.53; H, 7.33; N, 9.26 77~78 | 1.2–1.9(8H), 2.28(2H), 3.63(3H), 3.66(1H), 4.73(1H), 7.13(1H), 7.24(1H), 7.29(2H), 7.46(2H), 7.69(1H) |
| A-41 | 4 | imidazolyl-N-CH$_2$-C$_6$H$_4$— | | 4-butanolide | 2 | C$_{14}$H$_{14}$N$_2$O$_2$ (242.28) C, 69.40; H, 5.82; N, 11.56 oil | 2.0–2.8(2H), 2.60(2H), 5.12(2H), 5.48(1H), 6.88(1H), 7.07(1H), 7.16(2H), 7.32(2H), 7.53(1H) |
| A-42 | 21 | imidazolyl-N-CH$_2$-C$_6$H$_4$— | OH | CO$_2$Me | 3 | C$_{16}$H$_{20}$N$_2$O$_3$ C, 66.65; H, 6.99; N, 9.72 oil | 1.6–1.9(4H), 2.30(2H), 3.55(1H), 3.62(3H), 4.68(1H), 5.05(2H), 6.86(1H), 6.97(1H), 7.07(2H), 7.32(2H), 7.42(1H) |
| A-43 | 21 | imidazolyl-N-CH$_2$-C$_6$H$_4$— | OH | CO$_2$Me | 4 | C$_{17}$H$_{22}$N$_2$O$_3$ (302.37) C, 67.53; H, 7.33; N, 9.26 oil | 1.2–1.9(6H), 2.26(2H), 3.33(1H), 3.62(3H), 4.66(1H), 5.05(2H), 6.85(1H), 6.97(1H), 7.07(2H), 7.32(2H), 7.41(1H) |
| A-44 | 21 | imidazolyl-N-CH$_2$-C$_6$H$_4$— | OH | CO$_2$Me | 5 | C$_{18}$H$_{24}$N$_2$O$_3$ (316.40) C, 68.33; H, 7.65; N, 8.85 oil | 1.2–1.9(8H), 2.26(2H), 3.17(1H), 3.62(3H), 4.66(1H), 5.06(2H), 6.86(1H), 6.99(1H), 7.08(2H), 7.32(2H), 7.43(1H) |

TABLE 14

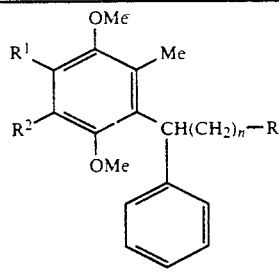

| Compound No. | Prepared by the procedure by Ref. Example | R¹ | R² | R | n | Molecular formula Physical properties Melting point (°C.) | NMR spectrum TMS as internal standard (δ value, ppm) |
|---|---|---|---|---|---|---|---|
| B-1 | 7 | Me | Me | OH | 2 | $C_{20}H_{26}O_3$ oil | 1.87(3H), 2.1-2.3 (1H), 2.19(6H), 2.52(2H), 3.51(3H), 3.57(3H), 3.63 (2H), 4.81(1H), 7.23(5H) |
| B-2 | 7 | Me | Me | OH | 3 | $C_{21}H_{28}O_3$ oil | 1.3-1.8(2H), 1.9-2.5(3H), 2.06 (3H), 2.14(3H), 2.17(3H), 3.24 (3H), 3.59(3H), 3.63(2H), 4.59 (1H), 7.21(5H) |
| B-3 | 7 | Me | Me | OH | 4 | $C_{22}H_{30}O_3$ oil | 1.2-1.8(4H), 1.9-2.4(3H), 2.06 (3H), 2.14(3H), 2.17(3H), 3.25 (3H), 3.60(3H), 3.62(2H), 4.56 (1H), 7.20(5H) |
| B-4 | 7 | Me | Me | OH | 5 | $C_{23}H_{32}O_3$ oil | 1.2-1.8(6H), 1.80 (1H), 2.0-2.5(2H), 2.06(3H), 2.15(3H), 2.18(3H), 3.26(3H), 3.58(2H), 3.60 (3H), 4.57(1H), 7.20(5H) |
| B-5 | 7 | Me | Me | OH | 6 | $C_{24}H_{34}O_3$ oil | 1.1-1.9(8H), 1.9-2.4(3H), 2.07(3H), 2.14(3H), 2.17 (3H), 3.24(3H), 3.60(3H), 3.61 (2H), 4.55(1H), 7.20(5H) |
| B-6 | 8 | Me | Me | Me | 5 | $C_{24}H_{34}O_2$ oil | 0.83(3H), 1.24 (8H), 1.9-2.5(2H), 2.07(3H), 2.14 (3H), 2.17(3H), 3.24(3H), 3.60 (3H), 4.55(1H), 7.20(5H) |
| B-7 | 9 | Me | Me | COOMe | 5 | $C_{25}H_{34}O_4$ oil | 1.1-1.8(6H), 1.9-2.4(2H), 2.07(3H), 2.14(3H), 2.17 (3H), 2.24(2H), 3.24(3H), 3.59 (3H), 3.61(3H), 4.55(1H), 7.20 (5H) |
| B-8 | 10 | MeO | MeO | OH | 4 | $C_{22}H_{30}O_5$ oil | 1.2-1.8(4H), 1.48 (1H), 1.9-2.4(2H), 2.12(3H), 3.34 (3H), 3.59(2H), 3.75(3H), 3.84 (3H), 3.90(3H), 4.41(1H), 7.21 (5H) |
| B-9 | 10 | MeO | MeO | OH | 6 | $C_{24}H_{34}O_5$ oil | 1.1-1.8(8H), 1.9-2.5 (3H), 2.12(3H), 3.33 (3H), 3.58(2H), 3.76 (3H), 3.84(3H), 3.90 (3H), 4.41(1H), 7.21 (5H) |

TABLE 14-continued

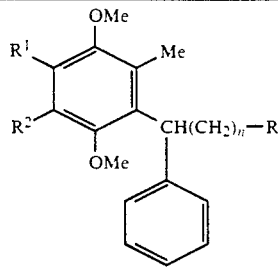

| Compound No. | Prepared by the procedure by Ref. Example | $R^1$ | $R^2$ | R | n | Molecular formula Physical properties Melting point (°C.) | NMR spectrum TMS as internal standard (δ value, ppm) |
|---|---|---|---|---|---|---|---|
| B-10 | 11 | Me | Me | I | 2 | $C_{20}H_{25}IO_2$ oil | 2.13(3H), 2.17(3H), 2.20(3H), 2.81(2H), 3.06(2H), 3.16(3H), 3.61(3H), 4.61(1H), 7.20(5H) |
| B-11 | 11 | Me | Me | I | 3 | $C_{21}H_{27}IO_2$ | 1.5-2.0(2H), 2.0-2.6(2H), 2.06(3H), 2.14(3H), 2.17(3H), 3.19(2H), 3.26(3H), 3.60(3H), 4.60(1H), 7.22(5H) |
| B-12 | 11 | Me | Me | I | 4 | $C_{22}H_{29}IO_2$ | 1.2-1.8(2H), 1.86(2H), 1.9-2.5(2H), 2.08(3H), 2.14(3H), 2.17(3H), 3.13(2H), 3.22(3H), 3.60(3H), 4.55(1H), 7.20(5H) |
| B-13 | 11 | Me | Me | I | 6 | $C_{24}H_{33}IO_2$ | 1.1-1.6(6H), 1.75(2H), 1.9-2.4(2H), 2.07(3H), 2.14(3H), 2.17(3H), 3.12(2H), 3.24(3H), 3.60(3H), 4.55(1H), 7.20(5H) |
| B-14 | 12 | Me | Me | CN | 2 | $C_{21}H_{25}NO_2$ | 2.14(6H), 1.75(3H), 2.25(2H), 2.61(2H), 3.14(3H), 3.61(3H), 4.61(1H), 7.20(5H) |
| B-15 | 12 | Me | Me | CN | 3 | $C_{22}H_{27}NO_2$ oil | 1.4-1.8(2H), 2.0-2.6(2H), 2.05(3H), 2.16(3H), 2.19(3H), 2.33(2H), 3.26(3H), 3.61(3H), 4.59(1H), 7.21(5H) |
| B-16 | 12 | Me | Me | CN | 4 | $C_{23}H_{29}NO_2$ oil | 1.2-1.9(4H), 1.9-2.5(2H), 2.07(3H), 2.14(3H), 2.17(3H), 2.28(2H), 3.22(3H), 3.60(3H), 4.55(1H), 7.20(5H) |
| B-17 | 12 | Me | Me | CN | 6 | $C_{25}H_{33}NO_2$ oil | 1.1-1.8(8H), 1.9-2.4(2H), 2.6(3H), 2.14(3H), 2.17(3H), 2.26(2H), 3.23(3H), 3.60(3H), 4.55(1H), 7.20(5H) |
| B-18 | 11 | MeO | MeO | I | 4 | $C_{22}H_{29}IO_4$ oil | 1.2-1.6(2H), 1.84(2H), 2.0-2.4(2H), 2.13(3H), 3.13(2H), 3.32(3H), 3.75(3H), 3.83(3H), 3.89(3H), 4.40(1H), 7.20(5H) |
| B-19 | 13 | Me | Me | COOH | 2 | $C_{21}H_{26}O_4$ 139-140 | 2.07(3H), 2.13(3H), 2.17(3H), 2.31(3H), 2.54(2H), 3.20(3H), 3.60(3H), 4.57(1H), 7.22(5H), 8.83(1H) |
| B-20 | 13 | Me | Me | COOH | 3 | $C_{22}H_{28}O_4$ 142-143 | 1.4-1.8(2H), 1.9-2.4(2H), 2.07(3H), 2.14(3H), 2.17(3H), 2.35(2H), 3.24(3H), 3.59(3H), 4.58(1H), 7.19(5H), 10.1(1H) |
| B-21 | 13,14 | Me | Me | COOH | 4 | $C_{23}H_{30}O_4$ | 1.1-1.5(2H), 1.63 |

TABLE 14-continued

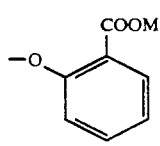

| Compound No. | Prepared by the procedure by Ref. Example | $R^1$ | $R^2$ | R | n | Molecular formula Physical properties Melting point (°C.) | NMR spectrum TMS as internal standard (δ value, ppm) |
|---|---|---|---|---|---|---|---|
| | | | | | | oil | (2H), 2.0-2.4(2H), 2.06(3H), 2.14(3H), 2.17(3H), 2.30(2H), 3.23(3H), 3.59(3H), 4.54(1H), 7.19(5H), 9.10(1H) |
| B-22 | 13.15 | Me | Me | COOH | 5 | $C_{24}H_{32}O_4$ oil | 1.1-1.8(6H), 1.9-2.4(2H), 2.07(3H), 2.14(3H), 2.17(3H), 2.28(2H), 3.24(3H), 3.60(3H), 4.55(1H), 7.20(5H), 8.65(1H) |
| B-23 | 13 | Me | Me | COOH | 6 | $C_{25}H_{34}O_4$ oil | 1.1-1.8(8H), 1.9-2.4(2H), 2.07(3H), 2.14(3H), 2.17(3H), 2.28(2H), 3.24(3H), 3.60(3H), 4.55(1H), 7.20(5H), 8.20(1H) |
| B-24 | 16 | Me | Me | $-C{\equiv}C(CH_2)_3$ | $CC.CH_2OH$ | 3 | $C_{29}H_{36}O_3$ oil | 1.2-1.8(4H), 1.85 (1H), 2.0-2.6(8H), 2.07(3H), 2.14(3H), 2.17(3H), 3.26(3H), 3.60(3H), 4.20(2H), 4.58(1H), 7.20(5H) |
| B-25 | 16 | Me | Me | $-C{\equiv}C.CH_2OH$ | 3 | $C_{24}H_{30}O_3$ oil | 1.3-1.7(2H), 1.78 (1H), 2.0-2.6(4H), 2.07(3H), 2.14(3H), 2.17(3H), 3.26(3H), 3.60(3H), 4.19(2H), 4.57(1H), 7.21(5H) |
| B-26 | 16 | Me | Me | $-C{\equiv}C.CH_2CH_2OH$ | 4 | $C_{26}H_{34}O_3$ oil | 1.2-1.7(4H), 1.83 (1H), 1.9-2.4(4H), 2.07(3H), 2.15(3H), 2.17(3H), 2.35(2H), 3.25(3H), 3.60(3H), 3.63(2H), 4.56(1H), 7.20(5H) |
| B-27 | 17 | Me | Me | OH | 8 | $C_{26}H_{38}O_3$ oil | 1.1-1.7(12H), 1.9-2.4(2H), 2.08(3H), 2.14(3H), 2.17(3H), 2.27(1H), 3.23(3H), 3.53(2H), 3.58(3H), 4.56(1H), 7.19(5H) |
| B-28 | 16 | Me | Me | $-C{\equiv}C.CH_2OH$ | 6 | $C_{27}H_{36}O_3$ oil | 1.1-1.7(8H), 1.83 (1H), 1.9-2.4(4H), 2.07(3H), 2.14(3H), 2.17(3H), 3.23(3H), 3.60(3H), 4.20(2H), 4.55(1H), 7.20(5H) |
| B-29 | 18 | Me | Me | -O-C₆H₄-COOMe (ortho) | 2 | $C_{28}H_{32}O_5$ oil | 2.06(3H), 2.15(3H), 2.17(3H), 2.76(2H), 3.06(3H), 3.52(3H), 3.80(3H), 3.92(2H), 4.85(1H), 6.75(1H), 6.88(1H), 7.0-7.4 (6H), 7.72(1H) |

TABLE 14-continued

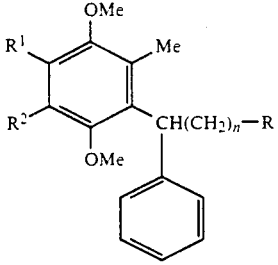

| Compound No. | Prepared by the procedure by Ref. Example | $R^1$ | $R^2$ | R | n | Molecular formula Physical properties Melting point (°C.) | NMR spectrum TMS as internal standard (δ value, ppm) |
|---|---|---|---|---|---|---|---|
| B-30 | 20 | Me | Me | 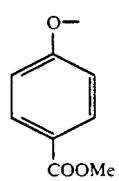 | 2 | $C_{27}H_{30}O_5$ 132–133 | 2.06(3H), 2.09(3H), 2.15(3H), 2.79(2H), 3.20(3H), 3.54(3H), 4.11(2H), 4.81(1H), 6.83(1H), 7.03(1H), 7.22(5H), 7.40(1H), 8.07(1H), 9.94(1H) |
| B-31 | 18 | Me | Me | 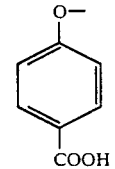 | 6 | $C_{32}H_{40}O_5$ oil | 1.2–1.6(6H), 1.84 (2H), 2.0–2.5(2H), 2.08(3H), 2.14(3H), 2.17(3H), 3.23(3H), 3.60(3H), 3.85(3H), 3.94(2H), 4.55(1H), 6.85(2H), 7.20(5H), 7.95(2H) |
| B-32 | 20 | Me | Me | 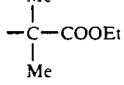 | 6 | $C_{31}H_{38}O_5$ oil | 1.1–1.7(6H), 1.72 (2H), 2.0–2.5(2H), 2.08(3H), 2.14(3H), 2.17(3H), 3.23(3H), 3.59(3H), 3.93(2H), 4.56(1H), 6.84(2H), 7.19(5H), 8.01(2H), 12.0(1H) |
| B-33 | 19 | Me | Me | 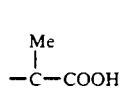 | 4 | $C_{28}H_{40}O_4$ oil | 1.1–1.6(6H), 1.12 (6H), 1.20(3H), 1.9–2.4(2H), 2.07 (3H), 2.14(3H), 2.17(3H), 3.24(3H), 3.60(3H), 4.07(2H), 4.54(1H), 7.20(5H) |
| B-34 | 20 | Me | Me |  | 4 | $C_{26}H_{36}O_4$ oil | 1.1–1.6(6H), 1.15 (6H), 1.9–2.4(2H), 2.07(3H), 2.14(3H), 2.17(3H), 3.22(3H), 3.58(3H), 4.55(1H), 7.19(5H), 11.1(1H) |
| B-35 | 19 | MeO | MeO |  | 4 | $C_{28}H_{40}O_6$ oil | 1.1–1.6(6H), 1.12 (6H), 1.20(3H), 1.9–2.4(2H), 2.12 (3H), 3.33(3H), 3.75 (3H), 3.83(3H), 3.89 (3H), 4.07(2H), 4.38 (1H), 7.20(5H) |
| B-36 | 20 | MeO | MeO | Me<br>—C—COOH<br>Me | 4 | $C_{26}H_{36}O_6$ oil | 1.1–1.6(6H), 1.15 (6H), 1.9–2.4(2H), 2.11(3H), 3.33(3H), 3.74(3H), 3.83(3H), 3.89(3H), 4.38(1H), 7.20(5H), 9.00(1H) |
| B-37 | 11 | Me | Me | I | 5 | $C_{23}H_{31}IO_2$ | 1.2–1.6(4H), 1.79 (2H), 1.9–2.3(2H), 2.07(3H), 2.15(3H), 2.18(3H), 3.12(2H), 3.24(3H), 3.60(3H), 4.55(1H), 7.20(5H) |

TABLE 14-continued

Structure:

R¹, R² on benzene ring with OMe (top), Me, OMe (bottom), and CH(CH₂)ₙ—R substituent bearing a phenyl group.

| Compound No. | Prepared by the procedure by Ref. Example | R¹ | R² | R | n | Molecular formula Physical properties Melting point (°C.) | NMR spectrum TMS as internal standard (δ value, ppm) |
|---|---|---|---|---|---|---|---|
| B-38 | 12 | Me | Me | CN | 5 | $C_{24}H_{31}NO_2$ | 1.2–1.8(6H), 1.9–2.4(2H), 2.07(3H), 2.15(3H), 2.18(3H), 2.25(2H), 3.23(3H), 3.61(3H), 4.55(1H), 7.21(5H) |
| B-39 | 16 | Me | Me | —C≡C.CH₂OH | 5 | $C_{26}H_{34}O_3$ | 1.1–1.6(6H), 1.77(1H), 1.9–2.4(4H), 2.08(3H), 2.15(3H), 2.18(3H), 3.25(3H), 3.61(3H), 4.20(2H), 4.56(1H), 7.21(5H) |

REFERENCE EXAMPLE 22

A THF solution (50 ml) of 2-bromo-3,5,6-trimethyl-1,4-dimethoxybenzene (10 g, 40 mmole) was cooled to −70° C. under an atmosphere of argon, and n-butyllithium (20%, hexane solution) was added dropwise to the solution, followed by stirring at −70° C. for 10 minutes. Subsequently, cuprous bromide (5.70 g, 40 mmole) was added to the mixed solution, and the temperature of the reaction solution was raised to 0° C. The reaction solution was cooled again to −70° C., and crotyl bromide (5.4 g, 40 mmole) was added. Stirring was effected until the reaction solution reached the room temperature, and the reaction was suspended by adding 100 ml of water. The reaction solution was extracted with IPE, and the organic layer was washed with water, dried and concentrated under reduced pressure. The residue was dissolved in THF (50 ml), and sodium boron hydride (1 g) was added to the solution. Boron trifluoride etherate (1.5 ml) was added dropwise to the reaction solution, and after stirring was effected for 1 hour and 50 ml of water was added, 3N aqueous potassium hydroxide solution (50 ml) was added dropwise to the mixed solution. 30% Aqueous hydrogen peroxide solution was added to the reaction solution under cooling, followed by stirring under the same conditions for 18 hours. The reaction solution was extracted with IPE, and the organic layer was washed with water, dried and concentrated under reduced pressure. The residue was purified by silica gel column chromatography (eluting solution: IPE) to give 3-(3,5,6-trimethyl-1,4-dimethoxyphenyl)-butan-1-ol (3 g, 30%). δ3.67(3H,s), 3.62(3H,s), 3.49(2H,m), 2.27(3H,s), 2.17(3H,s), 2.02(2H,m), 1.37(3H,d,7Hz)

REFERENCE EXAMPLE 23

A dichloromethane solution (25 ml) of oxalyl chloride (1 ml, 11 mmole) was cooled to −70° C. under an atmosphere of argon, and a solvent mixture of DMSO (1.7 ml, 22 mmole) and dichloromethane (5 ml) was added dropwise to the solution, while maintaining its temperature at not higher than −60° C. Subsequently, a dichloromethane solution (10 ml) of 3-(3,5,6-trimethyl-1,4-dimethoxybenzyl)-butan-1-ol (3 g, 11 mmole) was added dropwise to the mixed solution, followed by stirring at −70° C. for 15 minutes, and triethylamine (7 ml, 50 mmole) was added dropwise. Then, stirring was continued until the temperature of the reaction solution reached the room temperature, and water (50 ml) was added to the reaction solution, followed by concentration under reduced pressure. The residue was extracted with IPE, and the organic layer was washed with IPE, dried and concentrated under reduced pressure. The crude product was purified by silica gel column chromatography to give 3-(3,5,6-trimethyl-1,4-dimethoxybenzyl)butanal (2.7 g, 90%). δ9.68(1H,t), 3.83(1H,m), 2.67(3H,s), 3.60(3H,s), 2.89 (2H,dd,2Hz,6Hz), 2.27(3H,s), 2.16(6H,s), 1.33(3H,s).

REFERENCE EXAMPLE 24

DMSO (30 ml) was added to sodium hydroxide (1 g, 24 mmole, 60% oil suspension was washed with hexane and dried under reduced pressure) under an atmosphere of argon, followed heating at 80° C. for 1 hour with stirring. After cooling, 3-carboxypropyltriphenyl phosphonium bromide (4.6 g, 11 mmole) was added to the solution, followed by stirring at room temperature. After stirring for 10 minutes, a THF solution (5 ml) of 3-(3,5,6-trimethyl-1,4-dimethoxyphenyl)butanal (2.7 g, 11 mmole) was added dropwise to the mixed solution. The reaction solution was stirred at room temperature for 2 hours, and water (50 ml) was added to it. The organic layer was washed with toluene (100 ml), and the water layer was adjusted to pH 4 with 2N hydrochloric acid, followed by extraction with IPE. The organic layer was washed with water, dried and concentrated under reduced pressure, and the crude product was purified by silica gel column chromatography (eluting solution: IPE) to give 7-(1,4-dimethoxy-3,5,6- trimethylphenyl)-4-octenoic acid (2.2 g, 68%). δ8.80 (1H,COOH), 5.38(2h,m), 3.63(3H,s), 3.60(3H,s), 3.25 (1H,s), 2.40(6H,m), 2.25(3H,s), 2.15(6H,s), 1.30(3H,d,7Hz)

This compound was dissolved in ethyl acetate (20 ml), and 5% Pd-C (0.2 g) was added to the solution, followed by catalytic reduction at ambient temperature. 6 Hours later, the catalyst was filtered out, and the filtrate was concentrated under reduced pressure to give 7-(1,4-dimethoxy-3,5,6-trimethyl)phenyloctanoic acid (2 g, 90%). δ9.20(1H,COOH), 3.65(6H,s), 3.23(1H,m), 2.30(2H,m), 2.24 (3H,s), 1.66(6H,m), 1.29(3H,d,7Hz).

The novel quinone derivatives according to the present invention possess metabolism ameliorating action for polyunsaturated fatty acids, particularly production inhibitory activity of lipid peroxides antioxidant activity) or production inhibitory activity of 5-lipoxygenase products in arachidonate cascade, and are of use as drugs, such as antiasthmatic, antiallergic agent and cerebralcirculatory metabolism ameliorating agent.

We claim:

1. A compound of the formula

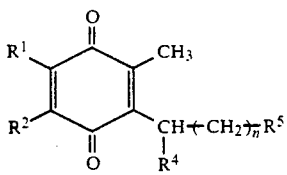

wherein $R^1$ and $R^2$ are the same or different, and independently are methyl or methoxy, or $R^1$ and $R^2$ together represent —CH=CH—CH=CH—, $R^4$ is (a) a phenyl, (b) a naphthyl or (c) thienyl or furyl, each of (a), (b) or (c) being unsubstituted or substituted by 1 to 5 substituents selected from the group consisting of hydroxyl, a halogen, an alkyl having 1 to 3 carbon atoms, an alkoxy having 1 to 3 carbon atoms, acetyl, phenyl, p-tolyl, m-tolyl, a pyridyl, 3-pyridylmethyl, benzoyl, methylenedioxy, trimethylene, 1-imidazolyl and 1-imidazolylmethyl, $R^5$ is carboxyl, an alkoxycarbonyl having 2 to 5 carbon atoms, phenoxycarbonyl, and n is an integer of 2 to 10, or the hydroquinone form of said compound.

2. A compound as claimed in claim 1, wherein $R^4$ is (a) a phenyl or (b) a naphthyl, each of (a) or (b) being unsubstituted or substituted by 1 to 5 substituents selected from the group consisting of hydroxyl, a halogen, an alkyl having 1 to 3 carbon atoms, an alkoxy having 1 to 3 carbon atoms, acetyl, phenyl, p-tolyl, m-tolyl, a pyridyl, 3-pyridylmethyl, benzoyl, methylenedioxy, trimethylene, 1-imidazolyl and 1-imidazolylmethyl.

3. A compound as claimed in claim 1, wherein $R^4$ is thienyl or furyl which is unsubstituted or substituted by 1 to 5 substituents selected from the group consisting of hydroxyl, a halogen, an alkyl having 1 to 3 carbon atoms, an alkoxy having 1 to 3 carbon atoms, acetyl, phenyl, p-tolyl, m-tolyl, a pyridyl, 3-pyridylmethyl, benzoyl, methylenedioxy, trimethylene, 1-imidazolyl and 1-imidazolylmethyl.

4. A compound as claimed in claim 1, wherein $R^1$ and $R^2$ are the same and each is methyl, $R^4$ is a phenyl group which may be substituted by methyl, methoxy or a halogen, $R^5$ is carboxyl, and n is 4, 5 or 6, or its hydroquinone form.

5. A compound as claimed in claim 4, wherein $R^4$ is phenyl or a phenyl having a halogen at meta or para position on the phenyl ring.

6. A compound as claimed in claim 1, wherein the compound is 7-(3,5,6-trimethyl-1,4-benzoquinon-2-yl)-7-phenylheptanoic acid.

7. A compound as claimed in claim 1, wherein the compound is 6-(3,5,6-trimethyl-1,4-benzoquinon-2-yl)-6-(4-methoxyphenyl)hexanoic acid.

8. A compound as claimed in claim 1, wherein the compound is 7-(3,5,6-trimethyl-1,4-benzoquinon-2-yl)-7-(4-methoxyphenyl)heptanoic acid.

9. A compound as claimed in claim 1, wherein the compound is 7-(3,5,6-trimethyl-1,4-benzoquinon-2-yl)-7-(4-fluorophenyl)heptanoic acid.

10. A compound as claimed in claim 1, wherein the compound is 7-(3,5,6-trimetyl-1,4-benzoquinon-2-yl)-7-(4-methylphenyl)heptanoic acid.

11. A pharmaceutical composition which comprises a pharmaceutically effective amount of a compound according to claim 1 or its hydroquinone form in association with a pharmaceutically acceptable carrier therefor.

* * * * *